US008648231B2

(12) United States Patent
Yang et al.

(10) Patent No.: US 8,648,231 B2
(45) Date of Patent: Feb. 11, 2014

(54) WALL-ASSOCIATED KINASE-LIKE POLYPEPTIDE MEDIATES NUTRITIONAL STATUS PERCEPTION AND RESPONSE

(75) Inventors: Zhenbiao Yang, Riverside, CA (US); Stephen Karr, Camarillo, CA (US)

(73) Assignee: The Regents of the University of California, Oakland, CA (US)

( * ) Notice: Subject to any disclaimer, the term of this patent is extended or adjusted under 35 U.S.C. 154(b) by 636 days.

(21) Appl. No.: 12/624,647

(22) Filed: Nov. 24, 2009

(65) Prior Publication Data

US 2010/0146669 A1 Jun. 10, 2010

Related U.S. Application Data

(60) Provisional application No. 61/117,421, filed on Nov. 24, 2008.

(51) Int. Cl.
*C12N 15/82* (2006.01)
*A01H 5/00* (2006.01)

(52) U.S. Cl.
USPC ........... 800/290; 800/278; 800/289; 800/298; 435/419

(58) Field of Classification Search
USPC .................................. 800/278, 289, 290, 298
See application file for complete search history.

(56) References Cited

U.S. PATENT DOCUMENTS

| | | | |
|---|---|---|---|
| 7,674,951 B1 | 3/2010 | Joshi | |
| 2005/0223428 A1 | 10/2005 | Torii et al. | |
| 2008/0057093 A1 | 3/2008 | Wan et al. | |
| 2010/0095405 A1* | 4/2010 | Arruda et al. | 800/290 |
| 2010/0146672 A1 | 6/2010 | Yang et al. | |
| 2010/0170006 A1 | 7/2010 | Yang et al. | |

FOREIGN PATENT DOCUMENTS

| | | |
|---|---|---|
| WO | 2007138070 A2 | 12/2007 |
| WO | 2008074116 A1 | 6/2008 |
| WO | 2010060096 A2 | 5/2010 |
| WO | 2010060099 A2 | 5/2010 |
| WO | 2010080589 A2 | 7/2010 |

OTHER PUBLICATIONS

Whisstock J.C. et al. Prediction of protein function from protein sequence and structure. Q Rev Biophys. Aug. 2003;36(3):307-40. Review.*
Verica et al. The cell wall-associated kinase (WAK) and WAK-like kinase gene family. Plant Physiol. Jun. 2002;129(2):455-9.*
Baharlou, Simin, International Preliminary Report on Patentability and Written Opinion, Date of Issuance of Report: May 24, 2011, International Application Number: PCT/US2009/065766.
Desprez et al., "Resistance against Herbicide Isoxaben and Cellulose Deficiency Caused by Distinct Mutations in Same Cellulose Synthase Isoform CESA6", Plant Physiology, Feb. 2002, vol. 128 pp. 482-490.
Eyuboglu, Banu et al. "Molecular characterisation of the Strubbelig-Receptor Family of genes encoding putative leucine-rich repeat receptor-like kinases in *Arabidopsis thaliana*", BMC Plant Biology 2007, vol. 7, Issue 16, Mar. 30, 2007, pp. 1-24.
Joo, Noh Eun, International Search Report and Written Opinion, Date of Mailing of Report: Sep. 27, 2010, International Application Number: PCT/US2009/068682.
Kim, Jun Kyung. International Search Report and Written Opinion, Date of Mailing of Report: Aug. 5, 2010 International Application No. PCT/US2009/065766.
Kim, Yun-Kyung. International Search Report and Written Opinion, Date of Mailing of Report: Jul. 8, 2010 International Application No. PCT/US2009/065777.
Lindner, Nora. International Preliminary Report on Patentability and Written Opinion, Date of Issuance of Report: May 24, 2011, International Application No. PCT/US2009/065777.
Lindner, Nora. International Preliminary Report on Patentability and Written Opinion, Date of Issuance of Report: Jun. 21, 2011, International Application No. PCT/US2009/068682.
Oh et al., "Recombiant brassinosteroid insensitive 1 receptor-like kinase autophophorylates on serine and threonine residues and phosphorylates a conserved peptide motif in vitro", Plant Physiology, Oct. 2000, pp. 751-765, vol. 124.
Shiu et al., "Plant receptor-like kinase gene family: diversity, function, and signaling", Sci. STKE, Dec. 18, 2001, pp. 1-13, vol. 113.
Shpak et al., "Dominant-negative receptor incovers reduncancy in the *Arabidopsis* ERECTA leucine-rich repeat receptor-like kinase signaling pathway that regulates organ shape", The Plant Cell, May 2003, pp. 1095-1110, vol. 15.
Tanaka, Masaru et al. "Analysis of genes developmentally regulated during storage root formation of sweet potato", Journal of Plant Physiology, Jan. 12, vol. 162, Issue 1, pp. 91-102.
Wei, Tang et al. "Increasing cellulose production and transgenic plant growth in forest tree species", Journal of Forestry Research, Mar. 2005, vol. 16, Issue 1, pp. 67-72.
Verica, J.A. et al. "The cell wall-associated kinase (WAK) and WAK-like kinase gene family", Plant Physiol., 2002, vol. 129, pp. 455-459.
Verica, J. A. et al. "Tissue-specific and developmentally regulated expression of a cluster of tandemly arrayed cell wall-associated kinase-like kinase genes in *Arabidopsis*", Plant Physiol. , 2003, vol. 133, pp. 1732-1746.
Wagner, T. A. et al., "Wall-associated kinases are expressed throughout plant development and are required for cell expansion" The Plant Cell, 2001, vol. 13, pp. 303-318.
Xuewen, H. et al., "Involvement of a cell wall -associated kinase. WAKL4, in *Arabidpsis* mineral responses", Plant Physiol., 2005, vol. 139, pp. 1704-1716.

* cited by examiner

*Primary Examiner* — Cynthia Collins
(74) *Attorney, Agent, or Firm* — Joseph R. Baker, Jr.; Gavrilovich, Dodd & Lindsey LLP

(57) ABSTRACT

The disclosure relates to methods for modulating plant growth and organogenesis using dominant-negative receptor-like kinases. The disclosure further provides a method for increasing plant yield relative to corresponding wild type plants comprising modulating the expression in a plant of a nucleic acid encoding a Wall-Associated Kinase-like 14 polypeptide or a homolog thereof, and selecting for plants having increased yield or growth on a nutrient deficient substrate.

11 Claims, 9 Drawing Sheets

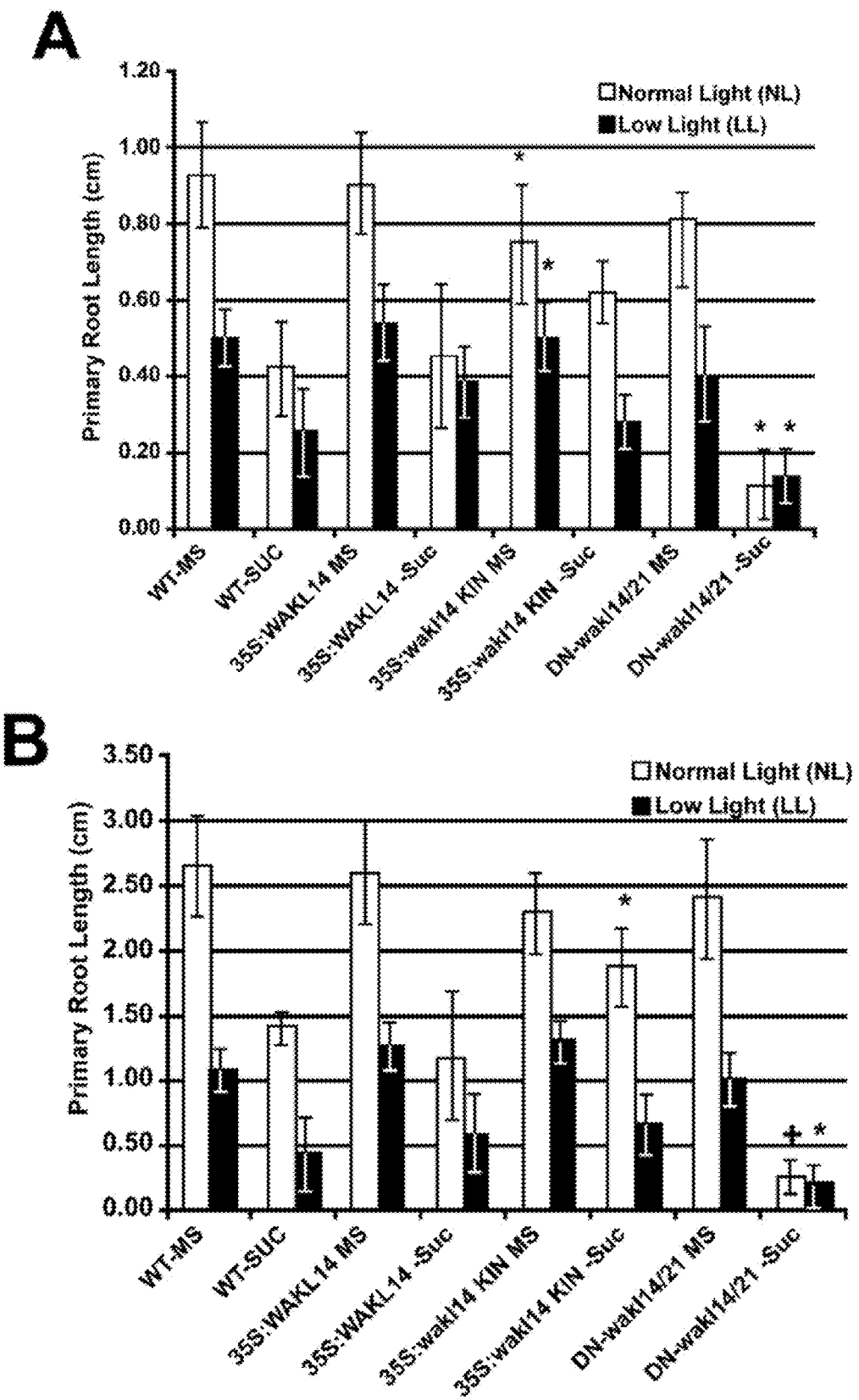
FIGURE 3A-B

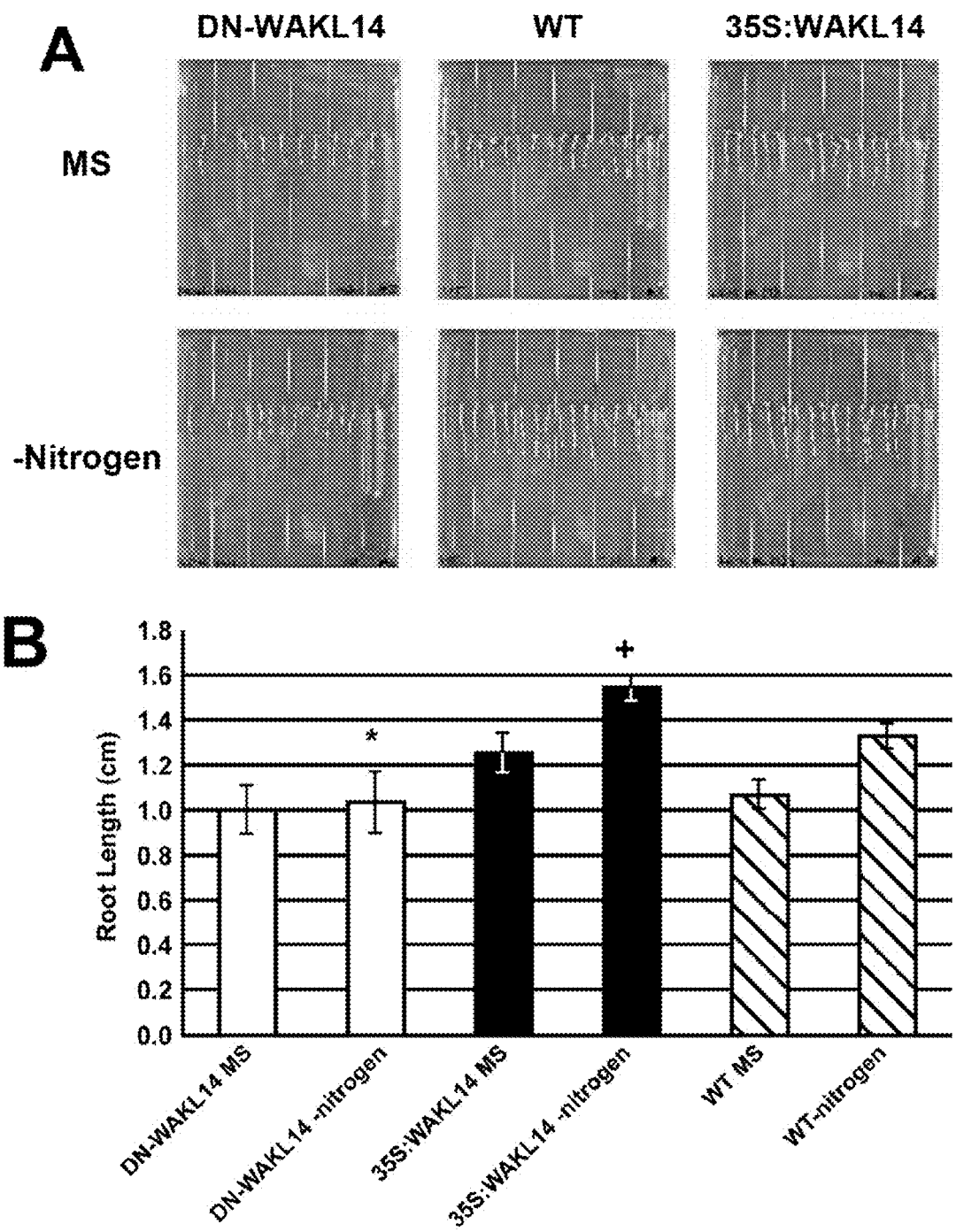
FIGURE 4A-B

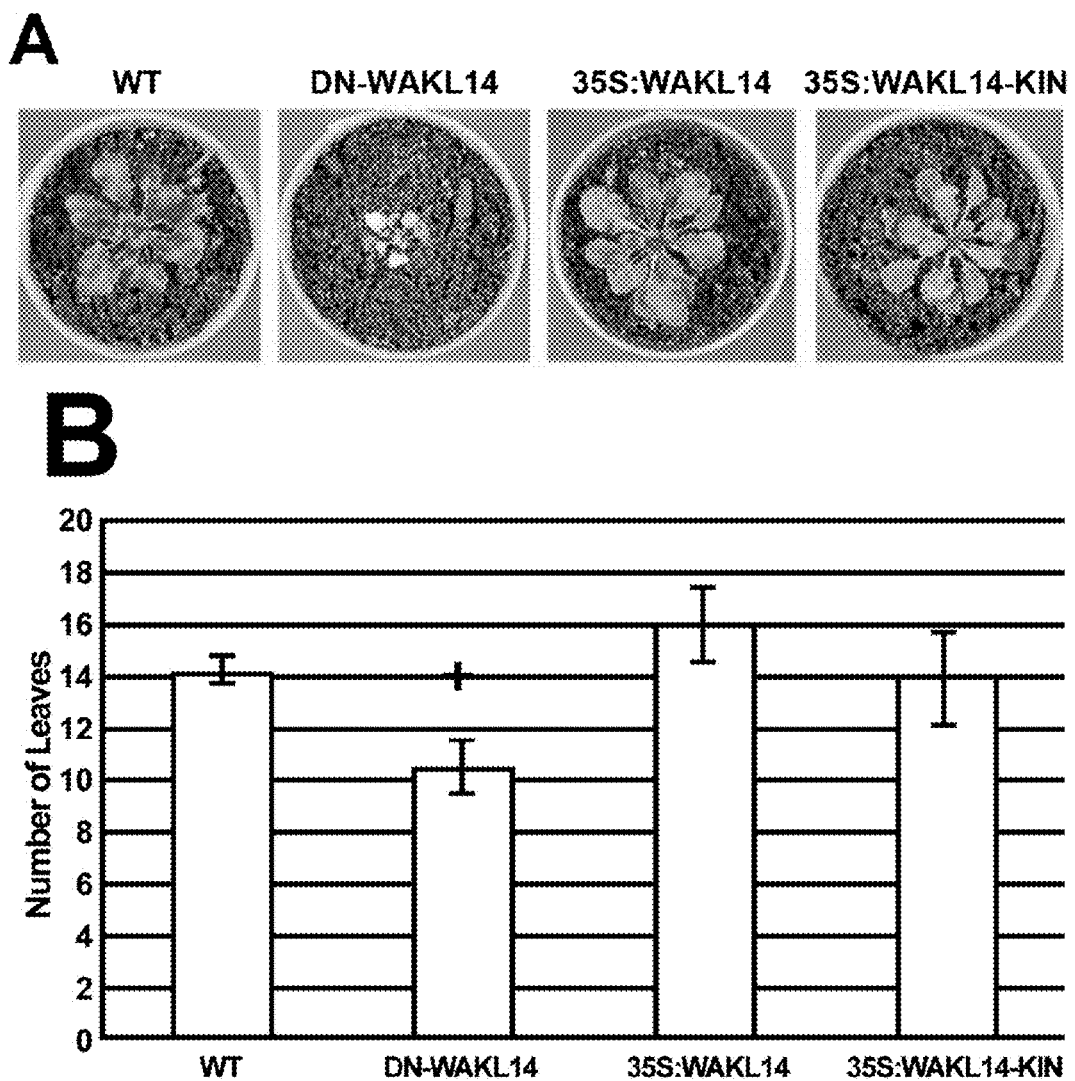
FIGURE 5A-B

Sequence Alignments for WAKL14 and WAKL21 to Tomato, Grape, Poplar, Rice and Corn

```
Tomato      ---------MGFHHIIIIRFVFSILLGWLSSSVEATN---STKCNQYCGAAGSYSPRVSY
Grape       ----------------MRKALQRTILALICTVTLVS---AIK-NDSCG-TGKSAKRVHY
Poplar      ---------MSLRQESLLLFITFITIFIATTSPTTKAQKSGSNCASSCG-IGKSARVVPY
WAKL14      MLRSIFDFNQRSTKMVMISHKLDLILVFIIVIGGSIFRRVSANFTVPCN-GRCGGLTLPY
WAKL21      -----------------MAETPQPYLIFVFFVFTLTVAT--------QTTGSVKCKTSLLRY
Rice        ----------MRGAARLLLPLVVLLLHAARGSAGSTGGGGNGSCTQSCG-----RMRVPY
Zea mays    -----------MHHQLLLFLFLLLLDATTFAAPAGP------CNRRCG-----STTVPY
                                                          :       . : *

Tomato      PFGFSEG---CGIRLDCTESTGEIRIG----------EYIIQNVTSET---LMVNFSMNCSRPI
Grape       PFGFSSD---SPIKLNCSK-EGEIEIQ----------NFKVQNVTTDS---IIINLPAQCQREI
Poplar      PFGFSNG---CPIQLNCESTEGEIKIG----------EFQVQNITPNG---ILVNLPADCNRSI
WAKL14      PFGFSNG---CSIRFDCSAAE-KPMIG----------DFSVQNVTENS---IFVGLSHNCTRKI
WAKL21      PFGFSDG---YPIRFNCSEITGEAVIG----------EFAVQEVTNSN---IYVEIPPVCKRNI
Rice        PFGFSRG---CTVQLGCDDASGTAWLGG---TRGLGLLVSNVTPRA---IVLTLPPNCSRPL
Zea mays    PFGFSGGGACPILLACNATASTALLPRSTAAAAASYPVQSFDSAASTFLVSLVPSCGRGV
            *****  .       : : *        :                  :...    : : :   * * :

Tomato      ED-LQQFDRTNFGMT-WRNGLLLHNCKVP-----KSECTIPSEILSTRLNIQSCDSKKEN
Grape       QK-IEPLFGKNYALS-SKNSLLFQNCSSS-----SSGCVIPTSVFNGQNKLNNCNGKSDN
Poplar      ET-IRPLFGLNYGPS-WQNSLLLQNCSKP-----SNSCVISRSPFQGELHSKNCEAAKND
WAKL14      ED-MNPLFGENFAPT-SENSFLMENCNRT-----TDGCSIKQKFLENVLKLKSCDATGN-
WAKL21      RK-IEQLFRENLAPSKLQNIILVQGCKKQN---KSSNCLIRNKFVENRLNLSKCKSP---
Rice        NESLDALFTDNYAPT-AQNALVVSSCDPQ-----AAARLSNCSIPPEAYLEKSCNSIRCV
Zea mays    AEARAALGGAGYGVSSRTGLFLRGGCGRAAGSRSPSDCNVPSGVMAAILRTVQCGGGNDS
               :     . . :   . ::   .*                           .* .

Tomato      -VSCYS-----------EARADYLDYQKLKN--TGCGTVISSILIGMDNDTMKSSAMFI
Grape       NISCFPL----------DSESEFMSFANVTG--TGCKFLLLSMAVEWRNN----SAVSL
Poplar      NLSCYSLP---------YSGIDTLSYEGVNS--TQCSSVFSSLALGSDS-----PVVSF
WAKL14      -ISCFSLDSNS-----SSKNSAKFFSMKTLRN--SSCSLLFSSIAFESVGVN---AGIAL
WAKL21      -VSCLDGAT--------TTTADVMSLGDVVNG-SGCKYWFSSISQ---------SQVSV
Rice        LPSTKANVDG-------TNVTDPFLNRSEMRRLGSDCRGLVSASIYSNT------AGPAL
Zea mays    SWTCVLSAPPAPGSPAAARGQGQFMRWDEVAA--AGCEDALTSAVYAYSPQ----GVPSI
                   :                     :    :    : *  . :

Tomato      EFQTMELAWGLEGDC---------ACHNDANCTNVSLP-GNRKGFRCRCKDGFVGDGFSDG
Grape       ELGTAQLGWWLDHPC---------HCAPNAKHTNLTVP-GG-FGCRCSCKEGFDGDGFKDG
Poplar      QYERIELEWWLEGHCRDT-----FCSKNANCSEVKLQ-NGTVGFRCHCYDGFAGDGFTTG
WAKL14      EFERVRLGWWLKGGCESG------TCAANTDCTDVETP-HGYAGHRCSCLDGFHGDGYTN-
WAKL21      NLGRLKLDWWLKGSCSNT-----TCSENADCAKVKLD-DGGLGHRCTCREGFSGKAFTVP
Rice        QLTALELDWWVQGRCG--------CSSHAICDGFTPPSTQKEAFRCECQEGFEGDGYTAG
Zea mays    QFGIAEMGWWVDGRCGDGGGGGGRCARNATCHDVQTP-GGAWGHRCACVDGMAGDFAAG
            :      .: *  :.   *          *   .:    .     . ** * :*: *..:

Tomato      DGCRKVSRCNPSRYLSGRCGGTTRIGVLVGGIIAGAGLMAALAVLCYCIRRR---SASLK
Grape       DGCQEVTDCNASKYMSGTCGGTTRVAVLVGGVIVGASLMSTVALICYCIRRR----SYLR
Poplar      NGCRRGEPTWLYICLH-------LFLLFIMRLIAGASLMAVFALLCYFVKKK---STSMR
WAKL14      PCQRALPECRGSKLVWRHCR--SNLITIVGGTVGGAFLLAALAFFFFCKRRR---STPLR
WAKL21      GGCHRLVYKRKGLHK--------LVVLGTAGILVGVLVIVVLIATYFFRNKQ---SASSE
Rice        AGCRRVPKCNPSKYLSGSCGKLVQIGLLVAGVFFGAMVMGITCLVYHLLRRR---SAALR
Zea mays    QGCYYDGAPRERSAKK-------IVLVVAAGVAASVAAATGALLLCWLQCRRRKAGRSAS
                                             .          ..            ::
```

FIGURE 7A

```
Tomato     KRMSARRLLSEAAGSNSVHVFQYKEIERATNSFSEKQRLGIGAYGTVYAGKLHSD----E
Grape      RRMSAKRLICEAAGNSSVPLYPYKEVERATNGFSEKQRLGTGAYGTVFAGKLHND----E
Poplar     NRSSAKRLLCEAAGNSSVPFFQYKEIERATNGFSEKQRLGTGAYGTVYSGKLHND----D
WAKL14     SHLSAKRLLSEAAGNSSVAFFPYKEIEKATDGFSEKQKLGIGAYGTVYRGKLQND----E
WAKL21     RASIANRLLCELAGNSSVPFYTYKEIEKATDSFSDKNMLGTGAYGTVYAGEFPNS----S
Rice       SQKSTKRLLSEAS--CTVPFYTYREIDRATNGFAEDQRLGTGAYGTVYAGRLSNN----R
Zea mays   ERLAAMRLLSEAATSSGVPVYSYGEIARATNSFSHTHRLGTGAYGTVYVGKLPGTGSAPA
             :  **:.*  :       * .: *  *: :**:.*:.  : ** ******:  *.:  .

Tomato     WVAIKKLRHRDPDGVEQ--------VMNEVKLLSSVSHPNLVRLLGCCIENGEQILVYEF
Grape      WVAIKKIRNRDNDSIEQ--------VMNEIKLISSVNHPNLVRLLGCCIENGEQILVYEF
Poplar     LVAIKKIKQRDTDSLDL--------VMNEIKLLSSVSHPNLVRLLGCCLEEGEPILVYEF
WAKL14     WVAIKRLRHRDSESLDQ--------VMNEIKLLSSVSHPNLVRLLGCCIEQGDPVLVYEY
WAKL21     CVAIKRLKHKDTTSIDQ--------VVNEIKLLSSVSHPNLVRLLGCCFADGEPFLVYEF
Rice       LVAVKRIKQRDNAGLDR--------VMNEVKLVSSVSHRNLVRLLGCCIEHGQQILVYEF
Zea mays   LVAIKRLRRRHHHDEDEDAAAEAALLLNEIKLISSVSHPNLVRLLGCCLDGGEQVLVYEY
             **:*::::.:.           . :   ::**:**:***.* *********:    *:  .****:

Tomato     MPNGTLAQHLQRE-----RSSG-LPWTIRLTIATETAHAIAHLHSAMNPPIYHRDIKSSNI
Grape      MANGTLSQHLQKE-----RGKG-LPWTTRLNIATETANAIAHLHSAITPPIFHRDIKSSNI
Poplar     MPNGTLCQHLQRE-----RGNG-LPWTVRLTVAAETANAIAYLHSVVNPPIYHRDIKSSNI
WAKL14     MPNGTLSEHLQRD-----RGSG-LPWTLRLTVATQTAKAIAYLHSSMNPPIYHRDIKSTNI
WAKL21     MPNGTLYQHLQHE-----RGQPPLSWQLRLAIACQTANAIAHLHSSVNPPIYHRDIKSSNI
Rice       MPNGTLAQHLQRE-----RGPA-VPWTVRLRIAVETAKAIAYLHSEVHPPIYHRDIKSSNI
Zea mays   VPNGTLSQHLHSAGASTGGRGALTWRARLGVAVETAGAIAHLHG-MRPPIFHRDVKSSNI
            :.**** :**:         . :.* ** :* :** ***:**.  :  ***:***:**:**

Tomato     LLDYNFNSKVADFGLSRFGMT---DDSHISTAPQGTPGYVDPQYHQNYHLSDKSDVYSFG
Grape      LLDDNFNSKVADFGLSRLGMT---ESSHISTAPQGTPGYLDPQYHQNFHLSDKSDVYSFG
Poplar     LLDYNYRSKVADFGLSRLGME---ESSHISTAPQGTPGYLDPQYHQYFHLSDKSDVYSFG
WAKL14     LLDYDFNSKVADFGLSRLGMT---ESSHISTAPQGTPGYLDPQYHQCFHLSDKSDVYSFG
WAKL21     LLDHEFNSKISDFGLSRLGMSTDFEASHISTAPQGTPGYLDPQYHQDFQLSDKSDVYSFG
Rice       LLDHEYNSKVADFGLSRMGMTS-VDSSHISTAPQGTPGYVDPQYHQNFHLSDKSDVYSFG
Zea mays   LLDATLRPKLADFGLSRAVDRLEAARSHVSTAPQGTPGYVDPEYHQNFHLSDKSDVYSFG
           ***      ..*::******          **:**********:**:***  ::***********

Tomato     VVLVEIITAMKVVDFSRSHSEINLAALAIDRIGKGRVDEIIDPFLEPHRDAWTLSSVHRV
Grape      VVLVEIISAMKVVDFSRPHSEVNLAALAIDRIGRGCVDEIIDPFLEPQRDAWTLCSIHKV
Poplar     VVLVEIITAQKVVDFSRPHSEVNLAALAIDRIGRGCVDEIVDPYLDPDRDAWTLSSIHSV
WAKL14     VVLAEIITGLKVVDFTRPHTEINLAALAVDKIGSGCIDEIIDPILDLDLDAWTLSSIHTV
WAKL21     VVLVEIISGFKVIDFTRPYSEVNLASLAVDRIGRGRVVDIIDPCLNKEINPKMFASIHNL
Rice       VVLVEIITAMKAVDFSRVGSEVNLAQLAVDRIGKGSLDDIVDPYLDPHRDAWTLTSIHKV
Zea mays   VVLLELVTAMKVVDFDRPPAEVNLASLALDRIGKGQVAEIVDPALLGAGEDWVMGSVRHV
           *** *::::. *.:** *  :*:*** **:*:**  * ;  :*:** *    : :  : *:: :

Tomato     AELAFRCLAFHRDMRPSMTEVADELEQIRLSSWASLEDXVCMTSSVNSSCSSPRRRSETS
Grape      AELAFRCLAFHRDMRPSMMEVADELEHWMGSNGG---EYMCGIISGIFFEMSLG--------
Poplar     AELAFRCLAFHRDMRPTMMEVAEELEQIRLSAWVPTMHMASPSSSSHFSDHGSQKSLG--
WAKL14     AELAFRCLAFHSDMRPTMTEVADELEQIRLSGWIPSMSLDSPAGSLRSSDRGSER-----
WAKL21     AELAFRCLSFHRNMRPTMVEITEDLHRIKLMHYG--------------------------
Rice       AELAFRCLAFHSEMRPSMAEVADELEQIQVSGWAPSTDDATFMSTTSSLCSSAPSR----
Zea mays   SELAFRCLAFQKDVRPSMREVAAELQRIRSAAPDGADPEEPAGSRLR-------------
           :********:*:  ::**:* *:: :*.:
```

FIGURE 7B

```
Tomato     FLCSTTKKGVGSRRLIVPLPLENSLALVEEIKNSSPVSVQDPGLSEESPPSPNRLLGNSG
Grape      -CMSVRKAGIGSRRLFVPHRPTDCLASMEEIKDSSPVSVHDPWLSEQSSPSTNSLLGNVV
Poplar     -VSVGKKAAVASRRLLVPQR-TDSLTSLEEVKDSSPVSVQDPWLSEQSSPSTNSLLDNVV
WAKL14     ---SVKQSSIGSRRVVIPQKQPDCLASVEEISDSSPISVQDPWLSAQSSPSTNTLLGNIP
WAKL21     ------------------------TESGKFKNRSEIDMK----RQQSFPRE--------
Rice       --CTDKSWGTAKSKRQAAANAVVKQETTKCAVADSPVSVQERWFSDRSSPSSNSLLRNSS
Zea_mays   ---PVSMMDIQIDVSLGGPDTAAKKAASPAKKAASPVSVQEVWVSDRSSPSTNGSMPRFA
                                   * :.::          .* *

Tomato     R-
Grape      Q-
Poplar     H-
WAKL14     R-
WAKL21     --
Rice       LN
Zea_mays   A-
```

FIGURE 7C

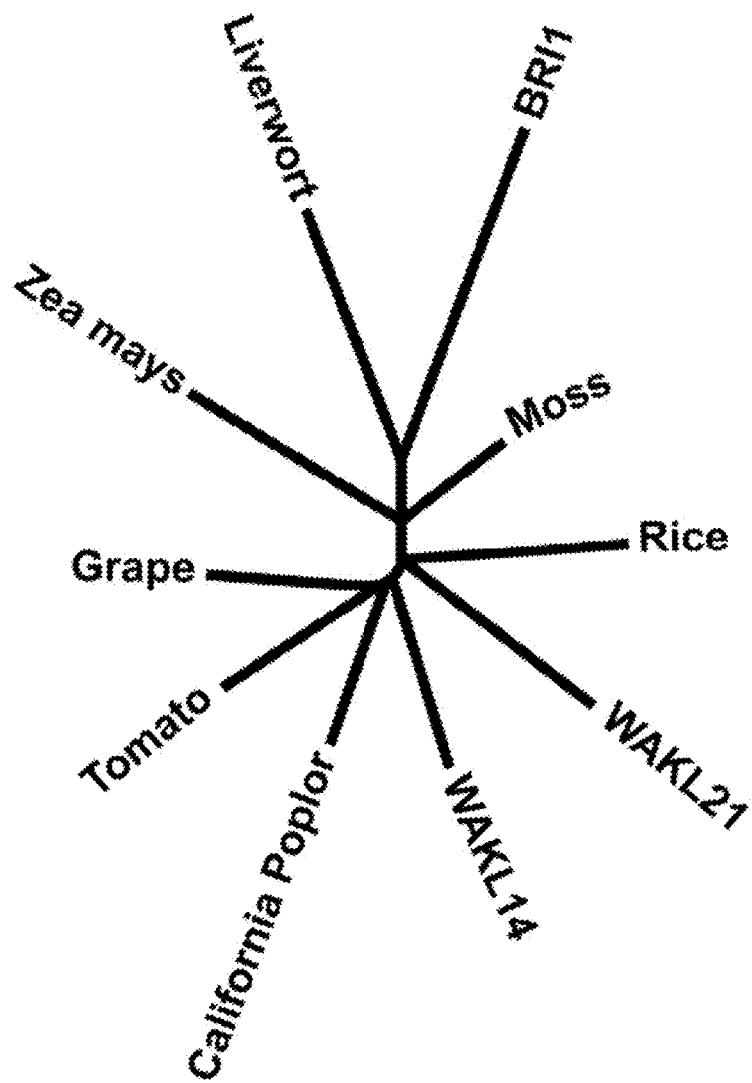

FIGURE 8

WALL-ASSOCIATED KINASE-LIKE POLYPEPTIDE MEDIATES NUTRITIONAL STATUS PERCEPTION AND RESPONSE

CROSS REFERENCE TO RELATED APPLICATIONS

This application claims priority under 35 U.S.C. §119 from Provisional Application Ser. No. 61/117,421, filed Nov. 24, 2008, the disclosure of which is incorporated herein by reference.

STATEMENT REGARDING FEDERALLY SPONSORED RESEARCH

The invention was supported by a grant no. DE-FG02-04ER15555 from U.S. Department of Energy. The government has certain rights in the invention.

TECHNICAL FIELD

The disclosure relates to methods for modulating plant growth and organogenesis using dominant-negative receptor-like kinases.

BACKGROUND

Receptor-like kinases (RLKs) form a large monophyletic gene family of approximately 600 members in plants (Shiu and Bleecker, 2001). They consist of proteins that contain a single extracellular domain that is thought to be the site of ligand binding, connected to a single kinase domain, via a single transmembrane domain. Upon ligand binding the kinase domain is capable of generating a phosphorylation signaling cascade. Because of the sheer size of this gene family and of the potential functional redundancy among closely related gene family members, not much is known about the function of many of these important signaling genes. What little that was known shows that RLKs have many diverse roles in plants such as, hormone perception, plant defense, plant development and cell growth.

SUMMARY

The disclosure provides a method for increasing plant yield relative to corresponding wild type plants comprising modulating expression in a plant of a nucleic acid encoding WAKL14 polypeptide or homologue thereof, and selecting for plants having increased yield or growth on a nutrient deficient substrate. In one embodiment, the modulated expression is effected by introducing a genetic modification in the locus of a gene encoding a WAKL14 polypeptide or a homologue thereof.

The disclosure also provides a method for increasing plant yield relative to corresponding wild type plants in a nutrient deficient or light deficient environment comprising introducing and expressing in a plant a WAKL14 nucleic acid or a variant thereof. In one embodiment, the variant is a sequence capable of hybridizing to a WAKL14 nucleic acid, which hybridizing sequence encodes a polypeptide comprising a polypeptide having an RLK domain structure. In another embodiment, the WAKL14 nucleic acid or variant thereof is overexpressed in a plant. In yet another embodiment, WAKL14 nucleic acid or variant thereof is of plant origin. In yet another embodiment, the WAKL14 nucleic acid sequence or variant thereof is from a monocotyledonous plant. In one embodiment, the variant encodes an orthologue or paralogue of the WAKL14 protein of SEQ ID NO: 1-4 or 5. In a further embodiment, the WAKL14 nucleic acid or variant thereof is operably linked to a constitutive promoter. In another embodiment, the transgenic plant grows better under abiotic stress conditions such as reduced nutrient availability or light.

The disclosure further provides a transgenic plant obtained by the methods described above and elsewhere herein wherein the plant comprises improved growth characteristics during nutrient or light deficiency compared to a wild-type plant. In one embodiment, the transgenic plant comprises a heterologous WAKL14 polynucleotide. In another embodiment, the transgenic plant comprises a heterologous promoter associated with a native WAKL14 to increase production of a WAKL14 polypeptide. In another aspect, the disclosure includes plant part, or plant cell obtained from the transgenic plants of the disclosure.

The disclosure also provides a construct comprising: (i) a WAKL14 nucleic acid or variant thereof (ii) one or more control sequences capable of driving expression of the nucleic acid sequence of (i), and optionally (iii) a transcription termination sequence.

The disclosure provides a method for the production of a transgenic plant having increased yield relative to a corresponding wild type plant, which method comprises: (i) introducing and expressing in a plant or plant cell a WAKL14 nucleic acid or variant thereof; and (ii) cultivating the plant cell under conditions for promoting plant growth and development.

The disclosure provides a transgenic plant having increased yield relative to a corresponding wild type plant under nutrient or light deficient conditions, said increased yield resulting from a WAKL14 nucleic acid or a variant thereof introduced into said plant.

The disclosure provides a method for increasing plant yield relative to corresponding wild type plants comprising modulating expression in a plant of a nucleic acid encoding WAKL14 polypeptide, variants or homolog thereof, and selecting for plants having increased yield or growth on a nutrient deficient substrate. In one embodiment, the modulated expression is effected by introducing a genetic modification in the locus of a gene encoding a WAKL14 polypeptide or a homolog thereof. In yet another embodiment, the method comprises introducing and expressing in a plant a WAKL polynucleotide, homolog or a variant thereof. In one embodiment, the variant lacks an extracellular domain. In yet another embodiment, the variant is a sequence capable of hybridizing to a WAKL polynucleotide, which hybridizing sequence encodes a polypeptide comprising a polypeptide having an RLK domain structure. In one embodiment, the WAKL polynucleotide, homolog or a variant thereof is overexpressed in a plant. In yet a further embodiment, the WAKL polynucleotide, homolog or a variant thereof comprises a sequence that is at least 40% identical to a sequence as set forth in SEQ ID NO:1, 3, 5, 7, 9, 11, 13, 15, or 17 and which encodes a polypeptide that upon overexpression in a plant produces tolerance to nitrogen and/or sucrose deficient growth media. In yet another embodiment, the WAKL polynucleotide, homolog or a variant thereof comprises a sequence comprising SEQ ID NO:1. In one embodiment, the WAKL polynucleotide, homolog or a variant thereof comprises a sequence selected from the group consisting of SEQ ID NO:1, 3, 5, 7, 9, 11, 13, 15, and 17. In yet a further embodiment, the WAKL polynucleotide, homolog or a variant thereof is operably linked to a constitutive promoter. In certain embodiment, the increased yield occurs under abiotic stress such as, but not limited to, reduced nutrient availability. In one embodiment, the reduced nutrient availability is reduced nitrogen availability.

The disclosure also provides a plant, plant part or plant cell obtained by the methods above.

The disclosure provides a transgenic plant produced by the method of claim 1 or 3, wherein the transgenic plant overexpresses a WAKL14 polynucleotide or homolog thereof and wherein the transgenic plant comprises improved growth on a nutrient deficient media.

The disclosure also provides a construct comprising: (i) a WAKL14 polynucleotide, homolog or a variant thereof, (ii) one or more control sequences capable of driving expression of the WAKL14 polynucleotide, homolog or a variant of (i), and optionally (iii) a transcription termination sequence. In one embodiment, the regulatory or control sequence is a constitutive promoter. In yet a further embodiment, the WAKL polynucleotide, homolog or a variant thereof comprises a sequence that is at least 40% identical to a sequence as set forth in SEQ ID NO:1, 3, 5, 7, 9, 11, 13, 15, or 17 and which encodes a polypeptide that upon overexpression in a plant produces tolerance to nitrogen and/or sucrose deficient growth media. In yet another embodiment, the WAKL polynucleotide, homolog or a variant thereof comprises a sequence comprising SEQ ID NO:1. In one embodiment, the WAKL polynucleotide, homolog or a variant thereof comprises a sequence selected from the group consisting of SEQ ID NO:1, 3, 5, 7, 9, 11, 13, 15, and 17.

The disclosure provides a plant cell transformed with a construct as described above.

The disclosure also provides a method for the production of a transgenic plant having increased yield or growth relative to a corresponding wild type plant on a nutrient deficient media, which method comprises: (i) introducing and expressing in a plant or plant cell a WAKL14 polynucleotide, homolog or a variant thereof; and (ii) cultivating the plant cell under conditions for promoting plant growth and development. In yet a further embodiment, the WAKL polynucleotide, homolog or a variant thereof comprises a sequence that is at least 40% identical to a sequence as set forth in SEQ ID NO:1, 3, 5, 7, 9, 11, 13, 15, or 17 and which encodes a polypeptide that upon overexpression in a plant produces tolerance to nitrogen and/or sucrose deficient growth media. In yet another embodiment, the WAKL polynucleotide, homolog or a variant thereof comprises a sequence comprising SEQ ID NO:1. In one embodiment, the WAKL polynucleotide, homolog or a variant thereof comprises a sequence selected from the group consisting of SEQ ID NO:1, 3, 5, 7, 9, 11, 13, 15, and 17.

The disclosure provides a transgenic plant having increased yield relative to a corresponding wild type plant under nutrient or light deficient conditions, said increased yield resulting from a WAKL14 polynucleotide, homolog or a variant thereof introduced into said plant. In yet a further embodiment, the WAKL polynucleotide, homolog or a variant thereof comprises a sequence that is at least 40% identical to a sequence as set forth in SEQ ID NO:1, 3, 5, 7, 9, 11, 13, 15, or 17 and which encodes a polypeptide that upon overexpression in a plant produces tolerance to nitrogen and/or sucrose deficient growth media. In yet another embodiment, the WAKL polynucleotide, homolog or a variant thereof comprises a sequence comprising SEQ ID NO:1. In one embodiment, the WAKL polynucleotide, homolog or a variant thereof comprises a sequence selected from the group consisting of SEQ ID NO:1, 3, 5, 7, 9, 11, 13, 15, and 17. The transgenic plant can be any plant type including, but not limited to, a monocotyledonous plant, selected from the group consisting of sugar cane, rice, maize, wheat, barley, millet, rye, oats, triticale, and sorghum.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 3 A-B shows primary root lengths of wild type, DN-WAKL14, 35S:WAKL14 and 35S:WAKL KIN mutants grown vertically under low light (45 μM photons s-1 m-2) and normal (150 μM photons s-1 m-2) at 3 DAG (A), and 6 DAG (B) on normal MS, sucrose deprived (-sucrose) MS media. Error bars represent the standard deviation (SD). Student's t-test: *=p<0.05 and +=p<0.001.

FIG. 4A-B shows WAKL14 mutant plants. (A) Six-day-after germination seedlings of wild type, DN-WAKL14 and 35S:WAKL14 mutants grown under low illumination (45 μM photons s-1 m-2) on normal MS and MS containing no nitrogen (-nitrogen). (B) Compiled data for the primary root lengths of 6 DAG wild type, DN-WAKL14 and 35S:WAKL14 grown on normal MS and -nitrogen MS. Error bars represent SD. Student's t-test: *=p<0.05.

FIG. 5A-C shows wild-type and mutant plants. (A) Twenty-one day old wild type, DN-WAKL14, WAKL14, and WAKL14 KIN soil grown plants grown under low illumination (45 μM photons s-1 m-2) with a 16 h light 8 h dark cycle. Under these conditions DN-WAKL14 exhibited stunted growth as well as pronounced leaf senescence. (B) Number of leaves for 21 day-old wild type, DN-WAKL14, WAKL14, and WAKL14 KIN soil grown plants. DN-WAKL14 had significantly less leaves then wild type while WAKL14, and WAKL14 KIN did not differ from the wild type significantly. (C) Plant diameter of 21 day-old wild type, DN-WAKL14, WAKL14, and WAKL14 KIN soil grown plants. DN-WAKL14 had significantly less leaves then wild type while WAKL14, and WAKL14 KIN did not differ from the wild type significantly. NIH Image was used for the calculation of plant diameter. Error bars represent SD. Student's t-test: +=p<0.01.

FIG. 7A-C shows a WAKL14 polypeptide sequence (SEQ ID NO:2) and homologs thereof (SEQ ID NOs: 4, 6, 8, 10, 12, and 18).

FIG. 8 shows an un-rooted Tree for WAKL14 and WAKL21 to WAKL genes from Liverwart, Moss, Corn, Rice, Poplar, Tomato and Grape (AtBRI1 gene used as Kinase domain homolog).

DETAILED DESCRIPTION

Figure 1:
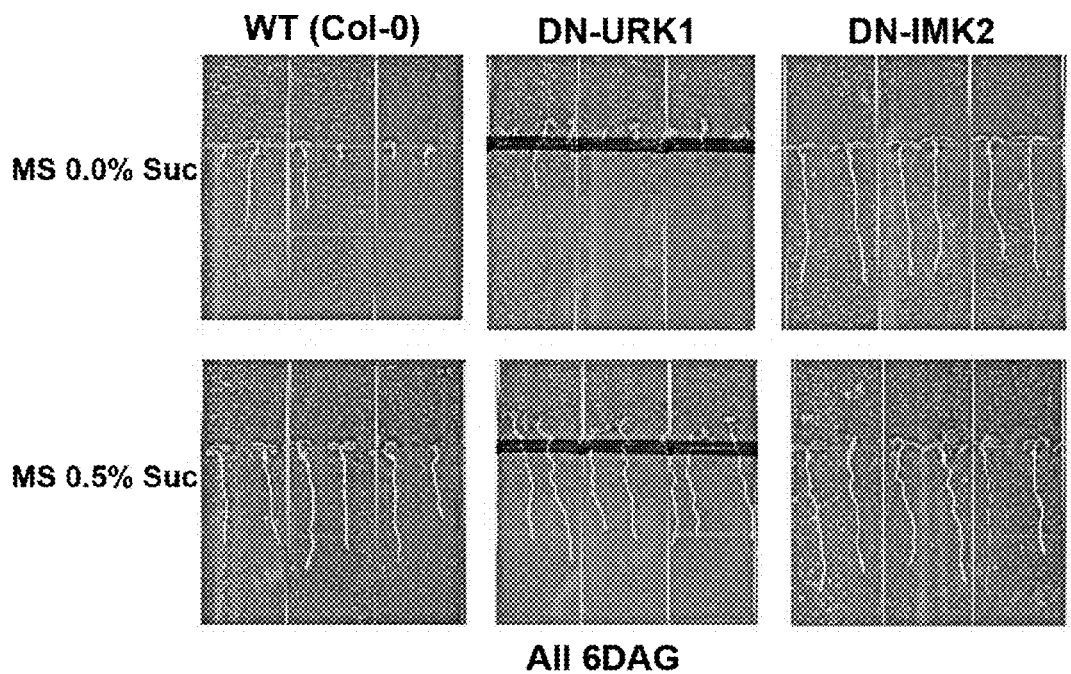
FIG. 1 show that six-day-after germination seedlings grown vertically on normal MS (0.5% sucrose) and reduced sucrose MS (0% sucrose) media. DN-RLK (DN-URK1) shows sensitivity to sucrose deprivation while DN-RLK (DN-IMK2) shows insensitivity to the same conditions. The wild type seedlings also show some sensitivity to sucrose deprivation.

As used herein and in the appended claims, the singular forms "a," "and," and "the" include plural referents unless the context clearly dictates otherwise. Thus, for example, reference to "a cell" includes a plurality of such cells and reference to "the gene" includes reference to one or more genes and equivalents thereof, and so forth.

Also, the use of "or" means "and/or" unless stated otherwise. Similarly, "comprise," "comprises," "comprising" "include," "includes," and "including" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of."

Unless defined otherwise, all technical and scientific terms used herein have the same meaning as commonly understood to one of ordinary skill in the art to which this disclosure belongs. Although any methods and reagents similar or equivalent to those described herein can be used in the practice of the disclosed methods and compositions, the exemplary methods and materials are now described.

All publications mentioned herein are incorporated herein by reference in full for the purpose of describing and disclosing the methodologies, which are described in the publications, which might be used in connection with the description herein. The publications discussed above and throughout the text are provided solely for their disclosure prior to the filing date of the present application. Nothing herein is to be construed as an admission that the inventors are not entitled to antedate such disclosure by virtue of prior disclosure.

Mechanisms that monitor the nutrient status of a plant are important for growth, development, and responses to the environment. Such mechanisms are presumably linked to nutrient uptake, mobilization and redistribution that are necessary to regulate plant vegetative growth and reproductive development. However, little is known about the molecular basis of nutrient sensing mechanisms in plants.

The regulated interaction of the source and sink to nutrients and photosynthate are necessary for the proper growth and development of plants. Under specific conditions, nutrients are mobilized from the source tissues (e.g., mature and senescing leaves) to the sink tissues (e.g., meristems, fruits, and storage tissues). Presumably mechanisms exist for plants to sense sink signals and transmit the signals to the source tissues. It was therefore possible that a receptor mediated system played a crucial role in the perception and transduction of these signals. The superfamily of receptor-like kinases (RLKs) in Arabidopsis contains over 600 RLK homologs, which is nearly 0.25% of gene content (Shiu and Bleecker, 2001). The enormity of this family and the fact that most of these genes have no known function makes it an attractive repository for genes involved in environmental responses including nutrient status sensing (Kohorn et al., 2006).

There are over 400 receptor-like kinases (RLKs) in Arabidopsis that have predicted transmembrane domains and extracellular domains larger than 100 amino acids, for many of which the function is unknown or unclear. In order to better understand the functions of these RLKs the disclosure provides an approach whereby kinase-free versions of the RLKs (or the dominant negative: DN) were generated and overexpressed in Arabidopsis followed by determining a change in phenotypes. This approach works in two ways. One, the kinase free RLK may homo- or heterodimerize with the endogenous RLKs and the result would be a termination of the phosphorylation cascade, or secondly it could compete for and bind up ligand(s) that are required for signaling of the endogenous RLKs and again diminish any downstream signaling. To date, 100 kinase free RLK constructs have been generated and 72 of these stably transformed into Arabidopsis as homozygous lines. This covers over 63% of all the RLKs in kinase-free (DN) constructs and over 45% coverage in homozygous lines. These homozygous lines were then investigated for morphological, developmental and stress response phenotypes.

Many of the RLKs with known function are involved in defense response, development, hormone response and self-incompatibility. One of the major obstacles to studying the function of RLKs is that there are numerous a subfamilies providing potential for functional redundancy among members of the subfamily. The disclosure provides a dominant-negative approach for functional genomics analysis. The approach uses the amino acid similarity of the extracellular domains among sub-family members as a way to disrupt the function of the entire sub-family group. By overexpressing a construct containing only the extracellular domain and the transmembrane domain (the kinase domain is excluded) a diminished signaling through both ligand competition and inactive homo-heterodimerization is achieved. In this way the study of the function of an entire sub-family was obtained to more quickly find the functions of many RLKs, which is useful for such a large gene family.

Using the dominant negative mutant (DN)-based novel functional genomics approach to identify potential nutrient sensing molecules from the superfamily of receptor-like kinases (RLKs) of Arabidopsis thaliana the disclosure provides genes that regulate nutrient status. A library of dominant negative RLK expressing lines and screened them for changes in nutrient responses. In this screen of 42 DN-RLKs tested, 20 exhibited shorter roots on sucrose-deprived media. Of these twenty, 11 also exhibited shorter roots on MS media. Seven DN-RLKs were found to increase root growth on sucrose-deprived media. DN-IMK2 was found to cause insensitivity to increased (6%) sucrose.

A member of the family of RLKs called wall-associated kinase-like (WAKLs) genes, WAKL4, has been shown to be involved in mineral responses and WAKs have been shown to directly bind the cell wall, opening up the possibility of signaling from the apoplast to the cell, controlling nutrient sensing.

Arabidopsis DN-RLK transgenic knockout lines were grown on a MS agar medium lacking sucrose to identify four RLK genes that affect sucrose sensing from 42 DN-RLK constructs. In the absence of sucrose, wild type Arabidopsis seedlings exhibited greatly reduced root elongation compared to those supplemented with 0.5% sucrose. The DN-DUF26 (At4g23290) and DN-WAKL14 (At2g23450) knockouts showed exaggerated root growth reduction, whereas DN mutants of two LRRIII genes (At5g10020 and At3g08680) increased root elongation. To investigate the mechanisms by which these RLKs affect Arabidopsis responses to sucrose depletion, focus was placed on WAKL14 for more in-depth analysis by using transgenic lines overexpressing full-length wild type WAKL14 (35S:WAKL14) and a extracellular domain deletion mutant containing only the transmembrane and kinase domains (35S:WAKL14 KIN; i.e., lacking the extracellular domain). Both 35S:WAKL14 and 35S: WAKL14 KIN seedlings performed better than wild type in the absence of sucrose. Preliminary studies suggest that WAKL14 is also involved in the promotion of seedling growth when nitrogen is limiting. Under low light conditions, 35S:WAKL14 adult plants grew better than WT, whereas DN-WAKL14 adult plants exhibited stunted growth and senesced before bolting. Quantitative RT-PCR analysis showed that DN-WAKL14 increased the expression of senescence-related genes (e.g., SRG2/DIN; At3g60140), but 35S: WAKL14 had an opposite effect. These results demonstrate that WAKL14 plays an important positive role in the regulation of nutrient status in plants most likely through its potential role in sensing nutrient status.

The disclosure provides transgenic plants that overexpress a WAKL14 polynucleotide or polypeptide or homolog thereof. The disclosure also provides a transgenic plant that expresses an agonistic polypeptide (e.g., a mutant WALK14 polypeptide or homolog thereof) that causes increased growth under low light. In one embodiment, the mutant WALK14 polypeptide or homolog thereof lacks a functional extracellular domain.

As used herein a wall-associated kinase like polypeptide refers to a polypeptide comprising a sequence that has at least 40%, at least 50%, at least 60%, at least 70%, at least 80%, at least 85%, at least 90%, at least 95%, at least 98%, or at least 99% identity to SEQ ID NO:2, wherein the polypeptide promotes plant growth on a nutrient deficient media. In one embodiment, the wall-associated kinase like (WAKL) polypeptide comprises a homolog of an *Arabidopsis thaliana* WAKL polypeptide such as, for example, a WAKL14 polypeptide (e.g., SEQ ID NO:2). In one embodiment, the WAKL homolog comprises a sequence that is at least 40%, at least 50%, at least 60%, at least 70%, at least 80%, at least 85%, at least 90%, at least 95%, at least 98%, or at least 99% to a sequence selected from the group consisting of SEQ ID NO:4, 6, 8, 10, 12, 14 and 16, wherein the polypeptide improves plant growth in a nutrient deficient media.

A wall-associated kinase like polypeptide comprises a sequence as set forth in any of SEQ ID NOs: 1, 4, 6, 8, 10, 12, 14, or 16 and homologs and variants thereof. Variant wall-associated kinase like polypeptide comprise at least 80% identity, 85% identity, 90% identity, 95% identity, 98% identity or 99% identity to a sequence set forth in SEQ ID NO:2, 4, 6, 8, 10, 12, 14 or 16. This include variants having from 1-50 (e.g., 1-40, 1-30, 1-20, or 1-10 conservative amino acid substitutions to a sequence as set forth in SEQ ID NO:2, 4, 6, 8, 10, 12, 14, or 16. Such conservative substitutions can be identified based upon the alignment set forth herein. Such variants when expressed in a plant provide the plant with tolerance in a nutrient deprived environment.

A wall-associated kinase like polynucleotide comprises a nucleic acid sequence comprising or consisting of a sequence encoding a polypeptide of SEQ ID NO:2, 4, 6, 8, 10, 12, 14, or 16, variants thereof and homologs thereof. In one embodiment, the polynucleotide comprises a sequence that is at least 40%, 50%, 60%, 70%, 80%, 90%, 95%, 98%, 99% or 100% identical to a sequence as set forth in SEQ ID NO: 1, 3, 5, 7, 9, 11, 13, or 15 so long as the polynucleotide encodes a polypeptide having a WALK14 protein activity (e.g., the ability to promote growth and survival on a nutrient deprived media).

Polynucleotides encoding the polypeptides and variants thereof can be cloned into a suitable expression vector and expressed in a host cell. Transgenic plants comprising a heterologous polynucleotide causing overexpression of a WALK14 polypeptide or expression of a mutant or variant WALK14 polypeptide can be used to generate plants capable of growing on reduced nutrient medium or under reduced light conditions.

For example, overexpression of a WAKL polypeptide of the disclosure can provide a plant with tolerance to sucrose and/or nitrogen deprivation. The disclosure demonstrates that WAKL14 overexpression provides such tolerance. WAKL14 was investigated because it exhibited increased sucrose sensitivity as well as a leaf senescence phenotype in the T2 generation in a DN phenotype. Both full length (35S: WAKL14) and kinase only overexpression (35S:WAKL14 KIN) lines were generated and evaluated to both sucrose and nitrogen deprivation. The DN-WAKL14 was hypersensitive to nutrient deprivation where both overexpression mutants had reduced sensitivity to both sucrose and nitrogen depletion. These findings demonstrate a role of WAKL14 in nutrient sensing.

To further investigate WAKL14s role in nutrient sensing and to examine the observed senescence phenotype the senescence gene expression in DN-WAKL14 and 35S:WAKL14 were examined and found that senescence gene expression was greatly upregulated in DN-WAKL14 and down regulated in 35S:WAKL14 under elevated sucrose (3%) and in the dark compared to the wild type. These results show that WAKL14 acts as a nutrient sensor and co-ordinately regulates senescence gene expression. The disclosure shows that the dominant negative approach to investigating RLK function has merit because it has allowed identification of RLKs with previously unknown functions that affect nutrient signaling in plants.

As used herein, the terms "host cells" and "recombinant host cells" are used interchangeably and refer to cells (for example, plant cells) into which the compositions of the presently disclosed subject matter (for example, an expression vector comprising aa wall associated kinase-like (WAKL) polynucleotide or homolog thereof) can be introduced. Furthermore, the terms refer not only to the particular plant cell into which an expression construct is initially introduced, but also to the progeny or potential progeny of such a cell. Because certain modifications can occur in succeeding generations due to either mutation or environmental influences, such progeny might not, in fact, be identical to the parent cell, but are still included within the scope of the term as used herein.

As used herein, the terms "complementarity" and "complementary" refer to a nucleic acid that can form one or more hydrogen bonds with another nucleic acid sequence by either traditional Watson-Crick or other non-traditional types of interactions. In reference to the nucleic molecules of the presently disclosed subject matter, the binding free energy for a nucleic acid molecule with its complementary sequence is sufficient to allow the relevant function of the nucleic acid to proceed, in some embodiments, ribonuclease activity. Determination of binding free energies for nucleic acid molecules is well known in the art. See e.g., Freier et al., 1986; Turner et al., 1987.

A "dominant negative RLK" refers to a polypeptide variant of a native RLK sequence whose expression interferes with or otherwise counteracts native RLK activity. Dominant negative RLK mutants can include a fragment of a RLK polypeptide sequence with at least one mutation. Exemplary mutations include, e.g., RLK polypeptide lacking a functional domain. In some embodiments, the dominant negative RLK comprise a polypeptide at least 50%, 60%, 70%, 80%, or 90% identical to a wild-type RLK.

Polynucleotides useful in the methods of the disclosure include naturally occurring polynucleotides, recombinant polynucleotides and chemically synthesized polynucleotides. There is no particular limitation on the type of polynucleotides of the disclosure so long as they are capable of encoding polypeptides useful for modulating growth of a plant or plant cell on a nutrient deficient media (e.g., a sucrose and/or nitrogen deficient) and include genomic DNA, cDNA, chemically synthesized DNA, and the like. Genomic DNAs may be prepared by conducting PCR (Saiki et al., Science, 1988, 239, 487) using as a template genomic DNA prepared according to a method described in literature (Rogers and Bendich, Plant Mol. Biol., 1985, 5, 69) and primers prepared based on a nucleotide sequence of a polynucleotide of the disclosure (e.g. a nucleotide sequence set forth in SEQ ID NO:1, 3, 5, 7, 9, 11, 13, or 15). Furthermore, cDNA may be prepared according to the standard method (Maniatis et al., "Molecular Cloning", Cold Spring Harbor Laboratory Press), by preparing mRNA from plants, performing reverse transcription, and conducting PCR using primers similar to those described above. Genomic DNA and cDNA may also be prepared by constructing a genomic DNA library or a cDNA library according to the standard method, and screening this library using a probe, for example, one synthesized based on the a nucleotide sequence of a DNA of the disclosure. The DNA thus obtained may be easily sequenced using, for example, the "Sequencer Model 373" (ABI).

As used herein, the terms "complementarity" and "complementary" refer to a nucleic acid that can form one or more hydrogen bonds with another nucleic acid sequence by either traditional Watson-Crick or other non-traditional types of interactions. In reference to the nucleic molecules of the presently disclosed subject matter, the binding free energy for a nucleic acid molecule with its complementary sequence is sufficient to allow the relevant function of the nucleic acid to proceed, in some embodiments, ribonuclease activity. Determination of binding free energies for nucleic acid molecules is well known in the art. See e.g., Freier et al., 1986; Turner et al., 1987.

As used herein, the phrase "percent complementarity" refers to the percentage of contiguous residues in a nucleic acid molecule that can form hydrogen bonds (e.g., Watson-Crick base pairing) with a second nucleic acid sequence (e.g., 5, 6, 7, 8, 9, 10 out of 10 being 50%, 60%, 70%, 80%, 90%, and 100% complementary). The terms "100% complementary", "fully complementary", and "perfectly complementary" indicate that all of the contiguous residues of a nucleic acid sequence can hydrogen bond with the same number of contiguous residues in a second nucleic acid sequence.

As used herein, the term "gene" refers to a nucleic acid sequence that encodes an RNA. The term "gene" also refers broadly to any segment of DNA associated with a biological function. As such, the term "gene" encompasses sequences including, but not limited to, a coding sequence, a promoter region, a transcriptional regulatory sequence, a non-expressed DNA segment that is a specific recognition sequence for regulatory proteins, a non-expressed DNA segment that contributes to gene expression, a DNA segment designed to have desired parameters, or combinations thereof. A gene can be obtained by a variety of methods, including cloning from a biological sample, synthesis based on known or predicted sequence information, and recombinant derivation from one or more existing sequences.

As is understood in the art, a gene typically comprises a coding strand and a non-coding strand. As used herein, the terms "coding strand" and "sense strand" are used interchangeably, and refer to a nucleic acid sequence that has the same sequence of nucleotides as an mRNA from which the gene product is translated. As is also understood in the art, when the coding strand and/or sense strand is used to refer to a DNA molecule, the coding/sense strand includes thymidine residues instead of the uridine residues found in the corresponding mRNA. Additionally, when used to refer to a DNA molecule, the coding/sense strand can also include additional elements not found in the mRNA including, but not limited to promoters, enhancers, and introns. Similarly, the terms "template strand" and "antisense strand" are used interchangeably and refer to a nucleic acid sequence that is complementary to the coding/sense strand.

The phrase "gene expression" generally refers to the cellular processes by which a biologically active polypeptide is produced from a DNA sequence and exhibits a biological activity in a cell. As such, gene expression involves the processes of transcription and translation, but also involves post-transcriptional and post-translational processes that can influence a biological activity of a gene or gene product. These processes include, but are not limited to RNA syntheses, processing, and transport, as well as polypeptide synthesis, transport, and post-translational modification of polypeptides. Additionally, processes that affect protein-protein interactions within the cell can also affect gene expression as defined herein.

The terms "heterologous gene", "heterologous DNA sequence", "heterologous nucleotide sequence", "exogenous nucleic acid molecule", "exogenous DNA segment", and "transgene" as used herein refer to a sequence that originates from a source foreign to an intended host cell or, if from the same source, is modified from its original form. Thus, a heterologous gene in a host cell includes a gene that is endogenous to the particular host cell but has been modified, for example by mutagenesis or by isolation from native transcriptional regulatory sequences. The terms also include non-naturally occurring multiple copies of a naturally occurring nucleotide sequence. Thus, the terms refer to a DNA segment that is foreign or heterologous to the cell, or homologous to the cell but in a position within the host cell nucleic acid wherein the element is not ordinarily found. A transgenic plant or host cell can comprise, for example, a heterologous promoter that promotes transcription of a wall-associated kinase-like polynucleotide, including homologs and variant (e.g., a WAKL14, WAKL14 homolog or variant) thereof in a desired plant cell or host cell.

As used herein, the term "isolated" refers to a molecule substantially free of other nucleic acids, proteins, lipids, carbohydrates, and/or other materials with which it is normally associated, such association being either in cellular material or in a synthesis medium. Thus, the term "isolated polynucleotide" or "isolated nucleic acid" refers to a ribonucleic acid molecule or a deoxyribonucleic acid molecule (for example, a genomic DNA, cDNA, mRNA, and the like) of natural or synthetic origin or some combination thereof, which (1) is not associated with the cell in which the "isolated polynucleotide" is found in nature, or (2) is operatively linked to a polynucleotide to which it is not linked in nature. Similarly, the term "isolated polypeptide" refers to a polypeptide, in some embodiments prepared from recombinant DNA or RNA, or of synthetic origin, or some combination thereof, which (1) is not associated with proteins that it is normally found with in nature, (2) is isolated from the cell in which it normally occurs, (3) is isolated free of other proteins from the same cellular source, (4) is expressed by a cell from a different species, or (5) does not occur in nature.

The term "isolated", when used in the context of an "isolated cell", refers to a cell that has been removed from its natural environment, for example, as a part of an organ, tissue, or organism.

As used herein, the term "modulate" refers to an increase, decrease, or other alteration of any, or all, chemical and biological activities or properties of a biochemical entity, e.g., a wild type or mutant nucleic acid molecule. For example, the term "modulate" can refer to a change in the expression level of a gene or a level of an RNA molecule or equivalent RNA molecules encoding one or more proteins or protein subunits; or to an activity of one or more proteins or protein subunits that is upregulated or downregulated, such that expression, level, or activity is greater than or less than that observed in the absence of the modulator. For example, the term "modulate" can mean "increasing" or "promoting", but the use of the word "modulate" is not limited to this definition.

The term "naturally occurring", as applied to an object, refers to the fact that an object can be found in nature. For example, a polypeptide or polynucleotide sequence that is present in an organism (including bacteria) that can be isolated from a source in nature and which has not been intentionally modified by man in the laboratory is naturally occurring. It must be understood, however, that any manipulation by the hand of man can render a "naturally occurring" object an "isolated" object as that term is used herein.

As used herein, the terms "polynucleotide" or "nucleic acid molecule" refer to any of deoxyribonucleic acid (DNA), ribonucleic acid (RNA), oligonucleotides, fragments generated by the polymerase chain reaction (PCR), and fragments generated by any of ligation, scission, endonuclease action, and exonuclease action. Nucleic acids can be composed of monomers that are naturally occurring nucleotides (such as deoxyribonucleotides and ribonucleotides), or analogs of naturally occurring nucleotides (e.g., alpha-enantiomeric forms of naturally occurring nucleotides), or a combination of both. Modified nucleotides can have modifications in sugar moieties and/or in pyrimidine or purine base moieties. Sugar modifications include, for example, replacement of one or more hydroxyl groups with halogens, alkyl groups, amines, and azido groups, or sugars can be functionalized as ethers or esters. Moreover, the entire sugar moiety can be replaced with sterically and electronically similar structures, such as aza-sugars and carbocyclic sugar analogs. Examples of modifications in a base moiety include alkylated purines and pyrimidines, acylated purines or pyrimidines, or other well-known heterocyclic substitutes. Nucleic acid monomers can be linked by phosphodiester bonds or analogs of such linkages. Analogs of phosphodiester linkages include phosphorothioate, phosphorodithioate, phosphoroselenoate, phosphorodiselenoate, phosphoroanilothioate, phosphoranilidate, phosphoramidate, and the like. The term also includes so-called "peptide nucleic acids", which comprise naturally occurring or modified nucleic acid bases attached to a polyamide backbone. Nucleic acids can be either single stranded or double stranded.

The terms "operably linked" and "operatively linked" are used interchangeably. When describing the relationship between two nucleic acid regions, each term refers to a juxtaposition wherein the regions are in a relationship permitting them to function in their intended manner. For example, a control sequence "operably linked" to a coding sequence can be ligated in such a way that expression of the coding sequence is achieved under conditions compatible with the control sequences, such as when the appropriate molecules (e.g., inducers and polymerases) are bound to the control or regulatory sequence(s). Thus, in some embodiments, the phrase "operably linked" refers to a promoter connected to a coding sequence in such a way that the transcription of that coding sequence is controlled and regulated by that promoter. Techniques for operably linking a promoter to a coding sequence are well known in the art; the precise orientation and location relative to a coding sequence of interest is dependent, inter alia, upon the specific nature of the promoter.

Thus, the term "operably linked" can refer to a promoter region that is connected to a nucleic acid sequence in such a way that the transcription of that nucleic acid sequence is controlled and regulated by that promoter region. Similarly, a nucleic acid sequence is said to be under the "transcriptional control" of a promoter to which it is operably linked. Techniques for operably linking a promoter region to a nucleotide sequence are known in the art. In some embodiments, a nucleotide sequence comprises a coding sequence and/or an open reading frame. The term "operably linked" can also refer to a transcription termination sequence that is connected to a nucleotide sequence in such a way that termination of transcription of that nucleotide sequence is controlled by that transcription termination sequence. For example, the disclosure provides vectors and host cells comprising a WAKL such as WAKL14 (or homolog thereof) polynucleotide operably linked to a promoter for expression (e.g., overexpression) of the polynucleotide in the plant or cell.

In some embodiments, more than one of these elements can be operably linked in a single molecule. Thus, in some embodiments multiple terminators, coding sequences, and promoters can be operably linked together. Techniques are known to one of ordinary skill in the art that would allow for the generation of nucleic acid molecules that comprise different combinations of coding sequences and/or regulatory elements that would function to allow for the expression of one or more nucleic acid sequences in a cell.

The term "regulatory sequence" is a generic term used throughout the specification to refer to polynucleotide sequences, such as initiation signals, enhancers, regulators, promoters, and termination sequences, which are necessary or desirable to affect the expression of coding and non-coding sequences to which they are operatively linked. Exemplary regulatory sequences are described in Goeddel, 1990, and include, for example, the early and late promoters of simian virus 40 (SV40), adenovirus or cytomegalovirus immediate early promoter, the lac system, the trp system, the TAC or TRC system, T7 promoter whose expression is directed by T7 RNA polymerase, the major operator and promoter regions of phage lambda, the control regions for fd coat protein, the promoter for 3-phosphoglycerate kinase or other glycolytic enzymes, the promoters of acid phosphatase, e.g., Pho5, the promoters of the yeast a-mating factors, the polyhedron promoter of the baculovirus system and other sequences known to control the expression of genes of prokaryotic or eukaryotic cells or their viruses, and various combinations thereof. The nature and use of such control sequences can differ depending upon the host organism. In prokaryotes, such regulatory sequences generally include promoter, ribosomal binding site, and transcription termination sequences. The term "regulatory sequence" is intended to include, at a minimum, components the presence of which can influence expression, and can also include additional components the presence of which is advantageous, for example, leader sequences and fusion partner sequences.

In some embodiments, transcription of a polynucleotide sequence is under the control of a promoter sequence (or other regulatory sequence) that controls the expression of the polynucleotide in a cell-type in which expression is intended. It will also be understood that the polynucleotide can be under the control of regulatory sequences that are the same or different from those sequences which control expression of the naturally occurring form of the polynucleotide. As used herein, the phrase "functional derivative" refers to a subsequence of a promoter or other regulatory element that has substantially the same activity as the full length sequence from which it was derived. As such, a "functional derivative" of a seed-specific promoter can itself function as a seed-specific promoter.

Termination of transcription of a polynucleotide sequence is typically regulated by an operatively linked transcription termination sequence (for example, an RNA polymerase III termination sequence). In certain instances, transcriptional terminators are also responsible for correct mRNA polyadenylation. The 3' non-transcribed regulatory DNA sequence includes in some embodiments about 50 to about 1,000, and in some embodiments about 100 to about 1,000, nucleotide base pairs and contains plant transcriptional and translational termination sequences. Appropriate transcriptional terminators and those that are known to function in plants include the cauliflower mosaic virus (CaMV) 35S terminator, the tml terminator, the nopaline synthase terminator, the pea rbcS E9 terminator, the terminator for the T7 transcript from the octopine synthase gene of *Agrobacterium tumefaciens*, and the 3' end of the protease inhibitor I or II genes from potato or tomato, although other 3' elements known to those of skill in the art can also be employed. Alternatively, a gamma coixin, oleosin 3, or other terminator from the genus *Coix* can be used.

The term "promoter" or "promoter region" each refers to a nucleotide sequence within a gene that is positioned 5' to a coding sequence and functions to direct transcription of the coding sequence. The promoter region comprises a transcriptional start site, and can additionally include one or more transcriptional regulatory elements. In some embodiments, a method of the presently disclosed subject matter employs a RNA polymerase III promoter.

A "minimal promoter" is a nucleotide sequence that has the minimal elements required to enable basal level transcription to occur. As such, minimal promoters are not complete promoters but rather are subsequences of promoters that are capable of directing a basal level of transcription of a reporter construct in an experimental system. Minimal promoters are often augmented with one or more transcriptional regulatory elements to influence the transcription of an operatively linked gene. For example, cell-type-specific or tissue-specific transcriptional regulatory elements can be added to minimal promoters to create recombinant promoters that direct transcription of an operatively linked nucleotide sequence in a cell-type-specific or tissue-specific manner.

Different promoters have different combinations of transcriptional regulatory elements. Whether or not a gene is expressed in a cell is dependent on a combination of the particular transcriptional regulatory elements that make up the gene's promoter and the different transcription factors that are present within the nucleus of the cell. As such, promoters are often classified as "constitutive", "tissue-specific", "cell-type-specific", or "inducible", depending on their functional activities in vivo or in vitro. For example, a constitutive promoter is one that is capable of directing transcription of a gene in a variety of cell types (in some embodiments, in all cell types) of an organism. Exemplary constitutive promoters include the promoters for the following genes which encode certain constitutive or "housekeeping" functions: hypoxanthine phosphoribosyl transferase (HPRT), dihydrofolate reductase (DHFR; (Scharfmann et al., 1991), adenosine deaminase, phosphoglycerate kinase (PGK), pyruvate kinase, phosphoglycerate mutase, the beta-actin promoter (see e.g., Williams et al., 1993), and other constitutive promoters known to those of skill in the art. "Tissue-specific" or "cell-type-specific" promoters, on the other hand, direct transcription in some tissues or cell types of an organism but are inactive in some or all others tissues or cell types. Exemplary tissue-specific promoters include those promoters described in more detail hereinbelow, as well as other tissue-specific and cell-type specific promoters known to those of skill in the art. In some embodiments, a tissue-specific promoter is a seed-specific promoter, leaf specific, root specific promoter.

When used in the context of a promoter, the term "linked" as used herein refers to a physical proximity of promoter elements such that they function together to direct transcription of an operatively linked nucleotide sequence The term "transcriptional regulatory sequence" or "transcriptional regulatory element", as used herein, each refers to a nucleotide sequence within the promoter region that enables responsiveness to a regulatory transcription factor. Responsiveness can encompass a decrease or an increase in transcriptional output and is mediated by binding of the transcription factor to the DNA molecule comprising the transcriptional regulatory element. In some embodiments, a transcriptional regulatory sequence is a transcription termination sequence, alternatively referred to herein as a transcription termination signal.

Coding sequences intended for expression in transgenic plants can be first assembled in expression cassettes operably linked to a suitable promoter expressible in plants. The expression cassettes can also comprise any further sequences required or selected for the expression of the transgene. Such sequences include, but are not limited to, transcription terminators, extraneous sequences to enhance expression such as introns, vital sequences, and sequences intended for the targeting of the transgene-encoded product to specific organelles and cell compartments. These expression cassettes can then be easily transferred to the plant transformation vectors disclosed below. The following is a description of various components of typical expression cassettes.

The selection of the promoter used in expression cassettes can determine the spatial and temporal expression pattern of the transgene in the transgenic plant. Selected promoters can express transgenes in specific cell types (such as leaf epidermal cells, mesophyll cells, root cortex cells) or in specific tissues or organs (roots, leaves, flowers, or seeds, for example) and the selection can reflect the desired location for accumulation of the transgene. Alternatively, the selected promoter can drive expression of the gene under various inducing conditions. Promoters vary in their strength; i.e., their abilities to promote transcription. Depending upon the host cell system utilized, any one of a number of suitable promoters can be used, including the gene's native promoter. The following are non-limiting examples of promoters that can be used in expression cassettes.

Ubiquitin is a gene product known to accumulate in many cell types and its promoter has been cloned from several species for use in transgenic plants (e.g. sunflower-Binet et al., 1991; maize-Christensen & Quail, 1989; and *Arabidopsis*-Callis et al., 1990). The *Arabidopsis* ubiquitin promoter is suitable for use with the nucleotide sequences of the presently disclosed subject matter. The ubiquitin promoter is suitable for gene expression in transgenic plants, both monocotyledons and dicotyledons. Suitable vectors are derivatives of pAHC25 or any of the transformation vectors disclosed herein, modified by the introduction of the appropriate ubiquitin promoter and/or intron sequences.

Construction of the plasmid pCGN1761 is disclosed in the published patent application EP 0 392 225, which is hereby incorporated by reference. pCGN1761 contains the "double" CaMV 35S promoter and the tml transcriptional terminator with a unique EcoRI site between the promoter and the terminator and has a pUC-type backbone. A derivative of pCGN1761 is constructed which has a modified polylinker that includes NotI and XhoI sites in addition to the existing EcoRI site. This derivative is designated pCGN1761 ENX. pCGN1761 ENX is useful for the cloning of cDNA sequences or coding sequences (including microbial ORF sequences) within its polylinker for the purpose of their expression under the control of the 35S promoter in transgenic plants. The entire 35S promoter-coding sequence-tml terminator cassette of such a construction can be excised by HindIII, SphI, SalI, and XbaI sites 5' to the promoter and XbaI, BamHI and BglI sites 3' to the terminator for transfer to transformation vectors such as those disclosed below. Furthermore, the double 35S promoter fragment can be removed by 5' excision with HindIII, SphI, SalI, XbaI, or PsfI, and 3' excision with any of the polylinker restriction sites (EcoRI, NotI or XhoI) for replacement with another promoter. If desired, modifications around the cloning sites can be made by the introduction of sequences that can enhance translation. This is particularly useful when overexpression is desired. For example, pCGN1761ENX can be modified by optimization of the translational initiation site as disclosed in U.S. Pat. No. 5,639,949, incorporated herein by reference.

Several isoforms of actin are known to be expressed in most cell types and consequently the actin promoter can be used as a constitutive promoter. In particular, the promoter from the rice Actl gene has been cloned and characterized (McElroy et al., 1990). A 1.3 kilobase (kb) fragment of the promoter was found to contain all the regulatory elements required for expression in rice protoplasts. Furthermore, expression vectors based on the Acti promoter have been constructed (McElroy et al., 1991). These incorporate the Actl-intron 1, Adhl 5' flanking sequence (from the maize alcohol dehydrogenase gene) and Adhl-intron 1 and sequence from the CaMV 35S promoter. Vectors showing highest expression were fusions of 35S and Actl intron or the Actl 5' flanking sequence and the Actl intron. Optimization of sequences around the initiating ATG (of the beta-glucuronidase (GUS) reporter gene) also enhanced expression.

The promoter expression cassettes disclosed in McElroy et al., 1991, can be easily modified for gene expression. For example, promoter-containing fragments are removed from the McElroy constructions and used to replace the double 35S promoter in pCGN1761ENX, which is then available for the insertion of specific gene sequences. The fusion genes thus constructed can then be transferred to appropriate transformation vectors. In a separate report, the rice Actl promoter with its first intron has also been found to direct high expression in cultured barley cells (Chibbar et al., 1993).

The double 35S promoter in pCGN1761ENX can be replaced with any other promoter of choice that will result in suitably high expression levels. By way of example, one of the chemically regulatable promoters disclosed in U.S. Pat. No. 5,614,395, such as the tobacco PR-1a promoter, can replace the double 35S promoter. Alternately, the *Arabidopsis* PR-1 promoter disclosed in Lebel et al., 1998, can be used. The promoter of choice can be excised from its source by restriction enzymes, but can alternatively be PCR-amplified using primers that carry appropriate terminal restriction sites.

A promoter inducible by certain alcohols or ketones, such as ethanol, can also be used to confer inducible expression of a coding sequence of the presently disclosed subject matter. Such a promoter is for example the alcA gene promoter from *Aspergillus nidulans* (Caddick et al., 1998). In *A. nidulans*, the alcA gene encodes alcohol dehydrogenase I, the expression of which is regulated by the AlcR transcription factors in presence of the chemical inducer. For the purposes of the presently disclosed subject matter, the CAT coding sequences in plasmid palcA:CAT comprising a alcA gene promoter sequence fused to a minimal 35S promoter (Caddick et al., 1998) are replaced by a coding sequence of the presently disclosed subject matter to form an expression cassette having the coding sequence under the control of the alcA gene promoter. This is carried out using methods known in the art.

Induction of expression of a nucleic acid sequence of the presently disclosed subject matter using systems based on steroid hormones is also provided. For example, a glucocorticoid-mediated induction system can be used and gene expression is induced by application of a glucocorticoid, for example, a synthetic glucocorticoid, for example dexamethasone, at a concentration ranging in some embodiments from 0.1 mM to 1 mM, and in some embodiments from 10 mM to 100 mM.

Another pattern of gene expression is root expression. A suitable root promoter is the promoter of the maize metallothionein-like (MTL) gene disclosed in de Framond, 1991, and also in U.S. Pat. No. 5,466,785, each of which is incorporated herein by reference. This "MTL" promoter is transferred to a suitable vector such as pCGN 1761 ENX for the insertion of a selected gene and subsequent transfer of the entire promoter-gene-terminator cassette to a transformation vector of interest.

Wound-inducible promoters can also be suitable for gene expression. Numerous such promoters have been disclosed (e.g. Xu et al., 1993; Logemann et al., 1989; Rohrmeier & Lehle, 1993; Firek et al., 1993; Warner et al., 1993) and all are suitable for use with the presently disclosed subject matter. Logemann et al. describe the 5' upstream sequences of the dicotyledonous potato wunl gene. Xu et al. show that a wound-inducible promoter from the dicotyledon potato (pin2) is active in the monocotyledon rice. Further, Rohrmeier & Lehle describe the cloning of the maize Wipl cDNA that is wound induced and which can be used to isolate the cognate promoter using standard techniques. Similarly, Firek et al. and Warner et al. have disclosed a wound-induced gene from the monocotyledon *Asparagus officinalis*, which is expressed at local wound and pathogen invasion sites. Using cloning techniques well known in the art, these promoters can be transferred to suitable vectors, fused to the genes pertaining to the presently disclosed subject matter, and used to express these genes at the sites of plant wounding.

A maize gene encoding phosphoenol carboxylase (PEPC) has been disclosed by Hudspeth and Grula, 1989. Using standard molecular biological techniques, the promoter for this gene can be used to drive the expression of any gene in a leaf-specific manner in transgenic plants.

A variety of transcriptional terminators are available for use in expression cassettes. These are responsible for termination of transcription and correct mRNA polyadenylation. Appropriate transcriptional terminators are those that are known to function in plants and include the CaMV 35S terminator, the tml terminator, the nopaline synthase terminator, the octopine synthase terminator, and the pea rbcS E9 terminator. These can be used in both monocotyledons and dicotyledons. In addition, a gene's native transcription terminator can be used.

Numerous sequences have been found to enhance gene expression from within the transcriptional unit and these sequences can be used in conjunction with the genes of the presently disclosed subject matter to increase their expression in transgenic plants.

Various intron sequences have been shown to enhance expression, particularly in monocotyledonous cells. For example, the introns of the maize Adhl gene have been found to significantly enhance the expression of the wild type gene under its cognate promoter when introduced into maize cells. Intron 1 was found to be particularly effective and enhanced expression in fusion constructs with the chloramphenicol acetyltransferase gene (Callis et al., 1987). In the same experimental system, the intron from the maize bronzel gene had a similar effect in enhancing expression. Intron sequences have been routinely incorporated into plant transformation vectors, typically within the non-translated leader.

Promoters for constant expression are exemplified by the 35S promoter of cauliflower mosaic virus (Odell et al., Nature, 1985, 313, 810), the actin promoter of rice (Zhang et al., Plant Cell, 1991, 3, 1155), the ubiquitin promoter of corn (Cornejo et al., Plant Mol. Biol., 1993, 23, 567), etc. Furthermore, promoters for inductive expression are exemplified by promoters that are expressed by extrinsic factors such as infection and invasion of filamentous fungi, bacteria, and viruses, low temperature, high temperature, drought, ultraviolet irradiation, spraying of particular compounds, and the like. Such promoters are exemplified by the chitinase gene promoter of rice (Xu et al., Plant Mol. Biol., 1996, 30, 387.) and tobacco PR protein gene promoter (Ohshima et al., Plant Cell, 1990, 2, 95.) expressed by the infection and invasion of filamentous fungi, bacteria and viruses, the "lip 19" gene promoter of rice induced by low temperature (Aguan et al., Mol. Gen. Genet., 1993, 240, 1), "hsp 80" and "hsp 72" gene promotors of rice induced by high temperature (Van Breusegem et al., Planta, 1994, 193, 57), "rab 16" gene promoter of *Arabidopsis thaliana* induced by dryness (Nundy et al., Proc. Natl. Acad. Sci. USA, 1990, 87, 1406), chalcone synthase gene promoter of parsley induced by ultraviolet irradiation (Schulze-Lefert et al., EMBO J., 1989, 8, 651), alcohol dehydrogenase gene promoter of corn induced by anaerobic conditions (Walker et al., Proc. Natl. Acad. Sci. USA, 1987, 84, 6624) and so on. In addition, the chitinase gene promoter of rice and PR protein gene promoter of tobacco are induced also by specific compounds such as salicylic acid, and such, and the "rab 16" gene promoter is induced by the spraying of abcisic acid, a phytohormone.

A number of non-translated leader sequences derived from viruses are also known to enhance expression, and these are particularly effective in dicotyledonous cells. Specifically, leader sequences from Tobacco Mosaic Virus (TMV; the "W-sequence"), Maize Chlorotic Mottle Virus (MCMV), and Alfalfa Mosaic Virus (AMV) have been shown to be effective in enhancing expression (see e.g., Gallie et al., 1987; Skuzeski et al., 1990). Other leader sequences known in the art include, but are not limited to, picornavirus leaders, for example, EMCV (encephalomyocarditis virus) leader (5' noncoding region; see Elroy-Stein et al., 1989); potyvirus leaders, for example, from Tobacco Etch Virus (TEV; see Allison et al., 1986); Maize Dwarf Mosaic Virus (MDMV; see Kong & Steinbiss 1998); human immunoglobulin heavy-chain binding polypeptide (BiP) leader (Macejak & Sarnow, 1991); untranslated leader from the coat polypeptide mRNA of alfalfa mosaic virus (AMV; RNA 4; see Jobling & Gehrke, 1987); tobacco mosaic virus (TMV) leader (Gallie et al., 1989); and Maize Chlorotic Mottle Virus (MCMV) leader (Lommel et al., 1991). See also Della-Cioppa et al., 1987.

The term "transcription factor" generally refers to a protein that modulates gene expression by interaction with the transcriptional regulatory element and cellular components for transcription, including RNA Polymerase, Transcription Associated Factors (TAFs), chromatin-remodeling proteins, and any other relevant protein that impacts gene transcription.

The phrases "percent identity" and "percent identical," in the context of two nucleic acid or protein sequences, refer to two or more sequences or subsequences that have in some embodiments at least 60%, in some embodiments at least 70%, in some embodiments at least 80%, in some embodiments at least 85%, in some embodiments at least 90%, in some embodiments at least 95%, in some embodiments at least 98%, and in some embodiments at least 99% nucleotide or amino acid residue identity, when compared and aligned for maximum correspondence, as measured using one of the following sequence comparison algorithms or by visual inspection. The percent identity exists in some embodiments over a region of the sequences that is at least about 50 residues in length, in some embodiments over a region of at least about 100 residues, and in some embodiments the percent identity exists over at least about 150 residues. In some embodiments, the percent identity exists over the entire length of a given region, such as a coding region.

For sequence comparison, typically one sequence acts as a reference sequence to which test sequences are compared. When using a sequence comparison algorithm, test and reference sequences are input into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

A "reference sequence" is a defined sequence used as a basis for a sequence comparison. A reference sequence can be a subset of a larger sequence, for example, as a segment of a full-length nucleotide, or amino acid sequence, or can comprise a complete sequence. Generally, when used to refer to a nucleotide sequence, a reference sequence is at least 200, 300, or 400 nucleotides in length, frequently at least 600 nucleotides in length, and often at least 800 nucleotides in length. Because two proteins can each (1) comprise a sequence (i.e., a portion of the complete protein sequence) that is similar between the two proteins, and (2) can further comprise a sequence that is divergent between the two proteins, sequence comparisons between two (or more) proteins are typically performed by comparing sequences of the two proteins over a "comparison window" (defined hereinabove) to identify and compare local regions of sequence similarity.

Optimal alignment of sequences for comparison can be conducted, for example, by the local homology algorithm described in Smith & Waterman, 1981, by the homology alignment algorithm described in Needleman & Wunsch, 1970, by the search for similarity method described in Pearson & Lipman, 1988, by computerized implementations of these algorithms (GAP, BESTFIT, FASTA, and TFASTA in the GCG WISCONSIN PACKAGE, available from Accelrys, Inc., San Diego, Calif., United States of America), or by visual inspection. See generally, Ausubel et al., 1989.

One example of an algorithm that is suitable for determining percent sequence identity and sequence similarity is the BLAST algorithm, which is described in Altschul et al., 1990. Software for performing BLAST analyses is publicly available through the National Center for Biotechnology Information via the World Wide Web. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., 1990). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when the cumulative alignment score falls off by the quantity X from its maximum achieved value, the cumulative score goes to zero or below due to the accumulation of one or more negative-scoring residue alignments, or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix. See Henikoff & Henikoff, 1992.

In addition to calculating percent sequence identity, the BLAST algorithm also performs a statistical analysis of the similarity between two sequences. See e.g., Karlin & Altschul 1993. One measure of similarity provided by the BLAST algorithm is the smallest sum probability (P(N)), which provides an indication of the probability by which a match between two nucleotide or amino acid sequences would occur by chance. For example, a test nucleic acid sequence is considered similar to a reference sequence if the smallest sum probability in a comparison of the test nucleic acid sequence to the reference nucleic acid sequence is in some embodiments less than about 0.1, in some embodiments less than about 0.01, and in some embodiments less than about 0.001.

As used herein, the terms "polypeptide", "protein", and "peptide", which are used interchangeably herein, refer to a polymer of the 20 protein amino acids, or amino acid analogs, regardless of its size or function. Although "protein" is often used in reference to relatively large polypeptides, and "peptide" is often used in reference to small polypeptides, usage of these terms in the art overlaps and varies. The term "polypeptide" as used herein refers to peptides, polypeptides and proteins, unless otherwise noted. As used herein, the terms "protein", "polypeptide", and "peptide" are used interchangeably herein when referring to a gene product. The term "polypeptide" encompasses proteins of all functions, including enzymes. Thus, exemplary polypeptides include gene products, naturally occurring proteins, homologs, orthologs, paralogs, fragments, and other equivalents, variants and analogs of the foregoing.

Modification of amino acids in proteins can include conservative and non-conservative amino acid substitutions and may further include deletions, rearrangements or additions. In one embodiment, an WAKL14 or WAKL14 homolog polypeptide contains from about 1-50 amino acid substitutions either all conservative substitutions or some conservative and some non-conservative substitutions.

The terms "polypeptide fragment" or "fragment", when used in reference to a reference polypeptide, refers to a polypeptide in which amino acid residues are deleted as compared to the reference polypeptide itself, but where the remaining amino acid sequence is usually identical to the corresponding positions in the reference polypeptide. Such deletions can occur at the amino-terminus or carboxy-terminus of the reference polypeptide, or alternatively both. Fragments typically are at least 5, 6, 8, or 10 amino acids long, at least 14 amino acids long, at least 20, 30, 40, or 50 amino acids long, at least 75 amino acids long, or at least 100, 150, 200, 300, 500, or more amino acids long. A fragment can retain one or more of the biological activities of the reference polypeptide. Further, fragments can include a sub-fragment of a specific region, which sub-fragment retains a function of the region from which it is derived. For example, a useful WAKL fragment is capable of inducing tolerance to nutrient deprivation on a sucrose or nitrogen limited media.

As used herein, the term "primer" refers to a sequence comprising in some embodiments two or more deoxyribonucleotides or ribonucleotides, in some embodiments more than three, in some embodiments more than eight, and in some embodiments at least about 20 nucleotides of an exonic or intronic region. Such oligonucleotides are in some embodiments between ten and thirty bases in length.

The term "purified" refers to an object species that is the predominant species present (i.e., on a molar basis it is more abundant than any other individual species in the composition).

The term "transfection" refers to the introduction of a nucleic acid, e.g., an expression vector, into a recipient cell, which in certain instances involves nucleic acid-mediated gene transfer. The term "transformation" refers to a process in which a cell's genotype is changed as a result of the cellular uptake of exogenous nucleic acid. For example, a transformed cell can express a recombinant form of a polypeptide of the presently disclosed subject matter.

The transformation of a cell with an exogenous nucleic acid (for example, an expression vector) can be characterized as transient or stable. As used herein, the term "stable" refers to a state of persistence that is of a longer duration than that which would be understood in the art as "transient". These terms can be used both in the context of the transformation of cells (for example, a stable transformation), or for the expression of a transgene (for example, the stable expression of a vector-encoded nucleic acid sequence comprising a trigger sequence) in a transgenic cell. In some embodiments, a stable transformation results in the incorporation of the exogenous nucleic acid molecule (for example, an expression vector) into the genome of the transformed cell. As a result, when the cell divides, the vector DNA is replicated along with plant genome so that progeny cells also contain the exogenous DNA in their genomes.

In some embodiments, the term "stable expression" relates to expression of a nucleic acid molecule (for example, a vector-encoded nucleic acid sequence comprising a trigger sequence) over time. Thus, stable expression requires that the cell into which the exogenous DNA is introduced express the encoded nucleic acid at a consistent level over time. Additionally, stable expression can occur over the course of generations. When the expressing cell divides, at least a fraction of the resulting daughter cells can also express the encoded nucleic acid, and at about the same level. It should be understood that it is not necessary that every cell derived from the cell into which the vector was originally introduced express the nucleic acid molecule of interest. Rather, particularly in the context of a whole plant, the term "stable expression" requires only that the nucleic acid molecule of interest be stably expressed in tissue(s) and/or location(s) of the plant in which expression is desired. In some embodiments, stable expression of an exogenous nucleic acid is achieved by the integration of the nucleic acid into the genome of the host cell.

The term "vector" refers to a nucleic acid capable of transporting another nucleic acid to which it has been linked. One type of vector that can be used in accord with the presently disclosed subject matter is an *Agrobacterium* binary vector, i.e., a nucleic acid capable of integrating the nucleic acid sequence of interest into the host cell (for example, a plant cell) genome. Other vectors include those capable of autonomous replication and expression of nucleic acids to which they are linked. Vectors capable of directing the expression of genes to which they are operatively linked are referred to herein as "expression vectors". In general, expression vectors of utility in recombinant DNA techniques are often in the form of plasmids. In the present specification, "plasmid" and "vector" are used interchangeably as the plasmid is the most commonly used form of vector. However, the presently disclosed subject matter is intended to include such other forms of expression vectors which serve equivalent functions and which become known in the art subsequently hereto.

The term "expression vector" as used herein refers to a DNA sequence capable of directing expression of a particular nucleotide sequence in an appropriate host cell, comprising a promoter operatively linked to the nucleotide sequence of interest which is operatively linked to transcription termination sequences. It also typically comprises sequences required for proper translation of the nucleotide sequence. The construct comprising the nucleotide sequence of interest can be chimeric. The construct can also be one that is naturally occurring but has been obtained in a recombinant form useful for heterologous expression. The nucleotide sequence of interest, including any additional sequences designed to effect proper expression of the nucleotide sequences, can also be referred to as an "expression cassette".

Embodiments of the presently disclosed subject matter provide an expression cassette comprising one or more elements operably linked in an isolated nucleic acid. In some embodiments, the expression cassette comprises one or more operably linked promoters, coding sequences, and/or promoters.

Further encompassed within the presently disclosed subject matter are recombinant vectors comprising an expression cassette according to the embodiments of the presently disclosed subject matter. Also encompassed are plant cells comprising expression cassettes according to the present disclosure, and plants comprising these plant cells.

In some embodiments, the expression cassette is expressed in a specific location or tissue of a plant. In some embodiments, the location or tissue includes, but is not limited to, epidermis, root, vascular tissue, meristem, cambium, cortex, pith, leaf, flower, seed, and combinations thereof.

The presently disclosed subject matter further provides a method for modifying (i.e. increasing or decreasing) the concentration or composition of a polypeptide of the presently disclosed subject matter having an effect on plant growth in a nutrient media (e.g., a nutrient deficient soil). The method comprises in some embodiments introducing into a plant cell an expression cassette comprising a nucleic acid molecule of the presently disclosed subject matter as disclosed above to obtain a transformed plant cell or tissue (also referred to herein as a "transgenic" plant cell or tissue), and culturing the transformed plant cell or tissue. The nucleic acid molecule can be under the regulation of a constitutive or inducible promoter, and in some embodiments can be under the regulation of a tissue—or cell type-specific promoter.

A plant or plant part having modified expression of a nucleic acid molecule of the presently disclosed subject matter can be analyzed and selected using methods known to those skilled in the art including, but not limited to, Southern blotting, DNA sequencing, and/or PCR analysis using primers specific to the nucleic acid molecule and detecting amplicons produced therefrom. For example, a host cell transformed with a vector or polynucleotide of the disclosure can be analyzed for growth on a sucrose or nitrogen deficient media compared to a non-transformed cell. Cells that have increased growth capacity on a nutrient deficient media are indicative of a cell transformed with a polynucleotide of the disclosure.

In general, the presently disclosed compositions and methods can result in a plant the demonstrates improved growth capacity or life on a nutrient deficient media (e.g., a nutrient deficient soil such as one lacking sucrose or nitrogen) by at least 5%, in some embodiments at least 10%, in some embodiments at least 20%, in some embodiments at least 30%, in some embodiments at least 40%, in some embodiments at least 50%, in some embodiments at least 60%, in some embodiments at least 70%, in some embodiments at least 80%, and in some embodiments at least 90% relative to a native control plant, plant part, or cell lacking the expression cassette.

Numerous transformation vectors available for plant transformation are known to those of ordinary skill in the plant transformation art, and the genes pertinent to the presently disclosed subject matter can be used in conjunction with any such vectors. The selection of vector will depend upon the selected transformation technique and the target species for transformation. For certain target species, different antibiotic or herbicide selection markers might be employed. Selection markers used routinely in transformation include the nptII gene, which confers resistance to kanamycin and related antibiotics (Messing & Vieira, 1982; Bevan et al., 1983); the bargene, which confers resistance to the herbicide phosphinothricin (White et al., 1990; Spencer et al., 1990); the hph gene, which confers resistance to the antibiotic hygromycin (Blochinger & Diggelmann, 1984); the dhfr gene, which confers resistance to methotrexate (Bourouis & Jarry, 1983); the EPSP synthase gene, which confers resistance to glyphosate (U.S. Pat. Nos. 4,940,935 and 5,188,642); and the mannose-6-phosphate isomerase gene, which provides the ability to metabolize mannose (U.S. Pat. Nos. 5,767,378 and 5,994,629).

Many vectors are available for transformation using *Agrobacterium tumefaciens*. These typically carry at least one T-DNA border sequence and include vectors such as PBIN19 (Bevan, 1984). Below, the construction of two typical vectors suitable for *Agrobacterium* transformation is disclosed.

Transformation without the use of *Agrobacterium tumefaciens* circumvents the requirement for T-DNA sequences in the chosen transformation vector, and consequently vectors lacking these sequences can be utilized in addition to other vectors that contain T-DNA sequences. Transformation techniques that do not rely on *Agrobacterium* include transformation via particle bombardment, protoplast uptake (e.g. polyethylene glycol (PEG) and electroporation), and microinjection. The choice of vector depends largely on the species being transformed.

Once a nucleic acid sequence of the presently disclosed subject matter has been cloned into an expression system, it is transformed into a plant cell. The expression cassettes of the presently disclosed subject matter can be introduced into the plant cell in a number of art-recognized ways. Methods for regeneration of plants are also well known in the art. For example, Ti plasmid vectors have been utilized for the delivery of foreign DNA, as well as direct DNA uptake, liposomes, electroporation, microinjection, and microprojectiles. In addition, bacteria from the genus *Agrobacterium* can be utilized to transform plant cells. Below are descriptions of representative techniques for transforming both dicotyledonous and monocotyledonous plants, as well as a representative plastid transformation technique.

Transformation techniques for dicotyledons are well known in the art and include *Agrobacterium*-based techniques and techniques that do not require *Agrobacterium*. Non-Agrobacterium techniques involve the uptake of exogenous genetic material directly by protoplasts or cells. This can be accomplished by PEG or electroporation-mediated uptake, particle bombardment-mediated delivery, or microinjection. Examples of these techniques are disclosed in Paszkowski et al., 1984; Potrykus et al., 1985; and Klein et al., 1987. In each case the transformed cells are regenerated to whole plants using standard techniques known in the art.

*Agrobacterium*-mediated transformation is a useful technique for transformation of dicotyledons because of its high efficiency of transformation and its broad utility with many different species. *Agrobacterium* transformation typically involves the transfer of a binary vector carrying the foreign DNA of interest to an appropriate *Agrobacterium* strain which can depend on the complement of vir genes carried by the host *Agrobacterium* strain either on a co-resident Ti plasmid or chromosomally.

Transformation of the target plant species by recombinant *Agrobacterium* usually involves co-cultivation of the *Agrobacterium* with explants from the plant and follows protocols well known in the art. Transformed tissue is regenerated on selectable medium carrying the antibiotic or herbicide resistance marker present between the binary plasmid T-DNA borders.

Various techniques can be used to introduce an aforementioned expression vector into host plant cells. As described above examples of these techniques include transformation of plant cells by T-DNA using *Agrobacterium tumefaciens* or *Agrobacterium rhizogenes* for the transformation factor, direct introduction into a protoplast (by a method such as electroporation in which a DNA is introduced into plant cells by treating protoplasts with an electric pulse, fusion of protoplasts with liposomes and so forth, microinjection, and the use of polyethylene glycol), and the use of a particle gun.

In addition, a desired gene can be introduced into a plant, by using a plant virus as vector. An example of a plant virus that can be used is cauliflower mosaic virus. Namely, after first preparing a recombinant by inserting the virus genome into a vector derived from *E. coli* and so forth, the desired gene is inserted into the virus genome. Such desired genes can then be introduced into a plant by cutting out the virus genome modified in this manner from the recombinant with a restriction enzyme, and inoculating into the plant (Hohn, et al. (1982), Molecular Biology of Plant Tumors (Academic Press, New York), p. 549, U.S. Pat. No. 4,407,956). The technique for introducing a vector into plant cells or a plant is not limited to these, and includes other possibilities as well.

There are no limitations on the required vector in the case of direct insertion into a protoplast. For example, a simple plasmid such as a pUC derivative can be used. Other DNA sequences may be required depending on the method used to introduce the desired gene into plant cells. For example, in the case of using a Ti or Ri plasmid to transform plant cells, at least the sequence on the right end, and typically the sequences on both ends, of the T-DNA region of Ti and Ri plasmids must be connected so as to become an adjacent region of the gene to be introduced.

When using an *Agrobacterium* species for transformation, a gene to be introduced needs to be cloned into a special plasmid, namely an intermediate vector or a binary vector. Intermediate vectors are not replicated in *Agrobacterium* species. Intermediate vectors are transferred into *Agrobacterium* species by helper plasmids or electroporation. Since intermediate vectors have a region that is homologous with the T-DNA sequence, they are incorporated within the Ti or Ri plasmid of *Agrobacterium* species by homologous recombination. It is necessary for the *Agrobacterium* species used for the host to comprise a vir region. Normally, Ti or Ri plasmids comprise a vir region, and due to its function, T-DNA can be transferred into plant cells.

On the other hand, since a binary vector can be replicated and maintained in *Agrobacterium* species, when a vector is incorporated into *Agrobacterium* species by a helper plasmid or electroporation, the T-DNA of the binary vector can be transferred into plant cells due to the action of the vir region of the host.

Furthermore, intermediate vectors or binary vectors obtained in this manner, as well as microorganisms such as *E. coli* and *Agrobacterium* species that comprise them are also included in the disclosure.

Another approach to transforming plant cells with a gene involves propelling inert or biologically active particles at plant tissues and cells. This technique is disclosed in U.S. Pat. Nos. 4,945,050; 5,036,006; and 5,100,792; all to Sanford et al. Generally, this procedure involves propelling inert or biologically active particles at the cells under conditions effective to penetrate the outer surface of the cell and afford incorporation within the interior thereof. When inert particles are utilized, the vector can be introduced into the cell by coating the particles with the vector containing the desired gene. Alternatively, the target cell can be surrounded by the vector so that the vector is carried into the cell by the wake of the particle. Biologically active particles (e.g., dried yeast cells, dried bacterium, or a bacteriophage, each containing DNA sought to be introduced) can also be propelled into plant cell tissue.

There are no particular limitations on the genus or species of plants that can be used in the methods and compositions of the disclosure. Examples include useful agricultural crops such as grains, vegetables, and fruits (including feed crops), fiber raw material plants such as pulp, and plants valued for their aesthetic beauty such as foliage plants. The methods and compositions of the disclosure can be used in *Eucalyptus*, pine, acacia, poplar, cedar, cypress, bamboo, yew, rice, corn, wheat, barley, rye, potato, tobacco, sugar beet, sugar cane, rapeseed, soybean, sunflower, cotton, orange, grape, peach, pear, apple, tomato, Chinese cabbage, cabbage, radish, carrot, squash, cucumber, melon, parsley, orchid, chrysanthemum, lily, and saffron. In addition, some microorganisms produce various types of cellulosic material. The methods and compositions of the disclosure can be used in the generation of recombinant microorganism for the production of cellulosic material. Such microorganisms and plants may be useful for the production of biofuels and the like.

In addition, the disclosure provides transgenic plant cells into which a vector of the disclosure has been introduced. There are no particular limitations on the cells into which a vector of the disclosure is introduced, examples of which include the cells of rice, corn, wheat, barley, rye, potato, tobacco, sugar beet, sugar cane, rapeseed, soybean, sunflower, cotton, orange, grape, peach, pear, apple, tomato, Chinese cabbage, cabbage, radish, carrot, squash, cucumber, melon, parsley, orchid, chrysanthemum, lily, and saffron; however, trees such as *Eucalyptus*, pine, acacia, poplar, cedar, cypress, bamboo, and yew are preferable. In addition, plant cells of the disclosure comprise cultured cells, as well as cells present in a plant. In addition, protoplasts, shoot primordia, multiple shoots, and hairy roots are also included.

A transgenic plant of the disclosure is useful as a plant having a novel value such as increased plant growth as a result of increasing plant growth on a nutrient deficient soil or media such as in agricultural crops.

In the disclosure, a "transgenic plant" refers to a plant having the aforementioned transgenic plant cells, and includes, for example, a transgenic plant regenerated from the aforementioned transgenic cells. Although the methods used to regenerate individual plants from transformed plant cells vary according to the type of plant cell, an example of a method used in rice plants is the method of Fujimura et al. (Fujimura et al., Plant Tissue Culture Lett., 2, 74, 1995), the method of Shillito et al. (Shillito et al., Bio/Technology, 7, 581, 1989) in corn plants, the method of Visser et al. (Visser et al., Theor. Appl. Genet., 78, 589, 1989) in potato plants, the method of Akama et al. (Akama et al., Plant Cell Rep., 12, 7, 1992) in *Arabidopsis thaliana*, and the method of Doi et al. (Japanese Patent Application No. Hei 11-127025) in Eucalyptus plants. Transgenic plants produced according to these methods or transgenic plants obtained from their breeding materials (such as seeds, tubers, or cuttings) are included in the disclosure.

The disclosure includes a process of producing a plant from a plant seed by introducing into a host an expression vector comprising a promoter region that is contiguous with a wall-associated kinase like polynucleotide of the disclosure to obtain transgenic cells, regenerating a transgenic plant from said transgenic cells, and obtaining a plant seed from the resulting transgenic plant.

A process of obtaining a plant seed from a transgenic plant refers to a process in which, for example, a transgenic plant is acquired from a rooting medium, replanted in a pot containing moist soil, and grown at a constant temperature to form flowers, and finally seeds. In addition, a process of producing a plant from a seed refers to a process in which, for example, once a seed formed in a transgenic plant has matured, the seed is isolated, sowed on moist soil, and then grown at a constant temperature and luminosity, to produce a plant.

The exogenously introduced DNA or nucleic acid in a transformed plant can be confirmed by known methods, such as PCR or Southern hybridization, or by analyzing the nucleotide sequence of the plant's nucleic acid. To extract DNA or nucleic acid from a transformed plant, the known method of J. Sambrook et al. may be used (Molecular Cloning, 2nd edition, Cold Spring Harbor laboratory Press, 1989).

To conduct PCR analysis of a DNA of the disclosure that exists in a plant, an amplification reaction is carried out using, as a template, nucleic acid extracted from the regenerated plant. Amplification reaction may be carried out in a reaction mixture containing, as primers, synthesized oligonucleotides comprising nucleotide sequences appropriately selected according to the nucleotide sequence of a DNA of the disclosure. An amplified DNA fragment comprising a DNA sequence of the disclosure may be obtained by repeating several dozen cycles of the denaturation, annealing, and extension steps of the DNA amplification reaction. The respective amplified DNA fragments can be separated by, for example, electrophoresing the reaction solution containing the amplified products on agarose gel. DNA fragments corresponding to a DNA of the disclosure can then be confirmed.

Having obtained a transformed plant in which a DNA of the disclosure has been inserted into the chromosomes, one can obtain the plant's offspring by sexual or non-sexual reproduction. Also, it is possible to mass-produce such plants by obtaining reproductive materials (such as seeds, fruits, cuttings, stem tubers, root tubers, shoots, calluses, and protoplasts) from the above plant, or its offspring or clones.

Plants that are useful in the methods of the disclosure include all plants which belong to the superfamily Viridiplantae, in particular monocotyledonous and dicotyledonous plants including fodder or forage legumes, ornamental plants, food crops, trees or shrubs selected from the list comprising *Acacia* spp., *Acer* spp., *Actinidia* spp., *Aesculus* spp., *Agathis australis*, *Albizia amara*, *Alsophila tricolor*, *Andropogon* spp., *Arachis* spp, *Areca catechu*, *Astelia fragrans*, *Astragalus cicer*, *Baikiaea pluriuga*, *Betula* spp., *Brassica* spp., *Bruguiera gymnorrhiza*, *Burkea africana*, *Butea frondosa*, *Cadaba farinosa*, *Calliandra* spp, *Camellia sinensis*, *Canna indica*, *Capsicum* spp., *Cassia* spp., *Centroema pubescens*, *Chaenomeles* spp., *Cinnamomum cassia*, *Coffea arabica*, *Colophospermum mopane*, *Coronillia varia*, *Cotoneaster serotina*, *Crataegus* spp., *Cucumis* spp., *Cupressus* spp., *Cyathea dealbata*, *Cydonia oblonga*, *Cryptomeria japonica*, *Cymbopogon* spp., *Cynthea dealbata*, *Cydonia oblonga*, *Dalbergia monetaria*, *Davallia divaricata*, *Desmodium* spp., *Dicksonia squarosa*, *Diheteropogon amplectens*, *Dioclea* spp, *Dolichos* spp., *Dorycnium rectum*, *Echinochloa pyramidalis*, *Ehrartia* spp., *Eleusine coracana*, *Eragrestis* spp., *Erythrina* spp., *Eucalyptus* spp., *Euclea schimperi*, *Eulalia villosa*, *Fagopyrum* spp., *Feijoa sellowiana*, *Fragaria* spp., *Flemingia* spp, *Freycinetia banksii*, *Geranium thunbergii*, *Ginkgo biloba*, *Glycine javanica*, *Gliricidia* spp, *Gossypium hirsutum*, *Grevillea* spp., *Guibourtia coleosperma*, *Hedysarum* spp., *Hemarthia altissima*, *Heteropogon contortus*, *Hordeum vulgare*, *Hyparrhenia rufa*, *Hypericum erectum*, *Hyperthelia dissoluta*, *Indigo incarnata*, *Iris* spp., *Leptarrhena pyrolifolia*, *Lespediza* spp., *Lettuca* spp., *Leucaena leucocephala*, *Loudetia simplex*, *Lotonus bainesii*, *Lotus* spp., *Macrotyloma axillare*, *Malus* spp., *Manihot esculenta*, *Medicago sativa*, *Metasequoia glyptostroboides*, *Musa sapientum*, *Nicotianum* spp., *Onobrychis* spp., *Ornithopus* spp., *Oryza* spp., *Peltophorum africanum*, *Pennisetum* spp., *Persea gratissima*, *Petunia* spp., *Phaseolus* spp., *Phoenix canariensis*, *Phormium cookianum*, *Photinia* spp., *Picea glauca*, *Pinus* spp., *Pisum sativum*, *Podocarpus totara*, *Pogonarthria fleckii*, *Pogonarthria squarrosa*, *Populus* spp., *Prosopis cineraria*, *Pseudotsuga menziesii*, *Pterolobium stellatum*, *Pyrus communis*, *Quercus* spp., *Rhaphiolepsis umbellata*, *Rhopalostylis sapida*, *Rhus natalensis*, *Ribes grossularia*, *Ribes* spp., *Robinia pseudoacacia*, *Rosa* spp., *Rubus* spp., *Salix* spp., *Schyzachyrium sanguineum*, *Sciadopitys verticillata*, *Sequoia sempervirens*, *Sequoiadendron giganteum*, *Sorghum bicolor*, *Spinacia* spp., *Sporobolus fimbriatus*, *Stiburus alopecuroides*, *Stylosanthos humilis*, *Tadehagi* spp, *Taxodium distichum*, *Themeda triandra*, *Trifolium* spp., *Triticum* spp., *Tsuga heterophylla*, *Vaccinium* spp., *Vicia* spp., *Vitis vinifera*, *Watsonia pyramidata*, *Zantedeschia aethiopica*, *Zea mays*, amaranth, artichoke, asparagus, broccoli, Brussels sprouts, cabbage, canola, carrot, cauliflower, celery, collard greens, flax, kale, lentil, oilseed rape, okra, onion, potato, rice, soybean, strawberry, sugar beet, sugar cane, sunflower, tomato, squash, tea and algae, amongst others.

The following examples are provided to further illustrate but not limit the disclosure.

EXAMPLES

*Arabidopsis thaliana* ecotype Columbia-0 (Col-0) was used in aspect of the disclosure. Before plating seeds were surface sterilized. First, the seeds were washed in 95% ethanol for 10 minutes, which was removed then the sterilization solution was added (20% bleach, 0.05% Tween-20 (Sigma)

and double distilled water) and shaken for 10 minutes. The sterilization solution is removed and the seeds are washed three times with sterile distilled water. The seeds were cold treated for 4 days at 4° C. after plating them on the plates. Four different growth media were prepared for these experiments. For the control conditions: one-half strength Murashige and Skoog (MS) salts (Sigma), 0.5% sucrose (Sigma), 0.8% phyto agar (Research Products International Corp.), 1×B5 (1,000× in double distilled water: 10% myo-inositol, 0.1% nicotinic acid and 0.1% pyroxidine HCl) and 1× Thiamin (2,000× in double distilled water: 0.2% thiamin HCl). For low nitrogen media: 10×MS micronutrient media (Sigma) was diluted to 0.5× and 10×MS macronutrient containing no nitrogen (40 mM $CaCl_2.2H_2O$, 30 mM $MgSO_4.7H_2O$ and 12.5 mM $KH_2PO_4$) was also diluted to 0.5× and 100× Fe.EDTA (18.3 mM $FeSO_4$ and 12.5 mM EDTA) was added to a final concentration of 1×. All the other components of the control media were kept the same. For sucrose-less media all components of the control media were included except for the omission of sucrose. The final media condition was a dilute MS solution. Here, one-half MS media was further diluted to one-sixth MS salt concentrations; all other components were kept the same. All media was brought to pH 5.8 with 1N KOH and autoclaved for 20 minutes. Plates were arranged vertically in the growth room and grown at 22° C., in either 150 µM photons/m-1 s-1 (normal light) or 45 µM photons/m-1 s-1 (low light) condition, with a 16 h light, 8 h dark photoperiod.

Mutant Construction.

The Invitrogen Gateway technology was used to expedite the generation of the different RLK mutations used in this study. Generally, the RIKEN cDNA clone (pda08425, WAKL14) was used as a template for polymerase chain reaction (PCR) amplification of either the dominant negative, full-length or kinase only portion of the receptor.

Primers Used:
WAKL14 FWD (SalI): 5'-GGAAGTCGACGGAAGGT-GATGAATGTTGAGATCG-3' (SEQ ID NO:19); WAKL14 KIN-FWD (SalI):5'-GGAAGTCGACGAGACGGTC-TACTCCTTTGAGAGGTC-3' (SEQ ID NO:20); WAKL14 DN-REV (NotI):5'-ATATGCGGCCGCAGACGGACAA-GATTCGGGTGACTC-3' (SEQ ID NO:21); WAKL14 FL-REV (NotI):5'-ATATGCGGCCGCGGAATGTTACCGAG-CAATGTA TTTG-3' (SEQ ID NO:22).

PCR product was gel eluted using the QIAquick gel extraction kit (Qiagen) using the manufacturer's protocol. Eluted DNA was subsequently ligated into Promega's pGEM-Teasy PCR vector. Positive colonies were picked and the insert was confirmed by DNA sequencing, using the vectors T7 and S6 primer binding sites. Confirmed vectors were then restriction digested using the PCR introduced restriction sites (SalI or NotI). The restriction digest was then run on a 1% agarose (Invitrogen) gel and the digested insert was removed using the QIAquick kit. The fragment was then ligated into a TAP tagged entry vector that was made by taking the pENTR-1A vector (Invitrogen) and introducing a 6×His and T7 epitope DNA sequence into the EcoRV restriction site in the pENTR-1A vector. This vector was designated pENTR-TAP2. The 3' ends of all PCR fragments were designed to go into frame with the TAP sequence, which would be introduced into the C-terminus, intracellular portion, of the DN-RLK protein. The pENTR-TAP2 vectors containing the desired fragments were then introduced into the final destination binary vector that contains the 35S promoter, pGWB2 (Invitrogen, Nakagawa). This construct was introduced into Arabidopsis (Col-0) via the floral dip method (Bechtold et al., 1993). Subsequent generations of the seeds were selected for using 50 µg/ml Kanamycin (Sigma) in MS media (same as control media except for addition of antibiotic), until T3 homozygous lines were obtained, which were used for all subsequent experiments.

RNA and Real-Time PCR Analysis.

RNA was collected from ten-day-old vertically grown seedlings using Qiagen's RNeasy Kit following the manufacture's protocol. Three micrograms of total RNA was used in a reverse transcriptase (Superscript II, Invitrogen) reaction in a 20 µl reaction volume. The cDNA was subsequently diluted to a concentration of 15 ng/µl and 5 µl (75 ng cDNA) was used per each real-time reaction (25 µl total reaction volume: 0.125 µl each primer (100 pM), 12.5 µl Bio-Rad SYBR green master mix, and sterile/DEPC dd$H_2O$). Primers for real-time PCR were designed in all circumstances to span an intron region and to be a final size of 300 base pairs (+/−5 base pairs).

Primers used: ACTIN2 FWD: 5'-GATGGGCAAGTCAT-CACGATTGG-3' (SEQ ID NO:23); ACTIN2 REV: 5'-AC-CACCGATCCAGACACTGTACTTCC-3' (SEQ ID NO:24); DIN1/SEN1 FWD: 5'-GGAAACTGGTCATCGGC-TATTTCTC-3' (SEQ ID NO:25); DIN1/SEN1 REV: 5'-TCT-GTACATGTAAGGTACGTTGATGGC-3' (SEQ ID NO:26); DIN2/SRG2 FWD: 5'-GCTAAGGGATCGTGGTTCT-TCATTATC-3' (SEQ ID NO:27); DIN2/SRG2 REV: 5'-AGCGTCCATGTTTAGCTCCTTCATC-3' (SEQ ID NO:28); DIN6 FWD: 5'-GTGGAATACTTGCCGTGTTAG-GATG-3' (SEQ ID NO:29); DIN6 REV: 5'-GACTTCA-CAATCACTACCAGTACGGAAC-3' (SEQ ID NO:30).

The real-time PCR protocol was 95° C. for 5 minutes, followed by 40 cycles of 95° C. for 45 seconds and 60° C. for 45 seconds with the fluorescence quantification at the end of every 60° C. step. The fold change was found using the delta delta Ct method using the wild type ACTIN2 as the control for relative gene expression values.

Screening for DN-RLKs that alter responses to sucrose depletion or high levels of sucrose. To identify RLKs potentially involved in the sensing of nutrient status, DN-RLK transgenic lines were screened for altered responses to sucrose depletion with seedlings grown in normal MS agar medium. Seeds from T3 homozygous lines were germinated on MS media lacking sucrose or containing high levels of sucrose (6%) compared with those germinated on MS media containing 0.5% sucrose. Forty-two DN-RLK subfamilies were examined in this experiment and wherever possible at least three independent lines for each DN construct were analyzed. At six days after germination, the length of the roots was examined. Tables 1 and 2 summarize the results with sucrose depletion. From the 42 DN-RLK screened, 11 showed reduced root elongation and seven exhibited increased root elongation in the normal MS medium compared to wild type seedlings. In the absence of sucrose, wild type Arabidopsis seedlings exhibited greatly reduced root elongation compared to those grown in 0.5% sucrose. DN-DUF26 (At4g23290) and DN-WAKL14 (At2g23450) dramatically enhanced sucrose depletion-induced reduction in root elongation (FIG. 1). In contrast, several other DN-RLKs [two LRRIII genes (At5g10020 and At3g08680)] completely suppressed sucrose depletion-induced root growth inhibition (FIG. 1).

TABLE 1

Dominant negative (DN) receptor-like kinases showing shorter roots on MS and -sucrose media. Plants were grown vertically for 6 days after germination (DAG) under normal luminescence (150 μM photons s$^{-1}$ m$^{-2}$) and photographed and then analyzed using NIH Image software.

| (DN) AGI | PNAS | PlantsP | MS | DN root length Relative to WT (MS) | t-test (p-value) | -sucrose | DN root length Relative to WT (-sucrose) | t-test (p-value) |
|---|---|---|---|---|---|---|---|---|
| At4g23290 | DUF26 | 1.7-19 | shorter | 0.71 | 0.00001 | shorter | 0.481 | 0.003 |
| At5g03140 | L-Lectin | 1.11-3 | ns | 1.01 | 0.42 | shorter | 0.379 | 0.009 |
| At3g02880 | LRR III | 1.13-4 | longer | 1.23 | 0.001 | shorter | 0.331 | 0.008 |
| At4g23740 | LRR III | 1.13-5 | longer | 1.18 | 0.03 | shorter | 0.394 | 0.04 |
| At3g57830 | LRR III | 1.13-9 | shorter | 0.84 | 0.02 | shorter | 0.130 | 0.004 |
| At3g03770 | LRR VI | 1.15-4 | ns | 0.90 | 0.06 | shorter** | 0.044 | 0.00005 |
| At4g39270 | LRR IV | 1.15-5 | shorter | 0.74 | 0.006 | shorter | 0.196 | 0.03 |
| At4g20790 | LRR VI | 1.Other-9 | shorter | 0.80 | 0.002 | shorter | 0.156 | 0.001 |
| At1g21590 | LRR VI | 1.10-1 | ns | 1.01 | 0.46 | shorter | 0.355 | 0.01 |
| At3g28450 | LRR X | 1.12-5 | shorter | 0.80 | 0.00001 | shorter | 0.277 | 0.0003 |
| At5g62710 | LRR XIII | 1.12-30 | shorter | 0.76 | 0.006 | shorter | 0.170 | 0.02 |
| At2g11520 | RLCK IV | 1.5-1 | shorter | 0.52 | 0.00003 | shorter** | 0.087 | 0.0002 |
| At1g61380 | SD-1 | 1.7-29 | ns | 0.98 | 0.35 | shorter | 0.121 | 0.0005 |
| At1g49730 | URK1 | 1.3-2 | shorter | 0.91 | 0.03 | shorter | 0.153 | 0.0007 |
| At1g16260 | WAKL | 1.5-2 | shorter | 0.90 | 0.04 | shorter | 0.180 | 0.02 |
| At1g16130 | WAKL | 1.5-3 | ns | 1.02 | 0.31 | shorter | 0.131 | 0.001 |
| At2g23450 | WAKL | 1.5-11 | ns | 1.05 | 0.26 | shorter | 0.120 | 0.003 |

**Extremely shorter roots than wild type.
ns = not significant.
(The sequences associated with the AGI Accession numbers are incorporated herein by reference)

TABLE 2

Dominant negative (DN) receptor-like kinases showing longer roots on MS and -sucrose media. Plants were grown vertically for 6 days after germination (DAG) under normal luminescence (150 μM photons s$^{-1}$ m$^{-2}$) and photographed and then analyzed using NIH Image software.

| (DN) AGI | PNAS | PlantsP | MS | DN root length Relative to WT (MS) | t-test (p-value) | -sucrose | DN root length Relative to WT (-sucrose) | t-test (p-value) |
|---|---|---|---|---|---|---|---|---|
| At4g04570 | DUF26 | 1.7-25 | ns | 0.99 | 0.39 | longer | 1.36 | 0.0001 |
| At5g10020 | LRR III | 1.Other-12 | longer | 1.18 | 0.01 | longer | 1.64 | 0.03 |
| At3g51740 | LRR III | 1.12-6 | longer | 1.34 | 0.000003 | longer** | 2.49 | 0.0000004 |
| At1g73080 | LRR XI | 1.12-13 | longer | 1.36 | 0.0003 | longer | 1.63 | 0.009 |
| At5g67200 | LRR III | 1.13-2 | longer | 1.30 | 0.00002 | longer | 1.73 | 0.006 |
| At3g08680 | LRR III | 1.13-3 | longer | 1.18 | 0.009 | longer | 1.91 | 0.002 |
| At2g24230 | LRR VII | NF-7 | longer | 1.23 | 0.0008 | longer** | 2.13 | 0.0008 |

**Extremely longer than wild type.
ns = not significant.
(The sequences associated with the AGI Accession numbers are incorporated herein by reference)

TABLE 3

Dominant negative (DN) receptor-like kinases showing shorter roots on 6% sucrose media. Plants were grown vertically for 6 days after germination (DAG) under normal luminescence (150 μM photons s$^{-1}$ m$^{-2}$) and photographed and then analyzed using NIH Image software.

| (DN) AGI | PNAS | PlantsP | MS | DN root length Relative to WT (MS) | t-test (p-value) | 6% sucrose | DN root length Relative to WT (6% sucrose) | t-test (p-value) |
|---|---|---|---|---|---|---|---|---|
| At3g51740 | LRR III | 1.12-6 | longer | 1.34 | 0.000003 | longer | 1.52 | 0.0003 |
| At5g03140 | L-Lectin | 1.11-3 | ns | 1.01 | 0.42 | longer | 1.33 | 0.006 |

(The sequences associated with the AGI Accession numbers are incorporated herein by reference)

Figure 2:
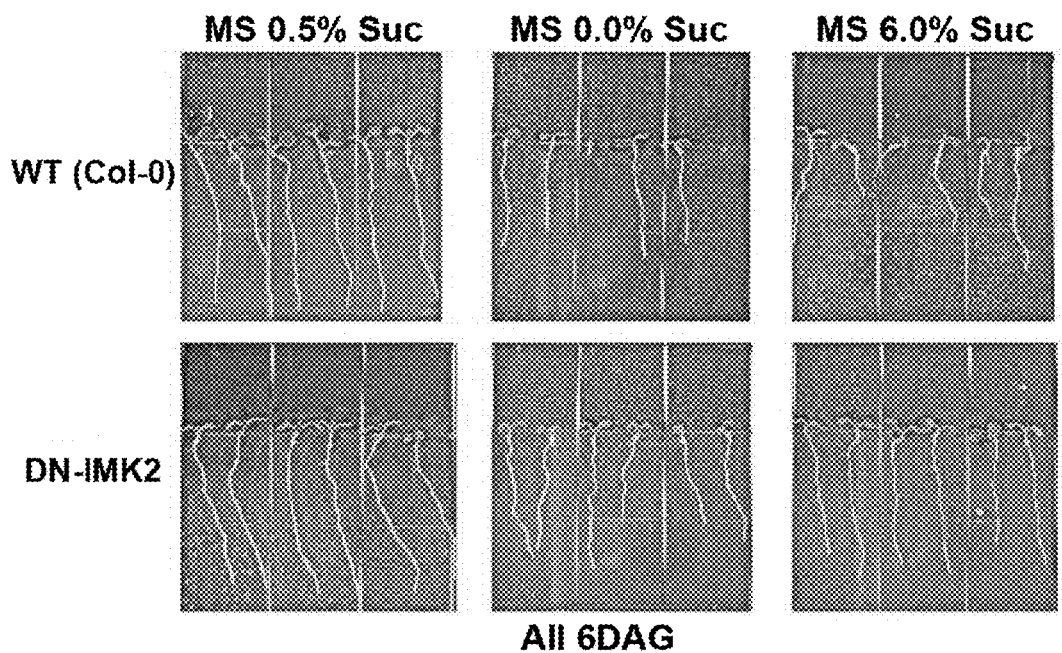
FIG. 2 show six-day-after germination wild type and DN-IMK2 seedlings grown vertically on normal MS (0.5% sucrose), increased sucrose MS (6%) and reduced sucrose MS (0% sucrose) media. It is noteworthy that DN-IMK2 does not show any anthocyanin accumulation typical of sugar stress that the wild type exhibits at 6% sucrose. This phenotype is found in at least three different independent lines of DN-IMK2.

Eight DN-RLKs were also tested for their sensitivity to increased sucrose (6%) and found that the majority had no significant difference in root growth to the wild type (Table 3). Only one DN-RLK (DN-SRF2, At5g06820) had decreased root growth on 6% sucrose and one DN-RLK (DN-IMK2, At3g51740) had increased root growth. DN-IMK2 exhibited insensitivity to both sucrose-depletion and to increased sucrose levels (6%). As can be seen in FIG. 2. DN-IMK2 seedlings produced "normal" roots in either sucrose-less or high sucrose medium, whereas root growth of wild type seedlings was dramatically inhibited under either condition. There was a noticeable lack of anthocyanin accumulation, at high levels of sucrose, in DN-IMK2 compared to the wild type. These results suggest that the IMK2 RLK is a novel sucrose sensor. Overexpression of the full-length or kinase domain of Wall-Associated Kinase-Like 14 (WAKL14) reduced root growth inhibition induced by sucrose depletion.

22-members of the WAKL family were selected for further investigation of their involvement in nutrient responses because it represents one of the larger RLK families in *Arabidopsis*. As shown above, ectopic DN-WAKL14 expression increased root growth inhibition induced by sucrose depletion, suggesting that WAK14 may be involved in the positive regulation of sucrose depletion responses. To further test this hypothesis, transgenic lines were generated overexpressing the full-length wild type WAK14 cDNA (35S:WAKL) and a construct containing only the transmembrane and intracellular kinase domains (35S:WAKL KIN). A 35S:WAKL KIN transgenic lines was generated to investigate if the kinase domain only could function as a constitutively active form of the RLK. The 35S:WAKL14 and 35S:WAKL KIN transgenic lines were statistically less sensitive (p<0.05) to sucrose depletion then the wild type and much less sensitive to sucrose depletion then DN-WAKL14 (p<0.01) (FIG. 3). Two different light conditions were used in this experiment. "Normal" light (150 µM photons s-1 m-2) was used as a control, whereas "low" light (45 µM photons s-1 m-2) was used because reduced photosynthesis would exacerbate the effects of sucrose depletion and expose sucrose requirements.

WALK14 Positively Regulates Responses to Nitrogen Depletion.

DN-WAKL14, 35S:WAKL14 and 35S:WAKL KIN were examined for sensitivity to depletion of nitrogen. DN-WAKL14 seedlings were statistically more sensitive to nitrogen deprivation (p<0.05) than the wild type but 35S:WAKL14 seedlings were less sensitive (p<0.01) (FIG. 4). This opposite response to nitrogen depletion suggests that WAKL14 may also be involved in nitrogen sensing.

WALK14 Plays a Role in Senescence.

Figure 5C:
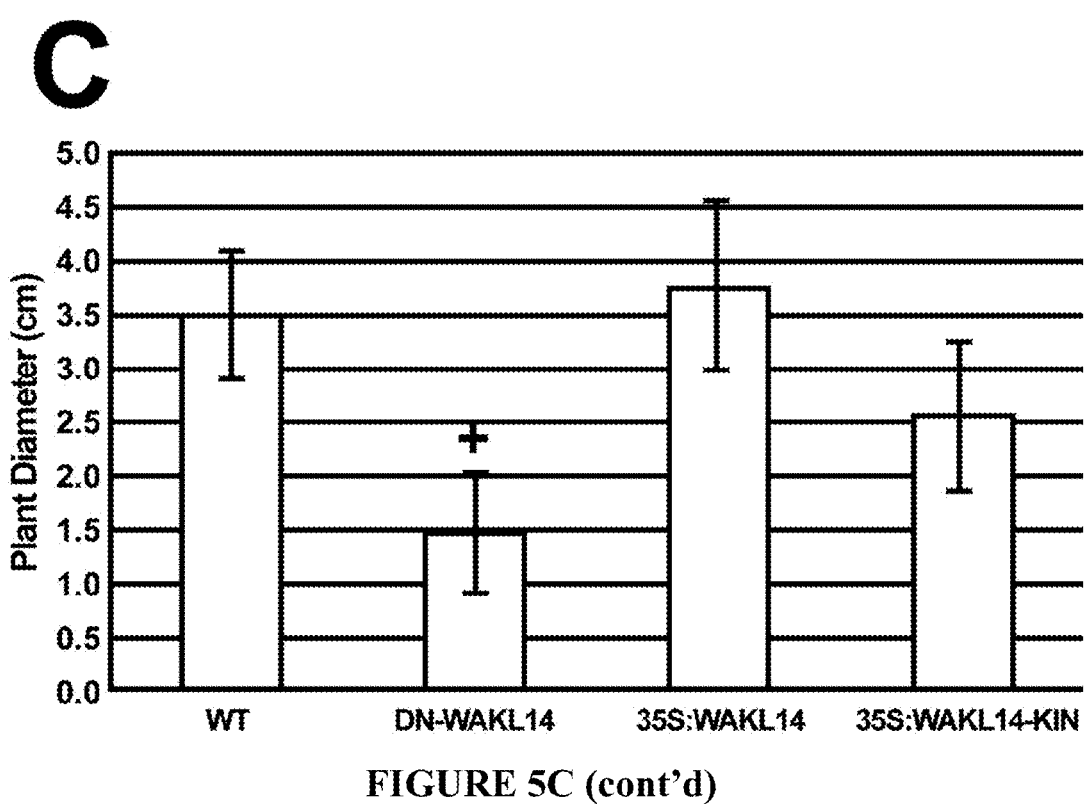

WAKL14 was identified as a gene of interest because independent DN-WAKL14 lines in the T2 generation displayed increased leaf senescence relative to the wild type. Leaf senescence is a developmentally controlled response to redistribute nutrients to the newly growing plant organs (Hajouj et al., 2000). Because DN-WAKL14 seedlings exhibited sensitivity to both nitrogen and sucrose deprivation it was proposed that the observed senescence could be a function of the loss of WAKL14 signaling. DN-WAKL14, 35S:WAKL14 and 35S:WAKL14 KIN were grown under low light conditions to maturity and found that DN-WAKL14 plants were significantly (p<0.01) smaller in diameter and had fewer leaves than the wild type (FIG. 5). Neither 35S:WAKL14 nor 35S:WAKL KIN were significantly different in leaf number or plant size than wild type plants when grown on soil, but DN-WAKL14 were smaller and had fewer leaves (p<0.01). This shows that at low light levels DN-WAKL14 plants are drastically altered in nutrient utilization. There was also pronounced leaf senescence in the DN-WAKL14 plants that was not seen in the wild type or the other WAKL14 mutants. This further demonstrated WAKL14 functions in nutrient utilization in a manner linked to the developmental onset of senescence.

WAKL14 Regulates the Accumulation of Senescence-Related mRNAs.

Figure 6:
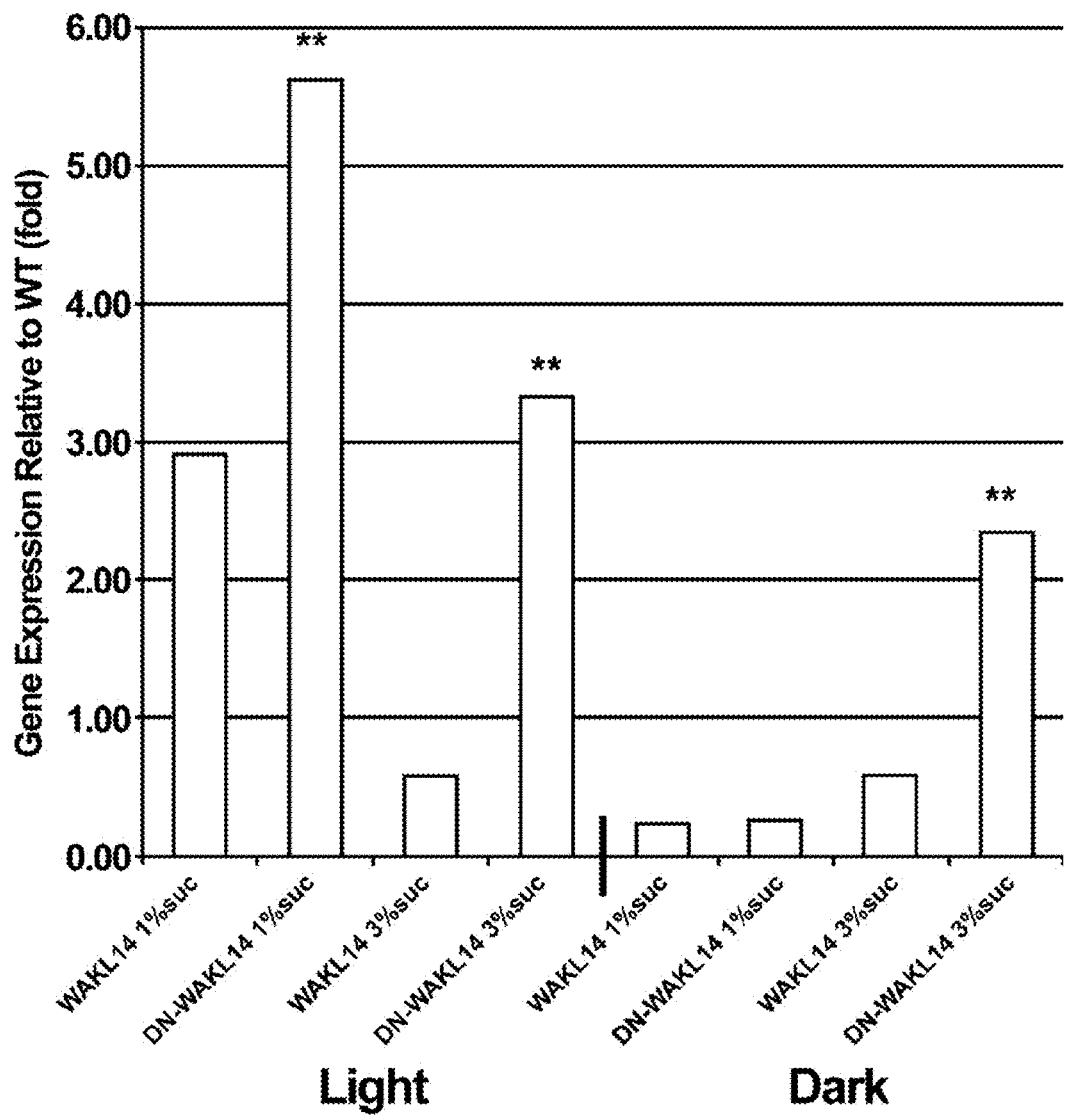
FIG. 6 show quantitative real-time PCR analysis of gene expression levels of SRG2/DIN2 for DN-WAKL14 and 35S:WAKL14 mutants compared to wild type gene expression in dark and light treated 10-day-old seedling grown on 1% and 3% sucrose MS media. Dark treated plants were first grown for 5 days under the same 16 h light and 8 h dark cycles as the light treated plants and then covered in foil for the remaining 5 days before RNA isolation. This tissue was pooled from three different plates. Data analysis was done using three independent Ct values for each measurement. **=p-value<0.005.

To ascertain a potential mechanism for the observed senescence phenotype in DN-WAKL14 and 35S:WAKL14 senescence associated gene expression were analyzed in seedlings grown with increased sucrose (3%) and standard MS conditions and in the light and dark. The most dramatic results were from the expression pattern of senescence related gene 2 (SRG2: also known as DIN2) (FIG. 6). This protein is similar to β-glucosidase and its expression is induced in both the dark and in senescing leaves and suppressed by sugar (Lee et al., 2007). SRG2 gene expression in the full length and the dominant negative have a similar trends under normal media conditions (1% sucrose) in the light or dark, but under increased sucrose (3%) the expression patterns are completely opposite with the full length having very low expression of SRG2 while the dominant negative have very high expression of SRG, especially in the light (see FIG. 3.2). The expression of other senescence associated genes, DIN6 and SEN1, was also examined and showed a similar pattern to SRG2. Plants overexpressing the full-length WAKL14 cDNA exhibited reduced expression of DIN6 and SEN1 in the light and on regular (1% sucrose) media, while DN-WAKL14 increased the expression of these genes in the dark, with SRG2 having a more dramatic expression change.

A number of embodiments of the invention have been described. Nevertheless, it will be understood that various modifications may be made without departing from the spirit and scope of the invention. Accordingly, other embodiments are within the scope of the following claims.

What is claimed is:

1. A method comprising introducing and expressing in a plant a polynucleotide that is operably linked to a constitutive promoter, wherein the polynucleotide encodes a polypeptide having at least 95% identity to SEQ ID NO:2, and wherein expression or over expression of the polypeptide in the plant results in tolerance to nitrogen and/or sucrose deficient growth.

2. The method according to claim 1, wherein the polynucleotide comprises a sequence that is at least 80% identical to SEQ ID NO:1.

3. The method according to claim 2, wherein the polynucleotide is overexpressed in a plant.

4. The method according to claim 2, wherein the polynucleotide comprises a sequence that is at least 95% identical to SEQ ID NO:1.

5. The method according to claim 4, wherein the polynucleotide comprises the sequence of SEQ ID NO:1.

6. A transgenic plant produced by the method according to claim 1 or 2.

7. A transgenic plant produced by the method of claim 1 or 2, wherein the transgenic plant overexpresses the polynucleotide and wherein the transgenic plant has improved growth on a nutrient deficient media.

8. A method for the production of a transgenic plant having increased yield or growth relative to a corresponding wild type plant on a nutrient deficient media, which method comprises: (i) introducing and expressing in a plant or plant cell a polynucleotide that comprises a sequence that encodes a polypeptide having at least 95% identity to SEQ ID NO:2; and (ii) cultivating the plant cell under conditions for promoting plant growth and development.

9. A transgenic plant having increased tolerance to nitrogen and/or sucrose deficient conditions relative to a corresponding wild type plant, said increased tolerance resulting from a polynucleotide that encodes a polypeptide having at least 95% identity to SEQ ID NO:2 introduced into said plant.

10. The transgenic plant according to claim 9, wherein said plant is a monocotyledonous plant, selected from the group consisting of sugar cane, rice, maize, wheat, barley, millet, rye, oats, triticale, and sorghum.

11. A transgenic plant part, or a transgenic plant cell, isolated from the transgenic plant of claim 6.

* * * * *

SEQUENCE LISTING

```
<160> NUMBER OF SEQ ID NOS: 30

<210> SEQ ID NO 1
<211> LENGTH: 2127
<212> TYPE: DNA
<213> ORGANISM: Arabidopsis thaliana
<220> FEATURE:
<221> NAME/KEY: CDS
<222> LOCATION: (1)..(2127)

<400> SEQUENCE: 1 atg ttg aga tcg att ttt gat ttc aat caa cgt tca acg aag atg gtg      48
Met Leu Arg Ser Ile Phe Asp Phe Asn Gln Arg Ser Thr Lys Met Val
1               5                   10                  15 atg att tct cat aag ttg gat ttg att ttg gtt ttc ata atc gta atc      96
Met Ile Ser His Lys Leu Asp Leu Ile Leu Val Phe Ile Ile Val Ile
            20                  25                  30 gga gga tct att ttc cga cga gtt tct gct aat ttc acc gta cct tgt     144
Gly Gly Ser Ile Phe Arg Arg Val Ser Ala Asn Phe Thr Val Pro Cys
        35                  40                  45
```

```
aac gga aga tgc ggt gga ttg act ctg cct tat cct ttc ggg ttt tca     192
Asn Gly Arg Cys Gly Gly Leu Thr Leu Pro Tyr Pro Phe Gly Phe Ser
 50              55                  60 aac ggt tgt tcg atc cga ttc gat tgc tct gcg gcg gag aaa ccg atg     240
Asn Gly Cys Ser Ile Arg Phe Asp Cys Ser Ala Ala Glu Lys Pro Met
65                  70                  75                  80 atc gga gac ttt tcc gtt caa aac gtg acg gaa aac agt ata ttt gtc     288
Ile Gly Asp Phe Ser Val Gln Asn Val Thr Glu Asn Ser Ile Phe Val
                    85                  90                  95 ggt ctc tct cac aat tgt act cgg aag att gaa gat atg aat ccg ctt     336
Gly Leu Ser His Asn Cys Thr Arg Lys Ile Glu Asp Met Asn Pro Leu
                100                 105                 110 ttc ggc gag aat ttc gca cca acg tcg gag aac agt ttc ttg atg gag     384
Phe Gly Glu Asn Phe Ala Pro Thr Ser Glu Asn Ser Phe Leu Met Glu
            115                 120                 125 aat tgt aac cgt acc acc gat ggt tgc tct atc aag cag aag ttt ctg     432
Asn Cys Asn Arg Thr Thr Asp Gly Cys Ser Ile Lys Gln Lys Phe Leu
130                 135                 140 gag aat gtg ctg aaa ctc aaa agt tgt gat gct act gga aac ata agt     480
Glu Asn Val Leu Lys Leu Lys Ser Cys Asp Ala Thr Gly Asn Ile Ser
145                 150                 155                 160 tgt ttt tct tta gat agt aat tcg agt tcg aag aac tca gct aag ttt     528
Cys Phe Ser Leu Asp Ser Asn Ser Ser Ser Lys Asn Ser Ala Lys Phe
                    165                 170                 175 ttc agt atg aag aca tta agg aac agc tcg tgt agt ttg ttg ttc tcg     576
Phe Ser Met Lys Thr Leu Arg Asn Ser Ser Cys Ser Leu Leu Phe Ser
                180                 185                 190 tcg ata gct ttc gag tct gta ggt gtg aat gcg ggt ata gcg tta gag     624
Ser Ile Ala Phe Glu Ser Val Gly Val Asn Ala Gly Ile Ala Leu Glu
            195                 200                 205 ttt gag cga gtt cgg tta ggt tgg tgg ctt aag gga ggt tgc gag agc     672
Phe Glu Arg Val Arg Leu Gly Trp Trp Leu Lys Gly Gly Cys Glu Ser
210                 215                 220 gga act tgc gcg gct aac acc gat tgt aca gac gtt gaa act cct cat     720
Gly Thr Cys Ala Ala Asn Thr Asp Cys Thr Asp Val Glu Thr Pro His
225                 230                 235                 240 gga tat gca gga cac cgg tgc tca tgt ctt gac ggt ttc cac ggt gac     768
Gly Tyr Ala Gly His Arg Cys Ser Cys Leu Asp Gly Phe His Gly Asp
                    245                 250                 255 gga tac acc aac cct tgc cag aga gca cta ccg gag tgc cgt ggt tcc     816
Gly Tyr Thr Asn Pro Cys Gln Arg Ala Leu Pro Glu Cys Arg Gly Ser
                260                 265                 270 aag ctc gtc tgg aga cat tgt aga tct aat ctt att act att gta gga     864
Lys Leu Val Trp Arg His Cys Arg Ser Asn Leu Ile Thr Ile Val Gly
            275                 280                 285 gga act gtt ggt gga gcg ttt tta cta gct gcc ttg gct ttt ttc ttc     912
Gly Thr Val Gly Gly Ala Phe Leu Leu Ala Ala Leu Ala Phe Phe Phe
290                 295                 300 ttt tgt aag cgg aga cgg tct act cct ttg aga agt cat tta agc gca     960
Phe Cys Lys Arg Arg Arg Ser Thr Pro Leu Arg Ser His Leu Ser Ala
305                 310                 315                 320 aag cgt ctt ttg tct gaa gct gca ggg aac tcg agt gtc gcc ttt ttc    1008
Lys Arg Leu Leu Ser Glu Ala Ala Gly Asn Ser Ser Val Ala Phe Phe
                    325                 330                 335 cct tac aag gaa atc gag aaa gcg aca gat ggt ttc tct gaa aag cag    1056
Pro Tyr Lys Glu Ile Glu Lys Ala Thr Asp Gly Phe Ser Glu Lys Gln
                340                 345                 350 aag tta gga ata ggt gca tat ggt acg gtc tat aga gga aag ctc caa    1104
Lys Leu Gly Ile Gly Ala Tyr Gly Thr Val Tyr Arg Gly Lys Leu Gln
            355                 360                 365
```

| | | |
|---|---|---|
| aat gat gaa tgg gtt gct atc aaa aga ctt aga cat aga gat tca gaa<br>Asn Asp Glu Trp Val Ala Ile Lys Arg Leu Arg His Arg Asp Ser Glu<br>370 375 380 | | 1152 |
| agt ctt gac caa gtc atg aat gag atc aag ctt ctt tcc tct gtg agt<br>Ser Leu Asp Gln Val Met Asn Glu Ile Lys Leu Leu Ser Ser Val Ser<br>385 390 395 400 | | 1200 |
| cac ccg aat ctt gtc cgt ctc tta gga tgt tgt ata gaa caa ggc gat<br>His Pro Asn Leu Val Arg Leu Leu Gly Cys Cys Ile Glu Gln Gly Asp<br>405 410 415 | | 1248 |
| cca gtt ctc gtt tat gag tac atg ccg aat gga act cta tct gaa cat<br>Pro Val Leu Val Tyr Glu Tyr Met Pro Asn Gly Thr Leu Ser Glu His<br>420 425 430 | | 1296 |
| cta caa aga gat aga ggg agt ggt ctt cca tgg acc ttg cgt ctc act<br>Leu Gln Arg Asp Arg Gly Ser Gly Leu Pro Trp Thr Leu Arg Leu Thr<br>435 440 445 | | 1344 |
| gtt gct act caa aca gct aaa gca atc gcg tat ctc cac tct tca atg<br>Val Ala Thr Gln Thr Ala Lys Ala Ile Ala Tyr Leu His Ser Ser Met<br>450 455 460 | | 1392 |
| aac cca ccg atc tat cac cgt gac atc aaa tct acc aat atc ctt ctt<br>Asn Pro Pro Ile Tyr His Arg Asp Ile Lys Ser Thr Asn Ile Leu Leu<br>465 470 475 480 | | 1440 |
| gat tat gat ttc aac tcc aaa gtt gcg gat ttc gga ctc tct aga ctg<br>Asp Tyr Asp Phe Asn Ser Lys Val Ala Asp Phe Gly Leu Ser Arg Leu<br>485 490 495 | | 1488 |
| gga atg acg gaa tct tct cac ata tca acg gct cct caa ggg act cct<br>Gly Met Thr Glu Ser Ser His Ile Ser Thr Ala Pro Gln Gly Thr Pro<br>500 505 510 | | 1536 |
| ggt tat ctt gac ccg cag tac cat caa tgc ttt cat ctc tct gat aag<br>Gly Tyr Leu Asp Pro Gln Tyr His Gln Cys Phe His Leu Ser Asp Lys<br>515 520 525 | | 1584 |
| agc gac gtc tac agc ttt gga gtc gtc ctt gcc gag att ata acg gga<br>Ser Asp Val Tyr Ser Phe Gly Val Val Leu Ala Glu Ile Ile Thr Gly<br>530 535 540 | | 1632 |
| ttg aaa gtc gtt gat ttc aca cgt cca cat acc gaa atc aac cta gcg<br>Leu Lys Val Val Asp Phe Thr Arg Pro His Thr Glu Ile Asn Leu Ala<br>545 550 555 560 | | 1680 |
| gct ctt gct gtt gac aaa atc ggg tca ggt tgt atc gat gag ata ata<br>Ala Leu Ala Val Asp Lys Ile Gly Ser Gly Cys Ile Asp Glu Ile Ile<br>565 570 575 | | 1728 |
| gac ccg att ctt gac ttg gat ctc gac gca tgg act ctc tca tcc ata<br>Asp Pro Ile Leu Asp Leu Asp Leu Asp Ala Trp Thr Leu Ser Ser Ile<br>580 585 590 | | 1776 |
| cac acg gtg gct gag ctt gca ttt cga tgc tta gcc ttc cac agt gac<br>His Thr Val Ala Glu Leu Ala Phe Arg Cys Leu Ala Phe His Ser Asp<br>595 600 605 | | 1824 |
| atg aga ccg aca atg acc gaa gta gcg gac gag ctt gaa cag ata aga<br>Met Arg Pro Thr Met Thr Glu Val Ala Asp Glu Leu Glu Gln Ile Arg<br>610 615 620 | | 1872 |
| ctc agt ggt tgg att cca agc atg agc ttg gat tca cca gcc ggt tct<br>Leu Ser Gly Trp Ile Pro Ser Met Ser Leu Asp Ser Pro Ala Gly Ser<br>625 630 635 640 | | 1920 |
| ctc cgt tca tct gat cga gga agc gaa aga tca gtt aaa caa tca tca<br>Leu Arg Ser Ser Asp Arg Gly Ser Glu Arg Ser Val Lys Gln Ser Ser<br>645 650 655 | | 1968 |
| ata gga agc aga aga gtc gtt atc cct cag aaa caa cct gat tgc ctc<br>Ile Gly Ser Arg Arg Val Val Ile Pro Gln Lys Gln Pro Asp Cys Leu<br>660 665 670 | | 2016 |
| gca tcc gtc gaa gag att agc gat agc tca ccc atc tca gtt caa gat<br>Ala Ser Val Glu Glu Ile Ser Asp Ser Ser Pro Ile Ser Val Gln Asp<br>675 680 685 | | 2064 |

-continued

```
cct tgg tta agt gca caa agc tca ccg tct aca aat aca ttg ctc ggt      2112
Pro Trp Leu Ser Ala Gln Ser Ser Pro Ser Thr Asn Thr Leu Leu Gly
    690             695                 700 aac att cca aga tga                                                   2127
Asn Ile Pro Arg
705

<210> SEQ ID NO 2
<211> LENGTH: 708
<212> TYPE: PRT
<213> ORGANISM: Arabidopsis thaliana

<400> SEQUENCE: 2

Met Leu Arg Ser Ile Phe Asp Phe Asn Gln Arg Ser Thr Lys Met Val
1               5                   10                  15

Met Ile Ser His Lys Leu Asp Leu Ile Leu Val Phe Ile Ile Val Ile
            20                  25                  30

Gly Gly Ser Ile Phe Arg Arg Val Ser Ala Asn Phe Thr Val Pro Cys
        35                  40                  45

Asn Gly Arg Cys Gly Gly Leu Thr Leu Pro Tyr Pro Phe Gly Phe Ser
    50                  55                  60

Asn Gly Cys Ser Ile Arg Phe Asp Cys Ser Ala Ala Glu Lys Pro Met
65                  70                  75                  80

Ile Gly Asp Phe Ser Val Gln Asn Val Thr Glu Asn Ser Ile Phe Val
                85                  90                  95

Gly Leu Ser His Asn Cys Thr Arg Lys Ile Glu Asp Met Asn Pro Leu
            100                 105                 110

Phe Gly Glu Asn Phe Ala Pro Thr Ser Glu Asn Ser Phe Leu Met Glu
        115                 120                 125

Asn Cys Asn Arg Thr Thr Asp Gly Cys Ser Ile Lys Gln Lys Phe Leu
    130                 135                 140

Glu Asn Val Leu Lys Leu Lys Ser Cys Asp Ala Thr Gly Asn Ile Ser
145                 150                 155                 160

Cys Phe Ser Leu Asp Ser Asn Ser Ser Lys Asn Ser Ala Lys Phe
                165                 170                 175

Phe Ser Met Lys Thr Leu Arg Asn Ser Ser Cys Ser Leu Leu Phe Ser
            180                 185                 190

Ser Ile Ala Phe Glu Ser Val Gly Val Asn Ala Gly Ile Ala Leu Glu
        195                 200                 205

Phe Glu Arg Val Arg Leu Gly Trp Trp Leu Lys Gly Gly Cys Glu Ser
    210                 215                 220

Gly Thr Cys Ala Ala Asn Thr Asp Cys Thr Asp Val Glu Thr Pro His
225                 230                 235                 240

Gly Tyr Ala Gly His Arg Cys Ser Cys Leu Asp Gly Phe His Gly Asp
                245                 250                 255

Gly Tyr Thr Asn Pro Cys Gln Arg Ala Leu Pro Glu Cys Arg Gly Ser
            260                 265                 270

Lys Leu Val Trp Arg His Cys Arg Ser Asn Leu Ile Thr Ile Val Gly
        275                 280                 285

Gly Thr Val Gly Gly Ala Phe Leu Leu Ala Ala Leu Ala Phe Phe Phe
    290                 295                 300

Phe Cys Lys Arg Arg Arg Ser Thr Pro Leu Arg Ser His Leu Ser Ala
305                 310                 315                 320

Lys Arg Leu Leu Ser Glu Ala Ala Gly Asn Ser Ser Val Ala Phe Phe
                325                 330                 335
```

```
Pro Tyr Lys Glu Ile Glu Lys Ala Thr Asp Gly Phe Ser Glu Lys Gln
            340                 345                 350

Lys Leu Gly Ile Gly Ala Tyr Gly Thr Val Tyr Arg Gly Lys Leu Gln
        355                 360                 365

Asn Asp Glu Trp Val Ala Ile Lys Arg Leu Arg His Arg Asp Ser Glu
    370                 375                 380

Ser Leu Asp Gln Val Met Asn Glu Ile Lys Leu Leu Ser Ser Val Ser
385                 390                 395                 400

His Pro Asn Leu Val Arg Leu Leu Gly Cys Cys Ile Glu Gln Gly Asp
                405                 410                 415

Pro Val Leu Val Tyr Glu Tyr Met Pro Asn Gly Thr Leu Ser Glu His
            420                 425                 430

Leu Gln Arg Asp Arg Gly Ser Gly Leu Pro Trp Thr Leu Arg Leu Thr
        435                 440                 445

Val Ala Thr Gln Thr Ala Lys Ala Ile Ala Tyr Leu His Ser Ser Met
    450                 455                 460

Asn Pro Pro Ile Tyr His Arg Asp Ile Lys Ser Thr Asn Ile Leu Leu
465                 470                 475                 480

Asp Tyr Asp Phe Asn Ser Lys Val Ala Asp Phe Gly Leu Ser Arg Leu
                485                 490                 495

Gly Met Thr Glu Ser Ser His Ile Ser Thr Ala Pro Gln Gly Thr Pro
            500                 505                 510

Gly Tyr Leu Asp Pro Gln Tyr His Gln Cys Phe His Leu Ser Asp Lys
        515                 520                 525

Ser Asp Val Tyr Ser Phe Gly Val Val Leu Ala Glu Ile Ile Thr Gly
    530                 535                 540

Leu Lys Val Val Asp Phe Thr Arg Pro His Thr Glu Ile Asn Leu Ala
545                 550                 555                 560

Ala Leu Ala Val Asp Lys Ile Gly Ser Gly Cys Ile Asp Glu Ile Ile
                565                 570                 575

Asp Pro Ile Leu Asp Leu Asp Leu Asp Ala Trp Thr Leu Ser Ser Ile
            580                 585                 590

His Thr Val Ala Glu Leu Ala Phe Arg Cys Leu Ala Phe His Ser Asp
        595                 600                 605

Met Arg Pro Thr Met Thr Glu Val Ala Asp Glu Leu Glu Gln Ile Arg
    610                 615                 620

Leu Ser Gly Trp Ile Pro Ser Met Ser Leu Asp Ser Pro Ala Gly Ser
625                 630                 635                 640

Leu Arg Ser Ser Asp Arg Gly Ser Glu Arg Ser Val Lys Gln Ser Ser
                645                 650                 655

Ile Gly Ser Arg Arg Val Val Ile Pro Gln Lys Gln Pro Asp Cys Leu
            660                 665                 670

Ala Ser Val Glu Glu Ile Ser Asp Ser Pro Ile Ser Val Gln Asp
        675                 680                 685

Pro Trp Leu Ser Ala Gln Ser Ser Pro Ser Thr Asn Thr Leu Leu Gly
    690                 695                 700

Asn Ile Pro Arg
705

<210> SEQ ID NO 3
<211> LENGTH: 2112
<212> TYPE: DNA
<213> ORGANISM: Lycopersicon esculentum
<220> FEATURE:
<221> NAME/KEY: CDS
<222> LOCATION: (1)..(2112)
```

```
<220> FEATURE:
<221> NAME/KEY: misc_feature
<222> LOCATION: (1863)..(1863)
<223> OTHER INFORMATION: n is a, c, g, or t

<400> SEQUENCE: 3 atg ggt ttt cat cac atc att att att aga ttc gtt ttc tca att tta    48
Met Gly Phe His His Ile Ile Ile Ile Arg Phe Val Phe Ser Ile Leu
1               5                   10                  15 ttg ggt tgg tta tca tcg tca gtt gag gct act aat tca act aag tgc    96
Leu Gly Trp Leu Ser Ser Ser Val Glu Ala Thr Asn Ser Thr Lys Cys
            20                  25                  30 aat cag tac tgt gga gct gct ggt tct tat agt ccg cgt gtt tcg tat   144
Asn Gln Tyr Cys Gly Ala Ala Gly Ser Tyr Ser Pro Arg Val Ser Tyr
        35                  40                  45 cca ttt gga ttc tca gag ggt tgt ggg att cgt tta gac tgt act gaa   192
Pro Phe Gly Phe Ser Glu Gly Cys Gly Ile Arg Leu Asp Cys Thr Glu
    50                  55                  60 agt act gga gaa atc aga att ggg gaa tat ata ata cag aat gtg act   240
Ser Thr Gly Glu Ile Arg Ile Gly Glu Tyr Ile Ile Gln Asn Val Thr
65                  70                  75                  80 tca gag act ctg atg gtt aac ttc tcg atg aat tgc agc cgt ccg att   288
Ser Glu Thr Leu Met Val Asn Phe Ser Met Asn Cys Ser Arg Pro Ile
                85                  90                  95 gag gat cta cag caa ttt gat cga acc aac ttt ggt atg act tgg aga   336
Glu Asp Leu Gln Gln Phe Asp Arg Thr Asn Phe Gly Met Thr Trp Arg
            100                 105                 110 aat gga ctg ctt cta cac aat tgc aaa gta ccg aag agc gaa tgt acc   384
Asn Gly Leu Leu Leu His Asn Cys Lys Val Pro Lys Ser Glu Cys Thr
        115                 120                 125 ata cca tcg gaa att tta agc acg cgt ttg aac ata cag tca tgt gat   432
Ile Pro Ser Glu Ile Leu Ser Thr Arg Leu Asn Ile Gln Ser Cys Asp
    130                 135                 140 tcg aag aag gag aat gtc agt tgt tat tct gag gcg agg gcg gat tat   480
Ser Lys Lys Glu Asn Val Ser Cys Tyr Ser Glu Ala Arg Ala Asp Tyr
145                 150                 155                 160 tta gat tac cag aaa ttg aag aat aca ggg tgt gga act gtg att tcg   528
Leu Asp Tyr Gln Lys Leu Lys Asn Thr Gly Cys Gly Thr Val Ile Ser
                165                 170                 175 tcc atc ttg att ggt atg gat aat gat aca atg aag agt tct gcc atg   576
Ser Ile Leu Ile Gly Met Asp Asn Asp Thr Met Lys Ser Ser Ala Met
            180                 185                 190 ttt atc gag ttt cag acg atg gaa tta gcg tgg gga ttg gaa ggg gat   624
Phe Ile Glu Phe Gln Thr Met Glu Leu Ala Trp Gly Leu Glu Gly Asp
        195                 200                 205 tgt gca tgt cat aac gat gca aat tgt acc aac gtt tct ctc ccg ggg   672
Cys Ala Cys His Asn Asp Ala Asn Cys Thr Asn Val Ser Leu Pro Gly
    210                 215                 220 aac cga aaa ggt ttc cgg tgc cgg tgt aaa gat gga ttc gtc ggt gat   720
Asn Arg Lys Gly Phe Arg Cys Arg Cys Lys Asp Gly Phe Val Gly Asp
225                 230                 235                 240 ggc ttc agc gac ggt gat ggc tgc cgg aaa gtt tca aga tgt aat cct   768
Gly Phe Ser Asp Gly Asp Gly Cys Arg Lys Val Ser Arg Cys Asn Pro
                245                 250                 255 tcc aga tac ctc tct gga cga tgt ggt gga act acc aga att ggt gtg   816
Ser Arg Tyr Leu Ser Gly Arg Cys Gly Gly Thr Thr Arg Ile Gly Val
            260                 265                 270 ctc gtt gga ggg att att gct gga gct ggt tta atg gct gct ttg gct   864
Leu Val Gly Gly Ile Ile Ala Gly Ala Gly Leu Met Ala Ala Leu Ala
        275                 280                 285 gtt ctt tgc tac tgc att cga aga cgt tct gca tct ctc aag aaa aga   912
```

```
                Val Leu Cys Tyr Cys Ile Arg Arg Arg Ser Ala Ser Leu Lys Lys Arg
                    290                 295                 300 atg agc gca aga cgc ctt ctc tct gaa gct gca ggc agc aac agt gtt         960
Met Ser Ala Arg Arg Leu Leu Ser Glu Ala Ala Gly Ser Asn Ser Val
305                 310                 315                 320 cat gta ttt caa tac aaa gaa att gag aga gca aca aat agt ttc tct        1008
His Val Phe Gln Tyr Lys Glu Ile Glu Arg Ala Thr Asn Ser Phe Ser
                325                 330                 335 gag aaa cag agg ctg ggc ata ggg gct tat ggc aca gtt tat gct gga        1056
Glu Lys Gln Arg Leu Gly Ile Gly Ala Tyr Gly Thr Val Tyr Ala Gly
            340                 345                 350 aag ctc cac agt gat gaa tgg gtt gca att aag aaa cta aga cac cgg        1104
Lys Leu His Ser Asp Glu Trp Val Ala Ile Lys Lys Leu Arg His Arg
        355                 360                 365 gat ccg gat ggt gtt gaa caa gtg atg aat gag gtt aag ctt ttg tct        1152
Asp Pro Asp Gly Val Glu Gln Val Met Asn Glu Val Lys Leu Leu Ser
370                 375                 380 tct gta agt cat cca aac tta gtc cgc ctc ttg ggt tgt tgt ata gaa        1200
Ser Val Ser His Pro Asn Leu Val Arg Leu Leu Gly Cys Cys Ile Glu
385                 390                 395                 400 aat ggt gaa cag att ctt gtt tat gaa ttt atg ccc aac gga act cta        1248
Asn Gly Glu Gln Ile Leu Val Tyr Glu Phe Met Pro Asn Gly Thr Leu
                405                 410                 415 gct cag cat cta cag aga gaa agg agt tca gga ctt ccg tgg aca ata        1296
Ala Gln His Leu Gln Arg Glu Arg Ser Ser Gly Leu Pro Trp Thr Ile
            420                 425                 430 cgt ctc act atc gca aca gaa act gct cat gcg att gct cac ctt cac        1344
Arg Leu Thr Ile Ala Thr Glu Thr Ala His Ala Ile Ala His Leu His
        435                 440                 445 tca gca atg aat cca cca ata tac cac agg gat atc aaa tca agt aac        1392
Ser Ala Met Asn Pro Pro Ile Tyr His Arg Asp Ile Lys Ser Ser Asn
450                 455                 460 ata cta ttg gat tac aac ttc aac tca aaa gtt gca gac ttt ggt ctt        1440
Ile Leu Leu Asp Tyr Asn Phe Asn Ser Lys Val Ala Asp Phe Gly Leu
465                 470                 475                 480 tcc aga ttt ggc atg aca gat gat tcc cac att tct aca gca cca caa        1488
Ser Arg Phe Gly Met Thr Asp Asp Ser His Ile Ser Thr Ala Pro Gln
                485                 490                 495 ggt act cca ggt tat gtg gat cct cag tac cat cag aat tac cat ctt        1536
Gly Thr Pro Gly Tyr Val Asp Pro Gln Tyr His Gln Asn Tyr His Leu
            500                 505                 510 tcc gat aag agt gat gtg tac agc ttc ggg gtg gtt ctt gta gaa atc        1584
Ser Asp Lys Ser Asp Val Tyr Ser Phe Gly Val Val Leu Val Glu Ile
        515                 520                 525 att aca gca atg aaa gtg gtt gat ttc tct aga tca cac agt gag att        1632
Ile Thr Ala Met Lys Val Val Asp Phe Ser Arg Ser His Ser Glu Ile
530                 535                 540 aat ttg gct gca ctt gca ata gac aga ata ggt aag ggt cgt gtg gat        1680
Asn Leu Ala Ala Leu Ala Ile Asp Arg Ile Gly Lys Gly Arg Val Asp
545                 550                 555                 560 gag atc atc gat cca ttt cta gag cca cac aga gat gca tgg act cta        1728
Glu Ile Ile Asp Pro Phe Leu Glu Pro His Arg Asp Ala Trp Thr Leu
                565                 570                 575 tca tca gtt cat aga gtt gca gag ctt gct ttt aga tgc ctt gca ttt        1776
Ser Ser Val His Arg Val Ala Glu Leu Ala Phe Arg Cys Leu Ala Phe
            580                 585                 590 cat agg gat atg agg cct tca atg aca gaa gtg gca gac gag ctg gaa        1824
His Arg Asp Met Arg Pro Ser Met Thr Glu Val Ala Asp Glu Leu Glu
        595                 600                 605 cag atc agg ctc agc agt tgg gca tca ttg gag gac aan gta tgc atg        1872
```

-continued

```
Gln Ile Arg Leu Ser Ser Trp Ala Ser Leu Glu Asp Xaa Val Cys Met
    610                 615                 620 act tca tca gtg aat tcg tct tgc tca tct ccc cgt cgc agg agt gag      1920
Thr Ser Ser Val Asn Ser Ser Cys Ser Ser Pro Arg Arg Arg Ser Glu
625                 630                 635                 640 aca tct ttt ctt tgt tca aca act aag aaa gga gta ggg agt agg agg      1968
Thr Ser Phe Leu Cys Ser Thr Thr Lys Lys Gly Val Gly Ser Arg Arg
            645                 650                 655 ttg att gtt ccc ctt ccc cta gag aat tca ctg gca ctc gtg gag gaa      2016
Leu Ile Val Pro Leu Pro Leu Glu Asn Ser Leu Ala Leu Val Glu Glu
        660                 665                 670 ata aaa aac agt tcc cct gtt tct gtt cag gat cct ggg tta agt gaa      2064
Ile Lys Asn Ser Ser Pro Val Ser Val Gln Asp Pro Gly Leu Ser Glu
    675                 680                 685 gag agt ccc cct tcc ccc aat cga tta tta ggt aat tct ggt cga tga      2112
Glu Ser Pro Pro Ser Pro Asn Arg Leu Leu Gly Asn Ser Gly Arg
690                 695                 700
```

<210> SEQ ID NO 4
<211> LENGTH: 703
<212> TYPE: PRT
<213> ORGANISM: Lycopersicon esculentum
<220> FEATURE:
<221> NAME/KEY: misc_feature
<222> LOCATION: (621)..(621)
<223> OTHER INFORMATION: The 'Xaa' at location 621 stands for Lys, or Asn.

<400> SEQUENCE: 4

```
Met Gly Phe His His Ile Ile Ile Arg Phe Val Phe Ser Ile Leu
1               5                   10                  15

Leu Gly Trp Leu Ser Ser Ser Val Glu Ala Thr Asn Ser Thr Lys Cys
            20                  25                  30

Asn Gln Tyr Cys Gly Ala Ala Gly Ser Tyr Ser Pro Arg Val Ser Tyr
        35                  40                  45

Pro Phe Gly Phe Ser Glu Gly Cys Gly Ile Arg Leu Asp Cys Thr Glu
    50                  55                  60

Ser Thr Gly Glu Ile Arg Ile Gly Glu Tyr Ile Ile Gln Asn Val Thr
65                  70                  75                  80

Ser Glu Thr Leu Met Val Asn Phe Ser Met Asn Cys Ser Arg Pro Ile
                85                  90                  95

Glu Asp Leu Gln Gln Phe Asp Arg Thr Asn Phe Gly Met Thr Trp Arg
            100                 105                 110

Asn Gly Leu Leu Leu His Asn Cys Lys Val Pro Lys Ser Glu Cys Thr
        115                 120                 125

Ile Pro Ser Glu Ile Leu Ser Thr Arg Leu Asn Ile Gln Ser Cys Asp
    130                 135                 140

Ser Lys Lys Glu Asn Val Ser Cys Tyr Ser Glu Ala Arg Ala Asp Tyr
145                 150                 155                 160

Leu Asp Tyr Gln Lys Leu Lys Asn Thr Gly Cys Gly Thr Val Ile Ser
                165                 170                 175

Ser Ile Leu Ile Gly Met Asp Asn Asp Thr Met Lys Ser Ala Met
            180                 185                 190

Phe Ile Glu Phe Gln Thr Met Glu Leu Ala Trp Gly Leu Glu Gly Asp
        195                 200                 205

Cys Ala Cys His Asn Asp Ala Asn Cys Thr Asn Val Ser Leu Pro Gly
    210                 215                 220

Asn Arg Lys Gly Phe Arg Cys Arg Cys Lys Asp Gly Phe Val Gly Asp
225                 230                 235                 240
```

```
Gly Phe Ser Asp Gly Asp Gly Cys Arg Lys Val Ser Arg Cys Asn Pro
                245                 250                 255

Ser Arg Tyr Leu Ser Gly Arg Cys Gly Gly Thr Thr Arg Ile Gly Val
            260                 265                 270

Leu Val Gly Gly Ile Ile Ala Gly Ala Gly Leu Met Ala Ala Leu Ala
        275                 280                 285

Val Leu Cys Tyr Cys Ile Arg Arg Ser Ala Ser Leu Lys Lys Arg
    290                 295                 300

Met Ser Ala Arg Arg Leu Leu Ser Glu Ala Ala Gly Ser Asn Ser Val
305                 310                 315                 320

His Val Phe Gln Tyr Lys Glu Ile Glu Arg Ala Thr Asn Ser Phe Ser
                325                 330                 335

Glu Lys Gln Arg Leu Gly Ile Gly Ala Tyr Gly Thr Val Tyr Ala Gly
            340                 345                 350

Lys Leu His Ser Asp Glu Trp Val Ala Ile Lys Lys Leu Arg His Arg
        355                 360                 365

Asp Pro Asp Gly Val Glu Gln Val Met Asn Glu Val Lys Leu Leu Ser
    370                 375                 380

Ser Val Ser His Pro Asn Leu Val Arg Leu Leu Gly Cys Cys Ile Glu
385                 390                 395                 400

Asn Gly Glu Gln Ile Leu Val Tyr Glu Phe Met Pro Asn Gly Thr Leu
                405                 410                 415

Ala Gln His Leu Gln Arg Glu Arg Ser Ser Gly Leu Pro Trp Thr Ile
            420                 425                 430

Arg Leu Thr Ile Ala Thr Glu Thr Ala His Ala Ile Ala His Leu His
        435                 440                 445

Ser Ala Met Asn Pro Pro Ile Tyr His Arg Asp Ile Lys Ser Ser Asn
    450                 455                 460

Ile Leu Leu Asp Tyr Asn Phe Asn Ser Lys Val Ala Asp Phe Gly Leu
465                 470                 475                 480

Ser Arg Phe Gly Met Thr Asp Asp Ser His Ile Ser Thr Ala Pro Gln
                485                 490                 495

Gly Thr Pro Gly Tyr Val Asp Pro Gln Tyr His Gln Asn Tyr His Leu
            500                 505                 510

Ser Asp Lys Ser Asp Val Tyr Ser Phe Gly Val Val Leu Val Glu Ile
        515                 520                 525

Ile Thr Ala Met Lys Val Val Asp Phe Ser Arg Ser His Ser Glu Ile
    530                 535                 540

Asn Leu Ala Ala Leu Ala Ile Asp Arg Ile Gly Lys Gly Arg Val Asp
545                 550                 555                 560

Glu Ile Ile Asp Pro Phe Leu Glu Pro His Arg Asp Ala Trp Thr Leu
                565                 570                 575

Ser Ser Val His Arg Val Ala Glu Leu Ala Phe Arg Cys Leu Ala Phe
            580                 585                 590

His Arg Asp Met Arg Pro Ser Met Thr Glu Val Ala Asp Glu Leu Glu
        595                 600                 605

Gln Ile Arg Leu Ser Ser Trp Ala Ser Leu Glu Asp Xaa Val Cys Met
    610                 615                 620

Thr Ser Ser Val Asn Ser Ser Cys Ser Ser Pro Arg Arg Arg Ser Glu
625                 630                 635                 640

Thr Ser Phe Leu Cys Ser Thr Thr Lys Lys Gly Val Gly Ser Arg Arg
                645                 650                 655

Leu Ile Val Pro Leu Pro Leu Glu Asn Ser Leu Ala Leu Val Glu Glu
```

```
                         660                 665                 670
Ile Lys Asn Ser Ser Pro Val Ser Val Gln Asp Pro Gly Leu Ser Glu
                675                 680                 685

Glu Ser Pro Pro Ser Pro Asn Arg Leu Leu Gly Asn Ser Gly Arg
        690                 695                 700

<210> SEQ ID NO 5
<211> LENGTH: 2037
<212> TYPE: DNA
<213> ORGANISM: Vitis vinifera
<220> FEATURE:
<221> NAME/KEY: CDS
<222> LOCATION: (1)..(2037)

<400> SEQUENCE: 5 atg agg aag gct ctt caa cga acg att ctc gct ctc atc tgt acg gtt      48
Met Arg Lys Ala Leu Gln Arg Thr Ile Leu Ala Leu Ile Cys Thr Val
1               5                   10                  15 acc ctc gtc tct gca atc aag aat gac tcc tgt gga acc ggg aaa tct      96
Thr Leu Val Ser Ala Ile Lys Asn Asp Ser Cys Gly Thr Gly Lys Ser
            20                  25                  30 gct aaa cga gtc cat tat cca ttt ggg ttc tca tcc gat agc cca atc     144
Ala Lys Arg Val His Tyr Pro Phe Gly Phe Ser Ser Asp Ser Pro Ile
        35                  40                  45 aaa ctg aac tgc agc aaa gaa ggg gag atc gaa ata caa aat ttt aaa     192
Lys Leu Asn Cys Ser Lys Glu Gly Glu Ile Glu Ile Gln Asn Phe Lys
    50                  55                  60 gtc cag aat gta acc aca gac agc atc atc atc aat cta cca gcg cag     240
Val Gln Asn Val Thr Thr Asp Ser Ile Ile Ile Asn Leu Pro Ala Gln
65                  70                  75                  80 tgc cag cgt gag atc caa aag atc gag cca cta ttc ggt aaa aac tac     288
Cys Gln Arg Glu Ile Gln Lys Ile Glu Pro Leu Phe Gly Lys Asn Tyr
                85                  90                  95 gcg ctg agt tcg aag aac agt ctt ctc ttc cag aat tgt agc tcg tcg     336
Ala Leu Ser Ser Lys Asn Ser Leu Leu Phe Gln Asn Cys Ser Ser Ser
            100                 105                 110 tct tcc ggg tgc gtg ata ccc acg agt gtg ttc aac ggc cag aac aag     384
Ser Ser Gly Cys Val Ile Pro Thr Ser Val Phe Asn Gly Gln Asn Lys
        115                 120                 125 ttg aac aat tgc aat ggc aaa agc gac aac aac ata agc tgc ttt ccg     432
Leu Asn Asn Cys Asn Gly Lys Ser Asp Asn Asn Ile Ser Cys Phe Pro
    130                 135                 140 cta gat tct gag tcc gag ttt atg agt ttt gcg aac gtg act ggg act     480
Leu Asp Ser Glu Ser Glu Phe Met Ser Phe Ala Asn Val Thr Gly Thr
145                 150                 155                 160 ggg tgc aag ttt ttg tta ctt tcc atg gcg gtt gag tgg agg aac aac     528
Gly Cys Lys Phe Leu Leu Leu Ser Met Ala Val Glu Trp Arg Asn Asn
                165                 170                 175 tcc gca gtt tcg ctg gag ttg gga acg gct cag ttg ggg tgg tgg ctg     576
Ser Ala Val Ser Leu Glu Leu Gly Thr Ala Gln Leu Gly Trp Trp Leu
            180                 185                 190 gac cat ccg tgc cat tgc gct ccg aat gcg aaa cat acc aat tta act     624
Asp His Pro Cys His Cys Ala Pro Asn Ala Lys His Thr Asn Leu Thr
        195                 200                 205 gtt ccc ggg ggt ttc ggt tgc cgt tgc agc tgc aag gaa gga ttc gac     672
Val Pro Gly Gly Phe Gly Cys Arg Cys Ser Cys Lys Glu Gly Phe Asp
    210                 215                 220 gga gat gga ttt aaa gat ggc gat ggt tgt cag gaa gtt aca gat tgc     720
Gly Asp Gly Phe Lys Asp Gly Asp Gly Cys Gln Glu Val Thr Asp Cys
225                 230                 235                 240 aat gcg tca aag tac atg tcg ggc aca tgt gga gga act aca agg gtt     768
```

-continued

| | | |
|---|---|---|
| Asn Ala Ser Lys Tyr Met Ser Gly Thr Cys Gly Gly Thr Thr Arg Val<br>245 250 255 | | |
| gct gtt ctt gtt gga ggt gtc att gtt gga gct tct tta atg agc act<br>Ala Val Leu Val Gly Gly Val Ile Val Gly Ala Ser Leu Met Ser Thr<br>260 265 270 | 816 | |
| gtg gct ctt atc tgc tac tgt att cga cga cgt tct tat ttg agg agg<br>Val Ala Leu Ile Cys Tyr Cys Ile Arg Arg Arg Ser Tyr Leu Arg Arg<br>275 280 285 | 864 | |
| cgt atg agt gca aaa cgc ctt ata tgt gaa gct gca ggc aac tcc agt<br>Arg Met Ser Ala Lys Arg Leu Ile Cys Glu Ala Ala Gly Asn Ser Ser<br>290 295 300 | 912 | |
| gtt cct ctc tat ccc tac aaa gaa gtt gaa agg gcc acc aat ggc ttc<br>Val Pro Leu Tyr Pro Tyr Lys Glu Val Glu Arg Ala Thr Asn Gly Phe<br>305 310 315 320 | 960 | |
| tca gag aaa caa aga ctt gga act ggg gca tat ggt aca gtt ttt gca<br>Ser Glu Lys Gln Arg Leu Gly Thr Gly Ala Tyr Gly Thr Val Phe Ala<br>325 330 335 | 1008 | |
| gga aag ctc cac aat gat gaa tgg gtt gcc att aaa aag atc aga aat<br>Gly Lys Leu His Asn Asp Glu Trp Val Ala Ile Lys Lys Ile Arg Asn<br>340 345 350 | 1056 | |
| cgt gat aat gac agc att gag caa gtc atg aat gaa atc aag ctg atc<br>Arg Asp Asn Asp Ser Ile Glu Gln Val Met Asn Glu Ile Lys Leu Ile<br>355 360 365 | 1104 | |
| tct tct gtg aat cat cca aat cta gtg cgc cta tta ggt tgc tgt ata<br>Ser Ser Val Asn His Pro Asn Leu Val Arg Leu Leu Gly Cys Cys Ile<br>370 375 380 | 1152 | |
| gag aat ggt gaa cag atc ctt gtc tat gaa ttc atg gcc aat gga act<br>Glu Asn Gly Glu Gln Ile Leu Val Tyr Glu Phe Met Ala Asn Gly Thr<br>385 390 395 400 | 1200 | |
| cta tct cag cac cta cag aaa gag agg ggc aaa ggt ctt cca tgg aca<br>Leu Ser Gln His Leu Gln Lys Glu Arg Gly Lys Gly Leu Pro Trp Thr<br>405 410 415 | 1248 | |
| aca agg ctc aac att gcc acc gaa aca gct aat gct att gcc cat ctc<br>Thr Arg Leu Asn Ile Ala Thr Glu Thr Ala Asn Ala Ile Ala His Leu<br>420 425 430 | 1296 | |
| cac tca gcc atc act cct cca att ttc cac aga gac ata aag tcc agt<br>His Ser Ala Ile Thr Pro Pro Ile Phe His Arg Asp Ile Lys Ser Ser<br>435 440 445 | 1344 | |
| aat ata ctt ctg gat gac aac ttc aac tca aag gta gca gat ttt ggt<br>Asn Ile Leu Leu Asp Asp Asn Phe Asn Ser Lys Val Ala Asp Phe Gly<br>450 455 460 | 1392 | |
| ctt tct aga ctt ggc atg act gaa tca tcc cat atc tca aca gcc cca<br>Leu Ser Arg Leu Gly Met Thr Glu Ser Ser His Ile Ser Thr Ala Pro<br>465 470 475 480 | 1440 | |
| caa ggg act ccc ggc tac ctt gat cca cag tat cat cag aac ttc cat<br>Gln Gly Thr Pro Gly Tyr Leu Asp Pro Gln Tyr His Gln Asn Phe His<br>485 490 495 | 1488 | |
| ctc tca gat aaa agt gat gtt tac agt ttt gga gtg gtt ctt gta gag<br>Leu Ser Asp Lys Ser Asp Val Tyr Ser Phe Gly Val Val Leu Val Glu<br>500 505 510 | 1536 | |
| atc ata agt gca atg aaa gtg gtc gat ttt tct cga cct cac agt gag<br>Ile Ile Ser Ala Met Lys Val Val Asp Phe Ser Arg Pro His Ser Glu<br>515 520 525 | 1584 | |
| gtg aat ttg gct gca ctt gct att gac agg atc gga agg ggt tgt gtg<br>Val Asn Leu Ala Ala Leu Ala Ile Asp Arg Ile Gly Arg Gly Cys Val<br>530 535 540 | 1632 | |
| gat gaa ata ata gat cca ttc ttg gag cca cag agg gat gct tgg aca<br>Asp Glu Ile Ile Asp Pro Phe Leu Glu Pro Gln Arg Asp Ala Trp Thr<br>545 550 555 560 | 1680 | |
| ctt tgc tct att cac aag gtg gcc gag cta gca ttt aga tgc ctt gct | 1728 | |

```
Leu Cys Ser Ile His Lys Val Ala Glu Leu Ala Phe Arg Cys Leu Ala
                565                 570                 575
ttt cat agg gac atg agg cct tcc atg atg gag gta gca gat gag cta      1776
Phe His Arg Asp Met Arg Pro Ser Met Met Glu Val Ala Asp Glu Leu
                580                 585                 590
gag cat tgg atg ggc tcc aat gga gga gaa tat atg tgt ggc atc atc      1824
Glu His Trp Met Gly Ser Asn Gly Gly Glu Tyr Met Cys Gly Ile Ile
                595                 600                 605
agt ggc atc ttc ttt gag atg tcg cta ggt tgt atg tct gtt agg aag      1872
Ser Gly Ile Phe Phe Glu Met Ser Leu Gly Cys Met Ser Val Arg Lys
            610                 615                 620
gca ggg ata ggg agt cgg aga ttg ttt gtt cca cat agg cca aca gat      1920
Ala Gly Ile Gly Ser Arg Arg Leu Phe Val Pro His Arg Pro Thr Asp
625                 630                 635                 640
tgt ctg gct tca atg gaa gag ata aag gac agc tcc cct gtt tct gtg      1968
Cys Leu Ala Ser Met Glu Glu Ile Lys Asp Ser Ser Pro Val Ser Val
                645                 650                 655
cat gat cct tgg ttg agt gaa cag agc tca cct tca aca aac agc ttg      2016
His Asp Pro Trp Leu Ser Glu Gln Ser Ser Pro Ser Thr Asn Ser Leu
                660                 665                 670
ttg ggt aat gta gtt caa tga                                          2037
Leu Gly Asn Val Val Gln
            675

<210> SEQ ID NO 6
<211> LENGTH: 678
<212> TYPE: PRT
<213> ORGANISM: Vitis vinifera

<400> SEQUENCE: 6

Met Arg Lys Ala Leu Gln Arg Thr Ile Leu Ala Leu Ile Cys Thr Val
1               5                   10                  15

Thr Leu Val Ser Ala Ile Lys Asn Asp Ser Cys Gly Thr Gly Lys Ser
                20                  25                  30

Ala Lys Arg Val His Tyr Pro Phe Gly Phe Ser Ser Asp Ser Pro Ile
            35                  40                  45

Lys Leu Asn Cys Ser Lys Glu Gly Glu Ile Glu Ile Gln Asn Phe Lys
        50                  55                  60

Val Gln Asn Val Thr Thr Asp Ser Ile Ile Ile Asn Leu Pro Ala Gln
65                  70                  75                  80

Cys Gln Arg Glu Ile Gln Lys Ile Glu Pro Leu Phe Gly Lys Asn Tyr
                85                  90                  95

Ala Leu Ser Ser Lys Asn Ser Leu Leu Phe Gln Asn Cys Ser Ser Ser
            100                 105                 110

Ser Ser Gly Cys Val Ile Pro Thr Ser Val Phe Asn Gly Gln Asn Lys
        115                 120                 125

Leu Asn Asn Cys Asn Gly Lys Ser Asp Asn Asn Ile Ser Cys Phe Pro
    130                 135                 140

Leu Asp Ser Glu Ser Glu Phe Met Ser Phe Ala Asn Val Thr Gly Thr
145                 150                 155                 160

Gly Cys Lys Phe Leu Leu Leu Ser Met Ala Val Glu Trp Arg Asn Asn
                165                 170                 175

Ser Ala Val Ser Leu Glu Leu Gly Thr Ala Gln Leu Gly Trp Trp Leu
            180                 185                 190

Asp His Pro Cys His Cys Ala Pro Asn Ala Lys His Thr Asn Leu Thr
        195                 200                 205

Val Pro Gly Gly Phe Gly Cys Arg Cys Ser Cys Lys Glu Gly Phe Asp
    210                 215                 220
```

```
Gly Asp Gly Phe Lys Asp Gly Asp Cys Gln Glu Val Thr Asp Cys
225                 230                 235                 240

Asn Ala Ser Lys Tyr Met Ser Gly Thr Cys Gly Gly Thr Thr Arg Val
                245                 250                 255

Ala Val Leu Val Gly Gly Val Ile Val Gly Ala Ser Leu Met Ser Thr
                260                 265                 270

Val Ala Leu Ile Cys Tyr Cys Ile Arg Arg Ser Tyr Leu Arg Arg
            275                 280                 285

Arg Met Ser Ala Lys Arg Leu Ile Cys Glu Ala Ala Gly Asn Ser Ser
            290                 295                 300

Val Pro Leu Tyr Pro Tyr Lys Glu Val Glu Arg Ala Thr Asn Gly Phe
305                 310                 315                 320

Ser Glu Lys Gln Arg Leu Gly Thr Gly Ala Tyr Gly Thr Val Phe Ala
                325                 330                 335

Gly Lys Leu His Asn Asp Glu Trp Val Ala Ile Lys Lys Ile Arg Asn
                340                 345                 350

Arg Asp Asn Asp Ser Ile Glu Gln Val Met Asn Glu Ile Lys Leu Ile
            355                 360                 365

Ser Ser Val Asn His Pro Asn Leu Val Arg Leu Leu Gly Cys Cys Ile
            370                 375                 380

Glu Asn Gly Glu Gln Ile Leu Val Tyr Glu Phe Met Ala Asn Gly Thr
385                 390                 395                 400

Leu Ser Gln His Leu Gln Lys Glu Arg Gly Lys Gly Leu Pro Trp Thr
                405                 410                 415

Thr Arg Leu Asn Ile Ala Thr Glu Thr Ala Asn Ala Ile Ala His Leu
                420                 425                 430

His Ser Ala Ile Thr Pro Pro Ile Phe His Arg Asp Ile Lys Ser Ser
            435                 440                 445

Asn Ile Leu Leu Asp Asp Asn Phe Asn Ser Lys Val Ala Asp Phe Gly
450                 455                 460

Leu Ser Arg Leu Gly Met Thr Glu Ser Ser His Ile Ser Thr Ala Pro
465                 470                 475                 480

Gln Gly Thr Pro Gly Tyr Leu Asp Pro Gln Tyr His Gln Asn Phe His
                485                 490                 495

Leu Ser Asp Lys Ser Asp Val Tyr Ser Phe Gly Val Val Leu Val Glu
            500                 505                 510

Ile Ile Ser Ala Met Lys Val Val Asp Phe Ser Arg Pro His Ser Glu
            515                 520                 525

Val Asn Leu Ala Ala Leu Ala Ile Asp Arg Ile Gly Arg Gly Cys Val
530                 535                 540

Asp Glu Ile Ile Asp Pro Phe Leu Glu Pro Gln Arg Asp Ala Trp Thr
545                 550                 555                 560

Leu Cys Ser Ile His Lys Val Ala Glu Leu Ala Phe Arg Cys Leu Ala
                565                 570                 575

Phe His Arg Asp Met Arg Pro Ser Met Met Glu Val Ala Asp Glu Leu
            580                 585                 590

Glu His Trp Met Gly Ser Asn Gly Glu Tyr Met Cys Gly Ile Ile
            595                 600                 605

Ser Gly Ile Phe Phe Glu Met Ser Leu Gly Cys Met Ser Val Arg Lys
            610                 615                 620

Ala Gly Ile Gly Ser Arg Arg Leu Phe Val Pro His Arg Pro Thr Asp
625                 630                 635                 640

Cys Leu Ala Ser Met Glu Glu Ile Lys Asp Ser Ser Pro Val Ser Val
```

-continued

```
                    645                 650                 655
His Asp Pro Trp Leu Ser Glu Gln Ser Ser Pro Ser Thr Asn Ser Leu
            660                 665                 670

Leu Gly Asn Val Val Gln
        675

<210> SEQ ID NO 7
<211> LENGTH: 2088
<212> TYPE: DNA
<213> ORGANISM: Populus trichocarpa
<220> FEATURE:
<221> NAME/KEY: CDS
<222> LOCATION: (1)..(2088)

<400> SEQUENCE: 7 atg agt ctt cga cag gaa agt ttg ctt ctt ttc atc acc ttc atc acg        48
Met Ser Leu Arg Gln Glu Ser Leu Leu Leu Phe Ile Thr Phe Ile Thr
1               5                   10                  15 att ttt att gct acc aca agt cct aca act aaa gct cag aag tcc ggc        96
Ile Phe Ile Ala Thr Thr Ser Pro Thr Thr Lys Ala Gln Lys Ser Gly
                20                  25                  30 agc aat tgt gcc tct tca tgt ggg att ggg aaa tca gca aga gtt gtc       144
Ser Asn Cys Ala Ser Ser Cys Gly Ile Gly Lys Ser Ala Arg Val Val
            35                  40                  45 ccg tac cct ttt ggt ttc tca aat gga tgc ccc atc cag tta aac tgc       192
Pro Tyr Pro Phe Gly Phe Ser Asn Gly Cys Pro Ile Gln Leu Asn Cys
        50                  55                  60 gaa tca act gaa ggt gag atc aag att ggt gaa ttt caa gtc cag aac       240
Glu Ser Thr Glu Gly Glu Ile Lys Ile Gly Glu Phe Gln Val Gln Asn
65                  70                  75                  80 ata acc cca aat ggt atc ttg gtc aat ctt cca gca gac tgt aat cgt       288
Ile Thr Pro Asn Gly Ile Leu Val Asn Leu Pro Ala Asp Cys Asn Arg
                85                  90                  95 tct att gaa aca atc aga ccg ctt ttt ggt ctg aac tat ggt cct tct       336
Ser Ile Glu Thr Ile Arg Pro Leu Phe Gly Leu Asn Tyr Gly Pro Ser
            100                 105                 110 tgg caa aac agt ttg tta ctt caa aac tgt agc aag cct tca aat agt       384
Trp Gln Asn Ser Leu Leu Leu Gln Asn Cys Ser Lys Pro Ser Asn Ser
        115                 120                 125 tgt gtt att tca aga agt ccg ttt cag gga gag ttg cat tcg aaa aac       432
Cys Val Ile Ser Arg Ser Pro Phe Gln Gly Glu Leu His Ser Lys Asn
    130                 135                 140 tgt gag gct gct aaa aat gac aac ttg agt tgt tac tca cta ccg tac       480
Cys Glu Ala Ala Lys Asn Asp Asn Leu Ser Cys Tyr Ser Leu Pro Tyr
145                 150                 155                 160 tca ggt att gat act ttg agt tat gaa ggt gtg aat tca act cag tgt       528
Ser Gly Ile Asp Thr Leu Ser Tyr Glu Gly Val Asn Ser Thr Gln Cys
                165                 170                 175 agt tct gtt ttc tct tct ctt gct ctt ggg tcg gac agt ccg gtt gtc       576
Ser Ser Val Phe Ser Ser Leu Ala Leu Gly Ser Asp Ser Pro Val Val
            180                 185                 190 tct ttc cag tat gaa aga att gaa ttg gaa tgg tgg ctt gaa ggt cat       624
Ser Phe Gln Tyr Glu Arg Ile Glu Leu Glu Trp Trp Leu Glu Gly His
        195                 200                 205 tgt cgg gat act ttt tgc tca aag aac gcg aat tgt agc gag gtt aag       672
Cys Arg Asp Thr Phe Cys Ser Lys Asn Ala Asn Cys Ser Glu Val Lys
    210                 215                 220 ctc cag aat ggg act gtt gga ttc aga tgt cat tgc tat gac ggg ttc       720
Leu Gln Asn Gly Thr Val Gly Phe Arg Cys His Cys Tyr Asp Gly Phe
225                 230                 235                 240 gct gga gat ggg ttt acc acc ggg aat ggc tgc cgg aga ggt gag cca       768
```

-continued

| | | | | | | | | | | | | | |
|---|---|---|---|---|---|---|---|---|---|---|---|---|---|
| Ala | Gly | Asp | Gly | Phe | Thr | Thr | Gly | Asn | Gly | Cys | Arg | Arg | Gly | Glu | Pro |
| | | | 245 | | | | 250 | | | | | 255 | |

```
act tgg ctt tat att tgt tta cat tta ttc ttg ttt att atg agg        816
Thr Trp Leu Tyr Ile Cys Leu His Leu Phe Leu Leu Phe Ile Met Arg
            260                 265                 270 ctt att gct gga gct tca ttg atg gct gtt ttc gcc ctt ctc tgt tac    864
Leu Ile Ala Gly Ala Ser Leu Met Ala Val Phe Ala Leu Leu Cys Tyr
            275                 280                 285 ttt gtc aag aag aaa tcc act tca atg cga aat cgg tca agt gca aag    912
Phe Val Lys Lys Lys Ser Thr Ser Met Arg Asn Arg Ser Ser Ala Lys
        290                 295                 300 cgc ctt cta tgt gaa gct gca ggc aac tct agt gtt cca ttt ttc caa    960
Arg Leu Leu Cys Glu Ala Ala Gly Asn Ser Ser Val Pro Phe Phe Gln
305                 310                 315                 320 tat aaa gaa att gaa agg gcc act aat ggc ttc tca gag aaa caa agg    1008
Tyr Lys Glu Ile Glu Arg Ala Thr Asn Gly Phe Ser Glu Lys Gln Arg
                325                 330                 335 cta gga act gga gcc tat ggt aca gtt tat tca gga aaa ctc cac aat    1056
Leu Gly Thr Gly Ala Tyr Gly Thr Val Tyr Ser Gly Lys Leu His Asn
            340                 345                 350 gat gat ttg gtt gca ata aaa aag atc aaa cag aga gat act gac agc    1104
Asp Asp Leu Val Ala Ile Lys Lys Ile Lys Gln Arg Asp Thr Asp Ser
            355                 360                 365 ctt gat cta gtc atg aat gaa ata aag ctc ctt tca tcc gta agc cat    1152
Leu Asp Leu Val Met Asn Glu Ile Lys Leu Leu Ser Ser Val Ser His
    370                 375                 380 cca aat ctg gtt cgt ctt tta ggc tgt tgc cta gag gag gga gaa cca    1200
Pro Asn Leu Val Arg Leu Leu Gly Cys Cys Leu Glu Glu Gly Glu Pro
385                 390                 395                 400 atc cta gtc tat gaa ttt atg cct aat gga act ttg tgt cag cac cta    1248
Ile Leu Val Tyr Glu Phe Met Pro Asn Gly Thr Leu Cys Gln His Leu
                405                 410                 415 caa cga gag agg ggc aat ggg ctt ccg tgg act gtt agg ctt acc gtt    1296
Gln Arg Glu Arg Gly Asn Gly Leu Pro Trp Thr Val Arg Leu Thr Val
            420                 425                 430 gct gct gaa act gct aat gcc att gcg tat ctc cat tca gtc gtg aat    1344
Ala Ala Glu Thr Ala Asn Ala Ile Ala Tyr Leu His Ser Val Val Asn
            435                 440                 445 cca cca att tac cac cga gac ata aaa tct agc aac ata cta ttg gat    1392
Pro Pro Ile Tyr His Arg Asp Ile Lys Ser Ser Asn Ile Leu Leu Asp
    450                 455                 460 tac aac tat aga tca aag gta gct gat ttt ggt ctt tcc aga ctt ggc    1440
Tyr Asn Tyr Arg Ser Lys Val Ala Asp Phe Gly Leu Ser Arg Leu Gly
465                 470                 475                 480 atg gaa gaa tca tct cat ata tca acc gcc ccg caa gga act cca ggc    1488
Met Glu Glu Ser Ser His Ile Ser Thr Ala Pro Gln Gly Thr Pro Gly
                485                 490                 495 tat ctt gat cct caa tat cat caa tat ttc cat ctt tct gat aaa agt    1536
Tyr Leu Asp Pro Gln Tyr His Gln Tyr Phe His Leu Ser Asp Lys Ser
            500                 505                 510 gat gtt tac agt ttt ggg gta gtt ctc gta gag atc ata act gca cag    1584
Asp Val Tyr Ser Phe Gly Val Val Leu Val Glu Ile Ile Thr Ala Gln
            515                 520                 525 aaa gta gtt gat ttt tct cgc cca cac agt gag gtt aat ttg gct gca    1632
Lys Val Val Asp Phe Ser Arg Pro His Ser Glu Val Asn Leu Ala Ala
        530                 535                 540 ctt gcc att gat agg att gga aga ggt tgt gtg gat gag ata gta gat    1680
Leu Ala Ile Asp Arg Ile Gly Arg Gly Cys Val Asp Glu Ile Val Asp
545                 550                 555                 560 cca tat ctt gac ccg gat aga gat gcc tgg acc tta tca tca att cat    1728
```

```
                                                                                    1776
agc gtg gct gaa ctt gcg ttt aga tgc ctt gct ttt cat agg gat atg
Ser Val Ala Glu Leu Ala Phe Arg Cys Leu Ala Phe His Arg Asp Met
            580                 585                 590

1824
agg cct act atg atg gaa gtt gca gaa gag ctt gaa cag att agg ctt
Arg Pro Thr Met Met Glu Val Ala Glu Glu Leu Glu Gln Ile Arg Leu
        595                 600                 605

1872
agt gca tgg gtc ccc acc atg cac atg gca tca ccg tca tct tcc tct
Ser Ala Trp Val Pro Thr Met His Met Ala Ser Pro Ser Ser Ser Ser
    610                 615                 620

1920
cat ttc tcg gac cat gga agt cag aaa tca ctg ggt gtc tct gtt ggt
His Phe Ser Asp His Gly Ser Gln Lys Ser Leu Gly Val Ser Val Gly
625                 630                 635                 640

1968
aaa aag gca gca gta gct agt cgg aga tta ctt gtt cca cag aga aca
Lys Lys Ala Ala Val Ala Ser Arg Arg Leu Leu Val Pro Gln Arg Thr
                645                 650                 655

2016
gat agt ctg act tct ttg gaa gag gtg aag gat agc tct cca gtt tct
Asp Ser Leu Thr Ser Leu Glu Glu Val Lys Asp Ser Ser Pro Val Ser
            660                 665                 670

2064
gtg cag gat cct tgg tta agt gaa cag agc tca cca tca aca aac agc
Val Gln Asp Pro Trp Leu Ser Glu Gln Ser Ser Pro Ser Thr Asn Ser
        675                 680                 685

2088
ctg ttg gat aat gta gtt cat tga
Leu Leu Asp Asn Val Val His
    690                 695

<210> SEQ ID NO 8
<211> LENGTH: 695
<212> TYPE: PRT
<213> ORGANISM: Populus trichocarpa

<400> SEQUENCE: 8

Met Ser Leu Arg Gln Glu Ser Leu Leu Phe Ile Thr Phe Ile Thr
1               5                   10                  15

Ile Phe Ile Ala Thr Thr Ser Pro Thr Thr Lys Ala Gln Lys Ser Gly
            20                  25                  30

Ser Asn Cys Ala Ser Ser Cys Gly Ile Gly Lys Ser Ala Arg Val Val
        35                  40                  45

Pro Tyr Pro Phe Gly Phe Ser Asn Gly Cys Pro Ile Gln Leu Asn Cys
    50                  55                  60

Glu Ser Thr Glu Gly Glu Ile Lys Ile Gly Glu Phe Gln Val Gln Asn
65                  70                  75                  80

Ile Thr Pro Asn Gly Ile Leu Val Asn Leu Pro Ala Asp Cys Asn Arg
                85                  90                  95

Ser Ile Glu Thr Ile Arg Pro Leu Phe Gly Leu Asn Tyr Gly Pro Ser
            100                 105                 110

Trp Gln Asn Ser Leu Leu Leu Gln Asn Cys Ser Lys Pro Ser Asn Ser
        115                 120                 125

Cys Val Ile Ser Arg Ser Pro Phe Gln Gly Glu Leu His Ser Lys Asn
    130                 135                 140

Cys Glu Ala Ala Lys Asn Asp Asn Leu Ser Cys Tyr Ser Leu Pro Tyr
145                 150                 155                 160

Ser Gly Ile Asp Thr Leu Ser Tyr Glu Gly Val Asn Ser Thr Gln Cys
                165                 170                 175

Ser Ser Val Phe Ser Ser Leu Ala Leu Gly Ser Asp Ser Pro Val Val
            180                 185                 190

Ser Phe Gln Tyr Glu Arg Ile Glu Leu Glu Trp Trp Leu Glu Gly His
```

-continued

```
            195                 200                 205
Cys Arg Asp Thr Phe Cys Ser Lys Asn Ala Asn Cys Ser Glu Val Lys
    210                 215                 220

Leu Gln Asn Gly Thr Val Gly Phe Arg Cys His Cys Tyr Asp Gly Phe
225                 230                 235                 240

Ala Gly Asp Gly Phe Thr Thr Gly Asn Gly Cys Arg Arg Gly Glu Pro
                245                 250                 255

Thr Trp Leu Tyr Ile Cys Leu His Leu Phe Leu Leu Phe Ile Met Arg
                260                 265                 270

Leu Ile Ala Gly Ala Ser Leu Met Ala Val Phe Ala Leu Leu Cys Tyr
        275                 280                 285

Phe Val Lys Lys Lys Ser Thr Ser Met Arg Asn Arg Ser Ser Ala Lys
        290                 295                 300

Arg Leu Leu Cys Glu Ala Ala Gly Asn Ser Ser Val Pro Phe Phe Gln
305                 310                 315                 320

Tyr Lys Glu Ile Glu Arg Ala Thr Asn Gly Phe Ser Glu Lys Gln Arg
                325                 330                 335

Leu Gly Thr Gly Ala Tyr Gly Thr Val Tyr Ser Gly Lys Leu His Asn
                340                 345                 350

Asp Asp Leu Val Ala Ile Lys Lys Ile Lys Gln Arg Asp Thr Asp Ser
            355                 360                 365

Leu Asp Leu Val Met Asn Glu Ile Lys Leu Leu Ser Ser Val Ser His
        370                 375                 380

Pro Asn Leu Val Arg Leu Leu Gly Cys Cys Leu Glu Glu Gly Glu Pro
385                 390                 395                 400

Ile Leu Val Tyr Glu Phe Met Pro Asn Gly Thr Leu Cys Gln His Leu
                405                 410                 415

Gln Arg Glu Arg Gly Asn Gly Leu Pro Trp Thr Val Arg Leu Thr Val
                420                 425                 430

Ala Ala Glu Thr Ala Asn Ala Ile Ala Tyr Leu His Ser Val Val Asn
            435                 440                 445

Pro Pro Ile Tyr His Arg Asp Ile Lys Ser Ser Asn Ile Leu Leu Asp
450                 455                 460

Tyr Asn Tyr Arg Ser Lys Val Ala Asp Phe Gly Leu Ser Arg Leu Gly
465                 470                 475                 480

Met Glu Glu Ser Ser His Ile Ser Thr Ala Pro Gln Gly Thr Pro Gly
                485                 490                 495

Tyr Leu Asp Pro Gln Tyr His Gln Tyr Phe His Leu Ser Asp Lys Ser
            500                 505                 510

Asp Val Tyr Ser Phe Gly Val Val Leu Val Glu Ile Ile Thr Ala Gln
        515                 520                 525

Lys Val Val Asp Phe Ser Arg Pro His Ser Glu Val Asn Leu Ala Ala
        530                 535                 540

Leu Ala Ile Asp Arg Ile Gly Arg Gly Cys Val Asp Glu Ile Val Asp
545                 550                 555                 560

Pro Tyr Leu Asp Pro Asp Arg Asp Ala Trp Thr Leu Ser Ser Ile His
                565                 570                 575

Ser Val Ala Glu Leu Ala Phe Arg Cys Leu Ala Phe His Arg Asp Met
                580                 585                 590

Arg Pro Thr Met Met Glu Val Ala Glu Glu Leu Glu Gln Ile Arg Leu
            595                 600                 605

Ser Ala Trp Val Pro Thr Met His Met Ala Ser Pro Ser Ser Ser Ser
        610                 615                 620
```

```
His Phe Ser Asp His Gly Ser Gln Lys Ser Leu Gly Val Ser Val Gly
625                 630                 635                 640

Lys Lys Ala Ala Val Ala Ser Arg Arg Leu Leu Val Pro Gln Arg Thr
            645                 650                 655

Asp Ser Leu Thr Ser Leu Glu Glu Val Lys Asp Ser Ser Pro Val Ser
        660                 665                 670

Val Gln Asp Pro Trp Leu Ser Glu Gln Ser Ser Pro Ser Thr Asn Ser
    675                 680                 685

Leu Leu Asp Asn Val Val His
    690                 695

<210> SEQ ID NO 9
<211> LENGTH: 2115
<212> TYPE: DNA
<213> ORGANISM: Oryza sativa
<220> FEATURE:
<221> NAME/KEY: CDS
<222> LOCATION: (1)..(2115)

<400> SEQUENCE: 9 atg cgg ggc gcg gcg cgg cta ctc ctg cca ctg gtg gtg ctg ctg ctg      48
Met Arg Gly Ala Ala Arg Leu Leu Leu Pro Leu Val Val Leu Leu Leu
1               5                   10                  15 cac gca gca cgc gga tca gcg gga tcg acg ggc ggc gga ggc aac ggc      96
His Ala Ala Arg Gly Ser Ala Gly Ser Thr Gly Gly Gly Gly Asn Gly
            20                  25                  30 agc tgc acg cag agc tgc ggc cgc atg agg gtg ccg tac ccg ttc ggc     144
Ser Cys Thr Gln Ser Cys Gly Arg Met Arg Val Pro Tyr Pro Phe Gly
        35                  40                  45 ttc tcc aga ggc tgc acg gtt cag ctc ggc tgc gac gac gcc tcc ggc     192
Phe Ser Arg Gly Cys Thr Val Gln Leu Gly Cys Asp Asp Ala Ser Gly
    50                  55                  60 acc gcg tgg ctc ggc ggg acg cgc ggg ctg ggc ctg ctc gtg agc aac     240
Thr Ala Trp Leu Gly Gly Thr Arg Gly Leu Gly Leu Leu Val Ser Asn
65                  70                  75                  80 gtg acg ccg cgc gcc atc gtc ctc acc ctg ccc ccc aac tgc tcc cgc     288
Val Thr Pro Arg Ala Ile Val Leu Thr Leu Pro Pro Asn Cys Ser Arg
                85                  90                  95 ccg ctc aac gag tcc ctg gat gcg ctc ttc acc gac aac tac gcg ccc     336
Pro Leu Asn Glu Ser Leu Asp Ala Leu Phe Thr Asp Asn Tyr Ala Pro
            100                 105                 110 acc gcg cag aac gcc ctg gtc gtg agc tcg tgc gac ccg cag gcc gcc     384
Thr Ala Gln Asn Ala Leu Val Val Ser Ser Cys Asp Pro Gln Ala Ala
        115                 120                 125 gcc cgc ctc agc aac tgc agc atc cca ccc gag gcc tac ctc gag aag     432
Ala Arg Leu Ser Asn Cys Ser Ile Pro Pro Glu Ala Tyr Leu Glu Lys
    130                 135                 140 agc tgc aat tcc atc cgc tgc gtc tta cct tct acc aaa gcc aac gtc     480
Ser Cys Asn Ser Ile Arg Cys Val Leu Pro Ser Thr Lys Ala Asn Val
145                 150                 155                 160 gac ggg aca aac gtc aca gac cct ttc ttg aat aga agc gag atg cgg     528
Asp Gly Thr Asn Val Thr Asp Pro Phe Leu Asn Arg Ser Glu Met Arg
                165                 170                 175 cgg ctc ggc tcg gac tgc cgc ggg ctc gtg tcg gcg tcg atc tat tcg     576
Arg Leu Gly Ser Asp Cys Arg Gly Leu Val Ser Ala Ser Ile Tyr Ser
            180                 185                 190 aac acg gcg ggg ccg gcg ctg cag ctg acc gcg ctg gag ctg gat tgg     624
Asn Thr Ala Gly Pro Ala Leu Gln Leu Thr Ala Leu Glu Leu Asp Trp
        195                 200                 205 tgg gtg cag ggg cgg tgc ggc tgc tcg agc cac gcc atc tgc gac ggg     672
Trp Val Gln Gly Arg Cys Gly Cys Ser Ser His Ala Ile Cys Asp Gly
```

```
                210                 215                 220
ttc acc ccg ccg tct acg cag aag gag gcg ttc cgg tgc gag tgc cag        720
Phe Thr Pro Pro Ser Thr Gln Lys Glu Ala Phe Arg Cys Glu Cys Gln
225                 230                 235                 240 gag ggg ttc gag ggc gac ggc tac acc gcc ggc gcc ggt tgc cgg aga        768
Glu Gly Phe Glu Gly Asp Gly Tyr Thr Ala Gly Ala Gly Cys Arg Arg
                245                 250                 255 gtt cca aag tgt aat cct tca aaa tac cta tca gga tca tgt ggc aag        816
Val Pro Lys Cys Asn Pro Ser Lys Tyr Leu Ser Gly Ser Cys Gly Lys
            260                 265                 270 ttg gtt cag atc ggc ctt ctt gtg gca gga gtc ttt ttt gga gcc atg        864
Leu Val Gln Ile Gly Leu Leu Val Ala Gly Val Phe Phe Gly Ala Met
        275                 280                 285 gtg atg ggc atc acc tgc ttg gtg tac cac ctg ctg cgg cgc cgg tcg        912
Val Met Gly Ile Thr Cys Leu Val Tyr His Leu Leu Arg Arg Arg Ser
290                 295                 300 gcg gcc ctc cgg agc cag aag agc acg aag cgg ctg ctg tcg gag gcg        960
Ala Ala Leu Arg Ser Gln Lys Ser Thr Lys Arg Leu Leu Ser Glu Ala
305                 310                 315                 320 tcc tgc acg gtg ccc ttc tac acg tac cgc gag atc gat cgc gcc acc       1008
Ser Cys Thr Val Pro Phe Tyr Thr Tyr Arg Glu Ile Asp Arg Ala Thr
                325                 330                 335 aac ggc ttc gcc gag gac cag cgc ctt ggc acg ggc gcg tac ggc acg       1056
Asn Gly Phe Ala Glu Asp Gln Arg Leu Gly Thr Gly Ala Tyr Gly Thr
                340                 345                 350 gtg tac gcg ggg cgg ctg agc aac aac cgc ctc gtg gcc gtg aag cgg       1104
Val Tyr Ala Gly Arg Leu Ser Asn Asn Arg Leu Val Ala Val Lys Arg
            355                 360                 365 atc aag cag cgc gac aac gcc ggg ctg gac cgc gtg atg aac gag gtg       1152
Ile Lys Gln Arg Asp Asn Ala Gly Leu Asp Arg Val Met Asn Glu Val
        370                 375                 380 aag ctc gtg tcg tcg gtg agc cac cgc aac ctc gtc cgc ctc ctc ggc       1200
Lys Leu Val Ser Ser Val Ser His Arg Asn Leu Val Arg Leu Leu Gly
385                 390                 395                 400 tgc tgc atc gag cac ggg cag cag atc ctc gtc tac gag ttc atg ccc       1248
Cys Cys Ile Glu His Gly Gln Gln Ile Leu Val Tyr Glu Phe Met Pro
                405                 410                 415 aac ggc acg ctg gcg cag cac ctg cag cgg gag cgc ggc ccg gcc gtg       1296
Asn Gly Thr Leu Ala Gln His Leu Gln Arg Glu Arg Gly Pro Ala Val
                420                 425                 430 ccg tgg acg gtc cgc ctc cgc atc gcc gtc gag acg gcc aag gcc atc       1344
Pro Trp Thr Val Arg Leu Arg Ile Ala Val Glu Thr Ala Lys Ala Ile
            435                 440                 445 gcg tac ctg cac tcg gag gtg cac ccg ccc atc tac cac cgc gac atc       1392
Ala Tyr Leu His Ser Glu Val His Pro Pro Ile Tyr His Arg Asp Ile
        450                 455                 460 aag tcc agc aac atc ctg ctc gac cac gag tac aac tcc aag gtc gcc       1440
Lys Ser Ser Asn Ile Leu Leu Asp His Glu Tyr Asn Ser Lys Val Ala
465                 470                 475                 480 gac ttc ggg ctg tcg cgg atg ggc atg acg tcc gtc gac tcg tcg cac       1488
Asp Phe Gly Leu Ser Arg Met Gly Met Thr Ser Val Asp Ser Ser His
                485                 490                 495 atc tcc acc gcg ccg cag ggc acg ccg ggg tac gtc gac cct cag tac       1536
Ile Ser Thr Ala Pro Gln Gly Thr Pro Gly Tyr Val Asp Pro Gln Tyr
                500                 505                 510 cac cag aac ttc cac ctc tcg gac aag agc gac gtg tac agc ttc ggc       1584
His Gln Asn Phe His Leu Ser Asp Lys Ser Asp Val Tyr Ser Phe Gly
            515                 520                 525 gtc gtg ctc gtc gag atc atc acg gcc atg aag gcc gtc gac ttc agc       1632
Val Val Leu Val Glu Ile Ile Thr Ala Met Lys Ala Val Asp Phe Ser
```

```
                   530                   535                   540
cgg gtt ggc agc gag gtc aac ctg gcg cag ctg gcc gtc gac agg atc      1680
Arg Val Gly Ser Glu Val Asn Leu Ala Gln Leu Ala Val Asp Arg Ile
545                 550                 555                 560 ggg aaa ggc agc ctc gac gac atc gtc gac ccc tac cta gac ccg cac      1728
Gly Lys Gly Ser Leu Asp Asp Ile Val Asp Pro Tyr Leu Asp Pro His
                565                 570                 575 agg gac gcc tgg act ctc acg tcc atc cac aag gtg gcc gag ctg gcg      1776
Arg Asp Ala Trp Thr Leu Thr Ser Ile His Lys Val Ala Glu Leu Ala
            580                 585                 590 ttt cgg tgc ctg gcg ttc cac agc gag atg aga cct tcc atg gct gag      1824
Phe Arg Cys Leu Ala Phe His Ser Glu Met Arg Pro Ser Met Ala Glu
        595                 600                 605 gtc gcc gac gag ctg gaa cag att cag gtc agc ggg tgg gcg ccg tcc      1872
Val Ala Asp Glu Leu Glu Gln Ile Gln Val Ser Gly Trp Ala Pro Ser
    610                 615                 620 acg gat gac gcc aca ttc atg tca acg acg tcc tcg ctt tgc tcg tcg      1920
Thr Asp Asp Ala Thr Phe Met Ser Thr Thr Ser Ser Leu Cys Ser Ser
625                 630                 635                 640 gct cca tca cgt tgc acg gac aag tct tgg ggg acc gct aag agc aag      1968
Ala Pro Ser Arg Cys Thr Asp Lys Ser Trp Gly Thr Ala Lys Ser Lys
                645                 650                 655 agg cag gcc gcg gca aac gca gtg gta aag caa gag acg acg aag tgt      2016
Arg Gln Ala Ala Ala Asn Ala Val Val Lys Gln Glu Thr Thr Lys Cys
            660                 665                 670 gca gtc gcc gac tcc ccc gtg tcc gtg cag gag aga tgg ttc agc gat      2064
Ala Val Ala Asp Ser Pro Val Ser Val Gln Glu Arg Trp Phe Ser Asp
        675                 680                 685 agg agc tcc cct tcc tca aat agc ctg ctg agg aat agc tcc ctg aac      2112
Arg Ser Ser Pro Ser Ser Asn Ser Leu Leu Arg Asn Ser Ser Leu Asn
    690                 695                 700 taa                                                                   2115
```

<210> SEQ ID NO 10
<211> LENGTH: 704
<212> TYPE: PRT
<213> ORGANISM: Oryza sativa

<400> SEQUENCE: 10

```
Met Arg Gly Ala Ala Arg Leu Leu Leu Pro Leu Val Leu Leu Leu
1               5                   10                  15

His Ala Ala Arg Gly Ser Ala Gly Ser Thr Gly Gly Gly Asn Gly
            20                  25                  30

Ser Cys Thr Gln Ser Cys Gly Arg Met Arg Val Pro Tyr Pro Phe Gly
        35                  40                  45

Phe Ser Arg Gly Cys Thr Val Gln Leu Gly Cys Asp Asp Ala Ser Gly
    50                  55                  60

Thr Ala Trp Leu Gly Gly Thr Arg Gly Leu Gly Leu Leu Val Ser Asn
65                  70                  75                  80

Val Thr Pro Arg Ala Ile Val Leu Thr Leu Pro Pro Asn Cys Ser Arg
                85                  90                  95

Pro Leu Asn Glu Ser Leu Asp Ala Leu Phe Thr Asp Asn Tyr Ala Pro
            100                 105                 110

Thr Ala Gln Asn Ala Leu Val Val Ser Ser Cys Asp Pro Gln Ala Ala
        115                 120                 125

Ala Arg Leu Ser Asn Cys Ser Ile Pro Pro Glu Ala Tyr Leu Glu Lys
    130                 135                 140

Ser Cys Asn Ser Ile Arg Cys Val Leu Pro Ser Thr Lys Ala Asn Val
```

```
              145                 150                 155                 160
        Asp Gly Thr Asn Val Thr Asp Pro Phe Leu Asn Arg Ser Glu Met Arg
                        165                 170                 175

Arg Leu Gly Ser Asp Cys Arg Gly Leu Val Ser Ala Ser Ile Tyr Ser
                        180                 185                 190

Asn Thr Ala Gly Pro Ala Leu Gln Leu Thr Ala Leu Glu Leu Asp Trp
                        195                 200                 205

Trp Val Gln Gly Arg Cys Gly Cys Ser Ser His Ala Ile Cys Asp Gly
                        210                 215                 220

Phe Thr Pro Pro Ser Thr Gln Lys Glu Ala Phe Arg Cys Glu Cys Gln
        225                 230                 235                 240

Glu Gly Phe Glu Gly Asp Gly Tyr Thr Ala Gly Ala Gly Cys Arg Arg
                        245                 250                 255

Val Pro Lys Cys Asn Pro Ser Lys Tyr Leu Ser Gly Ser Cys Gly Lys
                        260                 265                 270

Leu Val Gln Ile Gly Leu Leu Val Ala Gly Val Phe Phe Gly Ala Met
                        275                 280                 285

Val Met Gly Ile Thr Cys Leu Val Tyr His Leu Leu Arg Arg Arg Ser
                        290                 295                 300

Ala Ala Leu Arg Ser Gln Lys Ser Thr Lys Arg Leu Leu Ser Glu Ala
        305                 310                 315                 320

Ser Cys Thr Val Pro Phe Tyr Thr Tyr Arg Glu Ile Asp Arg Ala Thr
                        325                 330                 335

Asn Gly Phe Ala Glu Asp Gln Arg Leu Gly Thr Gly Ala Tyr Gly Thr
                        340                 345                 350

Val Tyr Ala Gly Arg Leu Ser Asn Asn Arg Leu Val Ala Val Lys Arg
                        355                 360                 365

Ile Lys Gln Arg Asp Asn Ala Gly Leu Asp Arg Val Met Asn Glu Val
                        370                 375                 380

Lys Leu Val Ser Ser Val Ser His Arg Asn Leu Val Arg Leu Leu Gly
        385                 390                 395                 400

Cys Cys Ile Glu His Gly Gln Gln Ile Leu Val Tyr Glu Phe Met Pro
                        405                 410                 415

Asn Gly Thr Leu Ala Gln His Leu Gln Arg Glu Arg Gly Pro Ala Val
                        420                 425                 430

Pro Trp Thr Val Arg Leu Arg Ile Ala Val Glu Thr Ala Lys Ala Ile
                        435                 440                 445

Ala Tyr Leu His Ser Glu Val His Pro Pro Ile Tyr His Arg Asp Ile
        450                 455                 460

Lys Ser Ser Asn Ile Leu Leu Asp His Glu Tyr Asn Ser Lys Val Ala
        465                 470                 475                 480

Asp Phe Gly Leu Ser Arg Met Gly Met Thr Ser Val Asp Ser Ser His
                        485                 490                 495

Ile Ser Thr Ala Pro Gln Gly Thr Pro Gly Tyr Val Asp Pro Gln Tyr
                        500                 505                 510

His Gln Asn Phe His Leu Ser Asp Lys Ser Asp Val Tyr Ser Phe Gly
                        515                 520                 525

Val Val Leu Val Glu Ile Ile Thr Ala Met Lys Ala Val Asp Phe Ser
                        530                 535                 540

Arg Val Gly Ser Glu Val Asn Leu Ala Gln Leu Ala Val Asp Arg Ile
        545                 550                 555                 560

Gly Lys Gly Ser Leu Asp Asp Ile Val Asp Pro Tyr Leu Asp Pro His
                        565                 570                 575
```

```
Arg Asp Ala Trp Thr Leu Thr Ser Ile His Lys Val Ala Glu Leu Ala
            580                 585                 590

Phe Arg Cys Leu Ala Phe His Ser Glu Met Arg Pro Ser Met Ala Glu
        595                 600                 605

Val Ala Asp Glu Leu Glu Gln Ile Gln Val Ser Gly Trp Ala Pro Ser
    610                 615                 620

Thr Asp Ala Thr Phe Met Ser Thr Thr Ser Ser Leu Cys Ser Ser
625                 630                 635                 640

Ala Pro Ser Arg Cys Thr Asp Lys Ser Trp Gly Thr Ala Lys Ser Lys
                645                 650                 655

Arg Gln Ala Ala Ala Asn Ala Val Val Lys Gln Glu Thr Thr Lys Cys
            660                 665                 670

Ala Val Ala Asp Ser Pro Val Ser Val Gln Glu Arg Trp Phe Ser Asp
        675                 680                 685

Arg Ser Ser Pro Ser Ser Asn Ser Leu Leu Arg Asn Ser Ser Leu Asn
    690                 695                 700
```

```
<210> SEQ ID NO 11
<211> LENGTH: 2184
<212> TYPE: DNA
<213> ORGANISM: Zea mays
<220> FEATURE:
<221> NAME/KEY: CDS
<222> LOCATION: (1)..(2184)

<400> SEQUENCE: 11
```

| | | |
|---|---|---|
| atg cac cac cag ctc ctc ctc ttc ctc ttc ttg ctc ctc ctc gat gca<br>Met His His Gln Leu Leu Leu Phe Leu Phe Leu Leu Leu Leu Asp Ala<br>1               5                  10                  15 | | 48 |
| aca acc ttc gcg gcg ccc gcc ggg ccg tgc aac cgt cgg tgc gga agc<br>Thr Thr Phe Ala Ala Pro Ala Gly Pro Cys Asn Arg Arg Cys Gly Ser<br>              20                  25                  30 | | 96 |
| acg acc gtg ccg tac ccg ttc ggc ttc tcc ggc ggc ggg gcc tgc ccg<br>Thr Thr Val Pro Tyr Pro Phe Gly Phe Ser Gly Gly Gly Ala Cys Pro<br>          35                  40                  45 | | 144 |
| atc ctc ctc gcc tgc aac gcc acg gcg tcc acg gcg ctc ctc ccg cgc<br>Ile Leu Leu Ala Cys Asn Ala Thr Ala Ser Thr Ala Leu Leu Pro Arg<br>      50                  55                  60 | | 192 |
| agc acg gcc gcc gcc gcc gcg tcg tac ccg gtg caa tcg ttc gac tcc<br>Ser Thr Ala Ala Ala Ala Ser Tyr Pro Val Gln Ser Phe Asp Ser<br>65                  70                  75                  80 | | 240 |
| gcg gca tcc acc ttc ctg gtc tcc ctc gtg ccg tcg tgc ggc cgc ggc<br>Ala Ala Ser Thr Phe Leu Val Ser Leu Val Pro Ser Cys Gly Arg Gly<br>                  85                  90                  95 | | 288 |
| gtg gcc gag gcc agg gcg gcg ctg gga ggc gcc ggc tac ggc gtg tcg<br>Val Ala Glu Ala Arg Ala Ala Leu Gly Gly Ala Gly Tyr Gly Val Ser<br>              100                 105                 110 | | 336 |
| tcc cgc acc ggg ctg ttc ctc cgc ggc ggc tgc ggg cgc gcg gcg ggg<br>Ser Arg Thr Gly Leu Phe Leu Arg Gly Gly Cys Gly Arg Ala Ala Gly<br>          115                 120                 125 | | 384 |
| tcg agg tcg ccg agc gac tgc aac gtc ccc tcg ggc gtc atg gcc gcc<br>Ser Arg Ser Pro Ser Asp Cys Asn Val Pro Ser Gly Val Met Ala Ala<br>      130                 135                 140 | | 432 |
| atc ctc cgc acg gtg cag tgc ggc ggc ggc aac gac agc tcc tgg acg<br>Ile Leu Arg Thr Val Gln Cys Gly Gly Gly Asn Asp Ser Ser Trp Thr<br>145                 150                 155                 160 | | 480 |
| tgc gtg ctg tcc gcg ccg ccg gcc ccc ggc agc ccc gcg gcg aga<br>Cys Val Leu Ser Ala Pro Pro Ala Pro Gly Ser Pro Ala Ala Ala Arg<br>                  165                 170                 175 | | 528 |
| ggc cag ggc cag ttc atg cgc tgg gac gag gtg gcc gcc gcc ggg tgc | | 576 |

-continued

```
Gly Gln Gly Gln Phe Met Arg Trp Asp Glu Val Ala Ala Gly Cys
            180                 185                 190 gag gac gcg ctc acc tcg gcc gtg tac gcg tac tcg ccg cag ggc gtc       624
Glu Asp Ala Leu Thr Ser Ala Val Tyr Ala Tyr Ser Pro Gln Gly Val
            195                 200                 205 ccg tcc atc cag ttc ggc atc gcg gag atg ggc tgg tgg gtc gac ggg       672
Pro Ser Ile Gln Phe Gly Ile Ala Glu Met Gly Trp Trp Val Asp Gly
            210                 215                 220 aga tgc ggt gac gga ggc ggc ggc ggc cgg tgc gcg cgg aac gcg             720
Arg Cys Gly Asp Gly Gly Gly Gly Gly Arg Cys Ala Arg Asn Ala
225                 230                 235                 240 acg tgc cac gac gtg cag acg ccc ggc ggg gcc tgg ggg cac cgg tgc       768
Thr Cys His Asp Val Gln Thr Pro Gly Gly Ala Trp Gly His Arg Cys
                245                 250                 255 gcg tgc gtg gac ggg atg gcc gga gac ggg ttc gcc gcc ggg caa ggg       816
Ala Cys Val Asp Gly Met Ala Gly Asp Gly Phe Ala Ala Gly Gln Gly
            260                 265                 270 tgc tac tac gac ggc gct ccg aga gag cgt tcc gcg aag aag att gtc       864
Cys Tyr Tyr Asp Gly Ala Pro Arg Glu Arg Ser Ala Lys Lys Ile Val
            275                 280                 285 ctc gta gtt gca gca ggt gtt gcg gcg agc gtg gcg gcg gcc acc ggc       912
Leu Val Val Ala Ala Gly Val Ala Ala Ser Val Ala Ala Ala Thr Gly
            290                 295                 300 gcg ctt ctg ctg tgc tgg ctg cag tgc cgg cgg cgc aag gcc ggg cgc       960
Ala Leu Leu Leu Cys Trp Leu Gln Cys Arg Arg Arg Lys Ala Gly Arg
305                 310                 315                 320 tcg gcg tcg gag cgg ctg gcg gcg atg cgg ctg ctg tcg gag gcg gcg      1008
Ser Ala Ser Glu Arg Leu Ala Ala Met Arg Leu Leu Ser Glu Ala Ala
                325                 330                 335 acg tcg agc ggc gtg ccg gtg tac tcg tac ggc gag atc gcg cgc gcg      1056
Thr Ser Ser Gly Val Pro Val Tyr Ser Tyr Gly Glu Ile Ala Arg Ala
            340                 345                 350 acc aac tcc ttc tcg cac acg cac cgc ctg ggc acg ggc gcg tac ggc      1104
Thr Asn Ser Phe Ser His Thr His Arg Leu Gly Thr Gly Ala Tyr Gly
            355                 360                 365 acc gtg tac gtg ggc aag ctc ccg ggc acg ggc agc gcg ccg gcg cta      1152
Thr Val Tyr Val Gly Lys Leu Pro Gly Thr Gly Ser Ala Pro Ala Leu
            370                 375                 380 gtg gcc atc aag cgc ctg cgc cga cgc cac cac cac gac gag gac gag      1200
Val Ala Ile Lys Arg Leu Arg Arg Arg His His His Asp Glu Asp Glu
385                 390                 395                 400 gac gcg gcg gcg gag gcg gcg ctg ctg ctg aac gag atc aag ctc atc      1248
Asp Ala Ala Ala Glu Ala Ala Leu Leu Leu Asn Glu Ile Lys Leu Ile
                405                 410                 415 tcc tcc gtg agc cac ccg aac ctg gtc cgc ctc ctc ggc tgc tgc ctc      1296
Ser Ser Val Ser His Pro Asn Leu Val Arg Leu Leu Gly Cys Cys Leu
            420                 425                 430 gac ggc ggc gag cag gtg ctc gtc tac gag tac gtg ccc aac ggc acg      1344
Asp Gly Gly Glu Gln Val Leu Val Tyr Glu Tyr Val Pro Asn Gly Thr
            435                 440                 445 ctc tcc cag cac ctc cac tcc gca ggc gcc agc acc ggg ggc cgc ggc      1392
Leu Ser Gln His Leu His Ser Ala Gly Ala Ser Thr Gly Gly Arg Gly
            450                 455                 460 gcg ttg acg tgg cgc gcg cgg ctc ggc gtg gcg gtg gag acg gcg ggc      1440
Ala Leu Thr Trp Arg Ala Arg Leu Gly Val Ala Val Glu Thr Ala Gly
465                 470                 475                 480 gcc atc gcg cac ctg cac ggc atg cgg ccg ccc atc ttc cac cgc gac      1488
Ala Ile Ala His Leu His Gly Met Arg Pro Pro Ile Phe His Arg Asp
                485                 490                 495 gtc aag tcc agc aac atc ttg ctc gac gcc acg ttg cgc ccc aag ctg      1536
```

```
Val Lys Ser Ser Asn Ile Leu Leu Asp Ala Thr Leu Arg Pro Lys Leu
            500                 505                 510 gcc gac ttc ggc ctg tcc cgc gcc gtg gac cgc ctg gag gcc gcg cgc      1584
Ala Asp Phe Gly Leu Ser Arg Ala Val Asp Arg Leu Glu Ala Ala Arg
    515                 520                 525 tcg cac gtg tcc acc gcg ccg cag ggc aca ccc ggg tac gtg gac ccg      1632
Ser His Val Ser Thr Ala Pro Gln Gly Thr Pro Gly Tyr Val Asp Pro
530                 535                 540 gag tac cac cag aac ttc cac ctc tcc gac aag agc gac gtg tac agc      1680
Glu Tyr His Gln Asn Phe His Leu Ser Asp Lys Ser Asp Val Tyr Ser
545                 550                 555                 560 ttc ggc gtc gtg ctg cta gag ctc gtc acc gct atg aag gtc gtc gac      1728
Phe Gly Val Val Leu Leu Glu Leu Val Thr Ala Met Lys Val Val Asp
                565                 570                 575 ttc gac cgc ccg ccc gcc gag gtc aac ctc gcc tcc ctc gcg ctc gac      1776
Phe Asp Arg Pro Pro Ala Glu Val Asn Leu Ala Ser Leu Ala Leu Asp
                580                 585                 590 cgc atc ggc aag ggc cag gtc gcc gag atc gtc gac ccg gcc ctc ctt      1824
Arg Ile Gly Lys Gly Gln Val Ala Glu Ile Val Asp Pro Ala Leu Leu
            595                 600                 605 ggc gcc ggc gag gac tgg gta atg ggc tcc gtc cgc cac gtc agc gag      1872
Gly Ala Gly Glu Asp Trp Val Met Gly Ser Val Arg His Val Ser Glu
610                 615                 620 cta gcc ttc cgg tgc ctg gcg ttc cag aag gac gtc cgg ccg tct atg      1920
Leu Ala Phe Arg Cys Leu Ala Phe Gln Lys Asp Val Arg Pro Ser Met
625                 630                 635                 640 cgc gag gtg gcc gcc gag ctg cag cgg atc agg tcc gcc gcc ccg gac      1968
Arg Glu Val Ala Ala Glu Leu Gln Arg Ile Arg Ser Ala Ala Pro Asp
                645                 650                 655 ggc gcc gat ccc gag gag ccc gcg ggg tct agg ctc cgg cct gtg agt      2016
Gly Ala Asp Pro Glu Glu Pro Ala Gly Ser Arg Leu Arg Pro Val Ser
                660                 665                 670 atg atg gac atc cag atc gac gtg agc ttg ggc ggc ccg gac acg gcg      2064
Met Met Asp Ile Gln Ile Asp Val Ser Leu Gly Gly Pro Asp Thr Ala
            675                 680                 685 gca aag aag gcg gct tcg ccc gca aag aag gcg gct tcg ccc gtg tcg      2112
Ala Lys Lys Ala Ala Ser Pro Ala Lys Lys Ala Ala Ser Pro Val Ser
690                 695                 700 gtg cag gag gtg tgg gtc agc gac cgg agc tcg ccg tcc acc aac ggc      2160
Val Gln Glu Val Trp Val Ser Asp Arg Ser Ser Pro Ser Thr Asn Gly
705                 710                 715                 720 tcc atg ccg cgc ttt gct gcg tag                                       2184
Ser Met Pro Arg Phe Ala Ala
            725

<210> SEQ ID NO 12
<211> LENGTH: 727
<212> TYPE: PRT
<213> ORGANISM: Zea mays

<400> SEQUENCE: 12

Met His His Gln Leu Leu Leu Phe Leu Phe Leu Leu Leu Leu Asp Ala
1               5                   10                  15

Thr Thr Phe Ala Ala Pro Ala Gly Pro Cys Asn Arg Arg Cys Gly Ser
                20                  25                  30

Thr Thr Val Pro Tyr Pro Phe Gly Phe Ser Gly Gly Gly Ala Cys Pro
            35                  40                  45

Ile Leu Leu Ala Cys Asn Ala Thr Ala Ser Thr Ala Leu Leu Pro Arg
        50                  55                  60

Ser Thr Ala Ala Ala Ala Ala Ser Tyr Pro Val Gln Ser Phe Asp Ser
```

```
                65                  70                  75                  80
Ala Ala Ser Thr Phe Leu Val Ser Leu Val Pro Ser Cys Gly Arg Gly
                    85                  90                  95

Val Ala Glu Ala Arg Ala Leu Gly Gly Ala Gly Tyr Gly Val Ser
                100                 105                 110

Ser Arg Thr Gly Leu Phe Leu Arg Gly Gly Cys Gly Arg Ala Ala Gly
                115                 120                 125

Ser Arg Ser Pro Ser Asp Cys Asn Val Pro Ser Gly Val Met Ala Ala
            130                 135                 140

Ile Leu Arg Thr Val Gln Cys Gly Gly Asn Asp Ser Ser Trp Thr
145                 150                 155                 160

Cys Val Leu Ser Ala Pro Pro Ala Pro Gly Ser Pro Ala Ala Arg
                165                 170                 175

Gly Gln Gly Gln Phe Met Arg Trp Asp Glu Val Ala Ala Gly Cys
                180                 185                 190

Glu Asp Ala Leu Thr Ser Ala Val Tyr Ala Tyr Ser Pro Gln Gly Val
            195                 200                 205

Pro Ser Ile Gln Phe Gly Ile Ala Glu Met Gly Trp Trp Val Asp Gly
    210                 215                 220

Arg Cys Gly Asp Gly Gly Gly Gly Arg Cys Ala Arg Asn Ala
225                 230                 235                 240

Thr Cys His Asp Val Gln Thr Pro Gly Ala Trp Gly His Arg Cys
                245                 250                 255

Ala Cys Val Asp Gly Met Ala Gly Asp Gly Phe Ala Ala Gly Gln Gly
                260                 265                 270

Cys Tyr Tyr Asp Gly Ala Pro Arg Glu Arg Ser Ala Lys Lys Ile Val
        275                 280                 285

Leu Val Val Ala Ala Gly Val Ala Ala Ser Val Ala Ala Thr Gly
        290                 295                 300

Ala Leu Leu Leu Cys Trp Leu Gln Cys Arg Arg Arg Lys Ala Gly Arg
305                 310                 315                 320

Ser Ala Ser Glu Arg Leu Ala Ala Met Arg Leu Leu Ser Glu Ala Ala
                325                 330                 335

Thr Ser Ser Gly Val Pro Val Tyr Ser Tyr Gly Glu Ile Ala Arg Ala
                340                 345                 350

Thr Asn Ser Phe Ser His Thr His Arg Leu Gly Thr Gly Ala Tyr Gly
            355                 360                 365

Thr Val Tyr Val Gly Lys Leu Pro Gly Thr Gly Ser Ala Pro Ala Leu
    370                 375                 380

Val Ala Ile Lys Arg Leu Arg Arg His His His Asp Glu Asp
385                 390                 395                 400

Asp Ala Ala Ala Glu Ala Ala Leu Leu Leu Asn Glu Ile Lys Leu Ile
                405                 410                 415

Ser Ser Val Ser His Pro Asn Leu Val Arg Leu Leu Gly Cys Cys Leu
                420                 425                 430

Asp Gly Gly Glu Gln Val Leu Val Tyr Glu Tyr Val Pro Asn Gly Thr
            435                 440                 445

Leu Ser Gln His Leu His Ser Ala Gly Ala Ser Thr Gly Gly Arg Gly
        450                 455                 460

Ala Leu Thr Trp Arg Ala Arg Leu Gly Val Ala Val Glu Thr Ala Gly
465                 470                 475                 480

Ala Ile Ala His Leu His Gly Met Arg Pro Ile Phe His Arg Asp
                485                 490                 495
```

-continued

```
Val Lys Ser Ser Asn Ile Leu Leu Asp Ala Thr Leu Arg Pro Lys Leu
            500                 505                 510

Ala Asp Phe Gly Leu Ser Arg Ala Val Asp Arg Leu Glu Ala Ala Arg
            515                 520                 525

Ser His Val Ser Thr Ala Pro Gln Gly Thr Pro Gly Tyr Val Asp Pro
            530                 535                 540

Glu Tyr His Gln Asn Phe His Leu Ser Asp Lys Ser Asp Val Tyr Ser
545                 550                 555                 560

Phe Gly Val Val Leu Leu Glu Leu Val Thr Ala Met Lys Val Asp
                565                 570                 575

Phe Asp Arg Pro Pro Ala Glu Val Asn Leu Ala Ser Leu Ala Leu Asp
                580                 585                 590

Arg Ile Gly Lys Gly Gln Val Ala Glu Ile Val Asp Pro Ala Leu Leu
                595                 600                 605

Gly Ala Gly Glu Asp Trp Val Met Gly Ser Val Arg His Val Ser Glu
610                 615                 620

Leu Ala Phe Arg Cys Leu Ala Phe Gln Lys Asp Val Arg Pro Ser Met
625                 630                 635                 640

Arg Glu Val Ala Ala Glu Leu Gln Arg Ile Arg Ser Ala Ala Pro Asp
                645                 650                 655

Gly Ala Asp Pro Glu Glu Pro Ala Gly Ser Arg Leu Arg Pro Val Ser
                660                 665                 670

Met Met Asp Ile Gln Ile Asp Val Ser Leu Gly Gly Pro Asp Thr Ala
                675                 680                 685

Ala Lys Lys Ala Ala Ser Pro Ala Lys Lys Ala Ala Ser Pro Val Ser
                690                 695                 700

Val Gln Glu Val Trp Val Ser Asp Arg Ser Ser Pro Ser Thr Asn Gly
705                 710                 715                 720

Ser Met Pro Arg Phe Ala Ala
                725

<210> SEQ ID NO 13
<211> LENGTH: 1287
<212> TYPE: DNA
<213> ORGANISM: Marchantia polymorpha
<220> FEATURE:
<221> NAME/KEY: CDS
<222> LOCATION: (1)..(1287)

<400> SEQUENCE: 13 atg cca cgg ttt gca ttg cat gaa acc gta aga cgg aac ctc gcg agc        48
Met Pro Arg Phe Ala Leu His Glu Thr Val Arg Arg Asn Leu Ala Ser
1               5                   10                  15 aga ttc gga cgt tgc ttg tac gtg gga gcg acg aac aag gag aag gtg        96
Arg Phe Gly Arg Cys Leu Tyr Val Gly Ala Thr Asn Lys Glu Lys Val
                20                  25                  30 gtt cct cta ttc gac ggg gac aga gga aat ccg aag cga gcg cac gag       144
Val Pro Leu Phe Asp Gly Asp Arg Gly Asn Pro Lys Arg Ala His Glu
            35                  40                  45 tgg atg aga gta tat tgt aaa tgg gct gtg cag gag ggt ttg tcc cag       192
Trp Met Arg Val Tyr Cys Lys Trp Ala Val Gln Glu Gly Leu Ser Gln
        50                  55                  60 gac caa acg ctg tta att gcc gtg gat cat atg ttc gtc aac gcc tac       240
Asp Gln Thr Leu Leu Ile Ala Val Asp His Met Phe Val Asn Ala Tyr
65                  70                  75                  80 ggt tgg gca aca cag ttt ctc aat ggg gtg agc tgg gaa gaa ttt atg       288
Gly Trp Ala Thr Gln Phe Leu Asn Gly Val Ser Trp Glu Glu Phe Met
                85                  90                  95
```

```
act gga ttt tac cga gaa tac gtc acc aat aac ggg gca gtc att caa       336
Thr Gly Phe Tyr Arg Glu Tyr Val Thr Asn Asn Gly Ala Val Ile Gln
            100                 105                 110 gca gta cgg ggg tgg tat cgg atg ctg aaa aag gcc aag gca gta cct       384
Ala Val Arg Gly Trp Tyr Arg Met Leu Lys Lys Ala Lys Ala Val Pro
115                 120                 125 ttc ata cgt ttt tcg ggc agg gag ctt gca act gca acc gat gac ttt       432
Phe Ile Arg Phe Ser Gly Arg Glu Leu Ala Thr Ala Thr Asp Asp Phe
        130                 135                 140 gct cct cgt cat att gtc gga gaa ggg gga ttt ggt gtt gta tat atg       480
Ala Pro Arg His Ile Val Gly Glu Gly Gly Phe Gly Val Val Tyr Met
145                 150                 155                 160 gcc cat ctg cct ggg aac cag gtg gtt gct gtg aag aaa tta aag ggt       528
Ala His Leu Pro Gly Asn Gln Val Val Ala Val Lys Lys Leu Lys Gly
                    165                 170                 175 gcc agt aag gag gct atg cag cag gcg cac aac gaa gta gaa att ttg       576
Ala Ser Lys Glu Ala Met Gln Gln Ala His Asn Glu Val Glu Ile Leu
                180                 185                 190 tcc cag ttc aga cat ccg aat ctg gtg aaa ctt ttg gga tgt tgt ttg       624
Ser Gln Phe Arg His Pro Asn Leu Val Lys Leu Leu Gly Cys Cys Leu
            195                 200                 205 gaa cag agg gat cct ttg tta gta tat gag tac att cca aac gga aat       672
Glu Gln Arg Asp Pro Leu Leu Val Tyr Glu Tyr Ile Pro Asn Gly Asn
210                 215                 220 ctg atg cag cat ttg tgc ggg gag atg aag aaa acg ctg aca tgg gag       720
Leu Met Gln His Leu Cys Gly Glu Met Lys Lys Thr Leu Thr Trp Glu
225                 230                 235                 240 aac agg atg tca ata gct ata gga act gca gaa gcc atc acg cat ctg       768
Asn Arg Met Ser Ile Ala Ile Gly Thr Ala Glu Ala Ile Thr His Leu
                    245                 250                 255 cac agc tgt ggc agt tca ccg gtt tat cat cga gac gtg aag tcg aac       816
His Ser Cys Gly Ser Ser Pro Val Tyr His Arg Asp Val Lys Ser Asn
                260                 265                 270 aac att ctt ctg gac cat gac tta aat gca aag att gcg gac ttc ggt       864
Asn Ile Leu Leu Asp His Asp Leu Asn Ala Lys Ile Ala Asp Phe Gly
            275                 280                 285 cta tcc aag ttt gtc cag aca ctc aac ttc gtt gct act cac ata acc       912
Leu Ser Lys Phe Val Gln Thr Leu Asn Phe Val Ala Thr His Ile Thr
290                 295                 300 aca act cct caa gga acc cac ggg tac gtg gat cct tgc tac cta caa       960
Thr Thr Pro Gln Gly Thr His Gly Tyr Val Asp Pro Cys Tyr Leu Gln
305                 310                 315                 320 acg ttt cat ctc acc gag aag agc gac gtg tac agc ttt ggc att gtt      1008
Thr Phe His Leu Thr Glu Lys Ser Asp Val Tyr Ser Phe Gly Ile Val
                    325                 330                 335 ctt ttg gag ctt gtt gca gga atg cga gtg ttg gat atg agt aga ccc      1056
Leu Leu Glu Leu Val Ala Gly Met Arg Val Leu Asp Met Ser Arg Pro
                340                 345                 350 gaa ggt gag tgg tct ata gtt tat gtg gcc atc gac aga gtt acc aag      1104
Glu Gly Glu Trp Ser Ile Val Tyr Val Ala Ile Asp Arg Val Thr Lys
            355                 360                 365 gga agg ttt gaa tct ttc ctt gat cca aaa ttg aaa gaa agt gaa cca      1152
Gly Arg Phe Glu Ser Phe Leu Asp Pro Lys Leu Lys Glu Ser Glu Pro
370                 375                 380 gat tgc att gaa cag gca ctg gat att aca aca ttg gct ctc aag tgt      1200
Asp Cys Ile Glu Gln Ala Leu Asp Ile Thr Thr Leu Ala Leu Lys Cys
385                 390                 395                 400 ctg act ctg agc tta gag gac aga cct gtt atg aaa cag gtg ttg cag      1248
Leu Thr Leu Ser Leu Glu Asp Arg Pro Val Met Lys Gln Val Leu Gln
                    405                 410                 415
```

```
gag ttg cac tgc ata cag gat aat tgg gta ctg gta tga                    1287
Glu Leu His Cys Ile Gln Asp Asn Trp Val Leu Val
            420                 425
```

<210> SEQ ID NO 14
<211> LENGTH: 428
<212> TYPE: PRT
<213> ORGANISM: Marchantia polymorpha

<400> SEQUENCE: 14

```
Met Pro Arg Phe Ala Leu His Glu Thr Val Arg Arg Asn Leu Ala Ser
1               5                   10                  15

Arg Phe Gly Arg Cys Leu Tyr Val Gly Ala Thr Asn Lys Glu Lys Val
            20                  25                  30

Val Pro Leu Phe Asp Gly Asp Arg Gly Asn Pro Lys Arg Ala His Glu
        35                  40                  45

Trp Met Arg Val Tyr Cys Lys Trp Ala Val Gln Glu Gly Leu Ser Gln
    50                  55                  60

Asp Gln Thr Leu Leu Ile Ala Val Asp His Met Phe Val Asn Ala Tyr
65                  70                  75                  80

Gly Trp Ala Thr Gln Phe Leu Asn Gly Val Ser Trp Glu Glu Phe Met
                85                  90                  95

Thr Gly Phe Tyr Arg Glu Tyr Val Thr Asn Asn Gly Ala Val Ile Gln
            100                 105                 110

Ala Val Arg Gly Trp Tyr Arg Met Leu Lys Lys Ala Lys Ala Val Pro
        115                 120                 125

Phe Ile Arg Phe Ser Gly Arg Glu Leu Ala Thr Ala Thr Asp Asp Phe
130                 135                 140

Ala Pro Arg His Ile Val Gly Glu Gly Gly Phe Gly Val Val Tyr Met
145                 150                 155                 160

Ala His Leu Pro Gly Asn Gln Val Val Ala Val Lys Lys Leu Lys Gly
                165                 170                 175

Ala Ser Lys Glu Ala Met Gln Gln Ala His Asn Glu Val Glu Ile Leu
            180                 185                 190

Ser Gln Phe Arg His Pro Asn Leu Val Lys Leu Leu Gly Cys Cys Leu
        195                 200                 205

Glu Gln Arg Asp Pro Leu Leu Val Tyr Glu Tyr Ile Pro Asn Gly Asn
    210                 215                 220

Leu Met Gln His Leu Cys Gly Glu Met Lys Lys Thr Leu Thr Trp Glu
225                 230                 235                 240

Asn Arg Met Ser Ile Ala Ile Gly Thr Ala Glu Ala Ile Thr His Leu
                245                 250                 255

His Ser Cys Gly Ser Ser Pro Val Tyr His Arg Asp Val Lys Ser Asn
            260                 265                 270

Asn Ile Leu Leu Asp His Asp Leu Asn Ala Lys Ile Ala Asp Phe Gly
        275                 280                 285

Leu Ser Lys Phe Val Gln Thr Leu Asn Phe Val Ala Thr His Ile Thr
    290                 295                 300

Thr Thr Pro Gln Gly Thr His Gly Tyr Val Asp Pro Cys Tyr Leu Gln
305                 310                 315                 320

Thr Phe His Leu Thr Glu Lys Ser Asp Val Tyr Ser Phe Gly Ile Val
                325                 330                 335

Leu Leu Glu Leu Val Ala Gly Met Arg Val Leu Asp Met Ser Arg Pro
            340                 345                 350

Glu Gly Glu Trp Ser Ile Val Tyr Val Ala Ile Asp Arg Val Thr Lys
        355                 360                 365
```

```
Gly Arg Phe Glu Ser Phe Leu Asp Pro Lys Leu Lys Glu Ser Glu Pro
        370                 375                 380

Asp Cys Ile Glu Gln Ala Leu Asp Ile Thr Thr Leu Ala Leu Lys Cys
385                 390                 395                 400

Leu Thr Leu Ser Leu Glu Asp Arg Pro Val Met Lys Gln Val Leu Gln
                405                 410                 415

Glu Leu His Cys Ile Gln Asp Asn Trp Val Leu Val
            420                 425

<210> SEQ ID NO 15
<211> LENGTH: 861
<212> TYPE: DNA
<213> ORGANISM: Physcomitrella patens
<220> FEATURE:
<221> NAME/KEY: CDS
<222> LOCATION: (1)..(861)

<400> SEQUENCE: 15 ctt ttc acc tac aaa gag ctt gat cat gcc acg caa aat ttc agt gcg      48
Leu Phe Thr Tyr Lys Glu Leu Asp His Ala Thr Gln Asn Phe Ser Ala
1               5                   10                  15 aat cat cag cta ggg gaa gga ggt ttt gga acg gtg tat aaa ggg aaa      96
Asn His Gln Leu Gly Glu Gly Gly Phe Gly Thr Val Tyr Lys Gly Lys
            20                  25                  30 ctt tcg gat gga cga ctg gtt gct gtg aag aag ctc aat caa ggt gga     144
Leu Ser Asp Gly Arg Leu Val Ala Val Lys Lys Leu Asn Gln Gly Gly
        35                  40                  45 agt caa ggc ata caa caa ttt cac aat gaa gtt gag gtt ctc tcc aaa     192
Ser Gln Gly Ile Gln Gln Phe His Asn Glu Val Glu Val Leu Ser Lys
    50                  55                  60 gtg cgt cat ccg cac ttg gtc cag tta ctt ggt tgg tgc agg gag cga     240
Val Arg His Pro His Leu Val Gln Leu Leu Gly Trp Cys Arg Glu Arg
65                  70                  75                  80 ccc ctt ctt gtc tat gag tat cta cca aac ggg tca atc tcg tat cat     288
Pro Leu Leu Val Tyr Glu Tyr Leu Pro Asn Gly Ser Ile Ser Tyr His
                85                  90                  95 ctc cac gga gga aat aac gga cac ctc cct tgg gag acg agg tta ggc     336
Leu His Gly Gly Asn Asn Gly His Leu Pro Trp Glu Thr Arg Leu Gly
            100                 105                 110 att gca ata cag aca gca gaa gca ctt tct tat ctt cac ttt gtg gtg     384
Ile Ala Ile Gln Thr Ala Glu Ala Leu Ser Tyr Leu His Phe Val Val
        115                 120                 125 agc cca cca att ttt cat aga gat gtg aag aca act aat atc ctc ctt     432
Ser Pro Pro Ile Phe His Arg Asp Val Lys Thr Thr Asn Ile Leu Leu
    130                 135                 140 gat gag ggc ttc aaa gtt aaa gtt gct gat ttt ggt ctt tcg agg ttg     480
Asp Glu Gly Phe Lys Val Lys Val Ala Asp Phe Gly Leu Ser Arg Leu
145                 150                 155                 160 gtg gtg aac ctg gaa aat acc cac atc tca acg gca ccg caa ggg acc     528
Val Val Asn Leu Glu Asn Thr His Ile Ser Thr Ala Pro Gln Gly Thr
                165                 170                 175 cct ggt tac ctt gac cca gat tat cat gaa tct tat cat ctc tct gat     576
Pro Gly Tyr Leu Asp Pro Asp Tyr His Glu Ser Tyr His Leu Ser Asp
            180                 185                 190 aag agt gat gtt tac agt ttt ggg gtg gtg ttg atg gag ctt gtg acc     624
Lys Ser Asp Val Tyr Ser Phe Gly Val Val Leu Met Glu Leu Val Thr
        195                 200                 205 gct aag aaa gca gtg gat atg gca cgg gag cgg aag gaa atc aat tta     672
Ala Lys Lys Ala Val Asp Met Ala Arg Glu Arg Lys Glu Ile Asn Leu
    210                 215                 220
```

```
gct tca ctg gct gtg gct aaa atc cac tct gga tgt tta cat gag atc    720
Ala Ser Leu Ala Val Ala Lys Ile His Ser Gly Cys Leu His Glu Ile
225                 230                 235                 240 ctc gat cca aat ttg act gtt cag ttc cat gac aat cct atg atg caa    768
Leu Asp Pro Asn Leu Thr Val Gln Phe His Asp Asn Pro Met Met Gln
            245                 250                 255 gtt atg gtg gag caa gtt gca gag ctg gca ttc cgt tgt cta gcc tct    816
Val Met Val Glu Gln Val Ala Glu Leu Ala Phe Arg Cys Leu Ala Ser
        260                 265                 270 gaa aaa gac gac cga cct tcg atg aaa gaa gtg cta gca gag tta        861
Glu Lys Asp Asp Arg Pro Ser Met Lys Glu Val Leu Ala Glu Leu
    275                 280                 285
```

<210> SEQ ID NO 16
<211> LENGTH: 287
<212> TYPE: PRT
<213> ORGANISM: Physcomitrella patens

<400> SEQUENCE: 16

```
Leu Phe Thr Tyr Lys Glu Leu Asp His Ala Thr Gln Asn Phe Ser Ala
1               5                   10                  15

Asn His Gln Leu Gly Glu Gly Gly Phe Gly Thr Val Tyr Lys Gly Lys
            20                  25                  30

Leu Ser Asp Gly Arg Leu Val Ala Val Lys Lys Leu Asn Gln Gly Gly
        35                  40                  45

Ser Gln Gly Ile Gln Gln Phe His Asn Glu Val Glu Val Leu Ser Lys
    50                  55                  60

Val Arg His Pro His Leu Val Gln Leu Leu Gly Trp Cys Arg Glu Arg
65                  70                  75                  80

Pro Leu Leu Val Tyr Glu Tyr Leu Pro Asn Gly Ser Ile Ser Tyr His
                85                  90                  95

Leu His Gly Gly Asn Asn Gly His Leu Pro Trp Glu Thr Arg Leu Gly
            100                 105                 110

Ile Ala Ile Gln Thr Ala Glu Ala Leu Ser Tyr Leu His Phe Val Val
        115                 120                 125

Ser Pro Pro Ile Phe His Arg Asp Val Lys Thr Thr Asn Ile Leu Leu
    130                 135                 140

Asp Glu Gly Phe Lys Val Lys Val Ala Asp Phe Gly Leu Ser Arg Leu
145                 150                 155                 160

Val Val Asn Leu Glu Asn Thr His Ile Ser Thr Ala Pro Gln Gly Thr
                165                 170                 175

Pro Gly Tyr Leu Asp Pro Asp Tyr His Glu Ser Tyr His Leu Ser Asp
            180                 185                 190

Lys Ser Asp Val Tyr Ser Phe Gly Val Val Leu Met Glu Leu Val Thr
        195                 200                 205

Ala Lys Lys Ala Val Asp Met Ala Arg Glu Arg Lys Glu Ile Asn Leu
    210                 215                 220

Ala Ser Leu Ala Val Ala Lys Ile His Ser Gly Cys Leu His Glu Ile
225                 230                 235                 240

Leu Asp Pro Asn Leu Thr Val Gln Phe His Asp Asn Pro Met Met Gln
                245                 250                 255

Val Met Val Glu Gln Val Ala Glu Leu Ala Phe Arg Cys Leu Ala Ser
            260                 265                 270

Glu Lys Asp Asp Arg Pro Ser Met Lys Glu Val Leu Ala Glu Leu
        275                 280                 285
```

<210> SEQ ID NO 17

<211> LENGTH: 1869
<212> TYPE: DNA
<213> ORGANISM: Arabidopsis thaliana
<220> FEATURE:
<221> NAME/KEY: CDS
<222> LOCATION: (1)..(1869)

<400> SEQUENCE: 17

```
atg gca gaa act cct caa ccg tat ctc atc ttc gtc ttc ttc gtc ttc      48
Met Ala Glu Thr Pro Gln Pro Tyr Leu Ile Phe Val Phe Phe Val Phe
1               5                  10                  15 act cta acc gtt gct aca caa acc acc ggt tcg gtt aag tgc aaa aca      96
Thr Leu Thr Val Ala Thr Gln Thr Thr Gly Ser Val Lys Cys Lys Thr
            20                  25                  30 agt ttg ctc cgt tac ccg ttt ggt ttc tcc gac ggt tat ccg atc cga     144
Ser Leu Leu Arg Tyr Pro Phe Gly Phe Ser Asp Gly Tyr Pro Ile Arg
        35                  40                  45 ttc aac tgc tct gag ata acc gga gag gcc gtg atc ggt gaa ttc gct     192
Phe Asn Cys Ser Glu Ile Thr Gly Glu Ala Val Ile Gly Glu Phe Ala
    50                  55                  60 gtg caa gaa gtg aca aac tcc aac atc tac gtc gaa atc ccg ccg gtt     240
Val Gln Glu Val Thr Asn Ser Asn Ile Tyr Val Glu Ile Pro Pro Val
65                  70                  75                  80 tgc aaa cgc aac atc cgt aaa atc gaa caa ctt ttc cgg gaa aat ctt     288
Cys Lys Arg Asn Ile Arg Lys Ile Glu Gln Leu Phe Arg Glu Asn Leu
                85                  90                  95 gct ccg tcg aaa tta cag aac ata att ctc gtc caa gga tgc aag aaa     336
Ala Pro Ser Lys Leu Gln Asn Ile Ile Leu Val Gln Gly Cys Lys Lys
            100                 105                 110 cag aac aag tct tct aat tgc tta atc cgc aat aaa ttc gtt gaa aac     384
Gln Asn Lys Ser Ser Asn Cys Leu Ile Arg Asn Lys Phe Val Glu Asn
        115                 120                 125 cgg tta aat ctc agc aaa tgt aaa tct ccg gtt agc tgt ctc gac gga     432
Arg Leu Asn Leu Ser Lys Cys Lys Ser Pro Val Ser Cys Leu Asp Gly
    130                 135                 140 gca aca acg aca act gcc gat gtg atg agt tta ggc gac gtt gtg aac     480
Ala Thr Thr Thr Thr Ala Asp Val Met Ser Leu Gly Asp Val Val Asn
145                 150                 155                 160 gga agt gga tgt aag tat tgg ttc tct tct att tct caa tcg caa gtt     528
Gly Ser Gly Cys Lys Tyr Trp Phe Ser Ser Ile Ser Gln Ser Gln Val
                165                 170                 175 tcg gtc aat ttg ggt cga ctc aag ctt gat tgg tgg ctt aag gga agt     576
Ser Val Asn Leu Gly Arg Leu Lys Leu Asp Trp Trp Leu Lys Gly Ser
            180                 185                 190 tgc agt aac acc act tgc tcg gag aac gca gac tgt gcc aaa gtt aag     624
Cys Ser Asn Thr Thr Cys Ser Glu Asn Ala Asp Cys Ala Lys Val Lys
        195                 200                 205 ctc gac gac ggt gga ctc ggt cat cgc tgc act tgt cgt gaa gga ttt     672
Leu Asp Asp Gly Gly Leu Gly His Arg Cys Thr Cys Arg Glu Gly Phe
    210                 215                 220 agc ggt aaa gcc ttc acc gtg cct ggt ggt tgc cac cga tta gtt tac     720
Ser Gly Lys Ala Phe Thr Val Pro Gly Gly Cys His Arg Leu Val Tyr
225                 230                 235                 240 aaa cgc aaa gga cta cac aaa ctc gtt gtt ctt ggt act gcg ggg att     768
Lys Arg Lys Gly Leu His Lys Leu Val Val Leu Gly Thr Ala Gly Ile
                245                 250                 255 ttg gtt gga gtt tta gta atc gtg gtc ttg ata gct aca tat ttc ttc     816
Leu Val Gly Val Leu Val Ile Val Val Leu Ile Ala Thr Tyr Phe Phe
            260                 265                 270 cgg aac aag caa tct gcg tca tct gaa aga gca tca atc gcg aat cgc     864
Arg Asn Lys Gln Ser Ala Ser Ser Glu Arg Ala Ser Ile Ala Asn Arg
        275                 280                 285
```

-continued

| | | |
|---|---|---|
| ttg ctt tgc gag cta gcc gga aac tca agt gtt cct ttc tac acc tac<br>Leu Leu Cys Glu Leu Ala Gly Asn Ser Ser Val Pro Phe Tyr Thr Tyr<br>290                       295                            300 | | 912 |
| aaa gag att gag aaa gct acc gat agt ttc tcc gac aag aac atg ctc<br>Lys Glu Ile Glu Lys Ala Thr Asp Ser Phe Ser Asp Lys Asn Met Leu<br>305                       310                       315                       320 | | 960 |
| gga acc gga gca tac gga aca gtc tac gca ggc gaa ttc cca aac agc<br>Gly Thr Gly Ala Tyr Gly Thr Val Tyr Ala Gly Glu Phe Pro Asn Ser<br>                     325                       330                       335 | | 1008 |
| tca tgc gtc gct ata aaa cgt ctc aaa cac aaa gac act aca agc att<br>Ser Cys Val Ala Ile Lys Arg Leu Lys His Lys Asp Thr Thr Ser Ile<br>                  340                       345                       350 | | 1056 |
| gac caa gtt gtg aac gag atc aag ctt ctt tcc tct gtg agc cac cca<br>Asp Gln Val Val Asn Glu Ile Lys Leu Leu Ser Ser Val Ser His Pro<br>         355                       360                       365 | | 1104 |
| aat cta gta cgt ctc tta ggt tgt tgc ttt gca gat gga gaa ccg ttt<br>Asn Leu Val Arg Leu Leu Gly Cys Cys Phe Ala Asp Gly Glu Pro Phe<br>370                       375                            380 | | 1152 |
| cta gtc tat gag ttc atg cca aac gga act ctt tat cag cat tta caa<br>Leu Val Tyr Glu Phe Met Pro Asn Gly Thr Leu Tyr Gln His Leu Gln<br>385                       390                       395               400 | | 1200 |
| cac gag aga ggc caa cca cca ctt tct tgg cag ctc cga ctc gcc att<br>His Glu Arg Gly Gln Pro Pro Leu Ser Trp Gln Leu Arg Leu Ala Ile<br>                     405                       410                       415 | | 1248 |
| gcg tgt caa acc gca aac gca atc gca cat ctc cac tct tca gta aac<br>Ala Cys Gln Thr Ala Asn Ala Ile Ala His Leu His Ser Ser Val Asn<br>             420                       425                       430 | | 1296 |
| cct cct atc tac cac cga gac ata aaa tct agt aac atc ctc ctt gac<br>Pro Pro Ile Tyr His Arg Asp Ile Lys Ser Ser Asn Ile Leu Leu Asp<br>                  435                       440                       445 | | 1344 |
| cac gaa ttc aac tcc aag ata tct gat ttc gga ctc tct agg ctc ggc<br>His Glu Phe Asn Ser Lys Ile Ser Asp Phe Gly Leu Ser Arg Leu Gly<br>         450                       455                       460 | | 1392 |
| atg tct acc gat ttc gaa gcc tct cat atc tcc acg gct cca caa ggc<br>Met Ser Thr Asp Phe Glu Ala Ser His Ile Ser Thr Ala Pro Gln Gly<br>465                       470                       475               480 | | 1440 |
| act cca gga tac tta gat cct caa tat cac caa gat ttt cag ctc tcg<br>Thr Pro Gly Tyr Leu Asp Pro Gln Tyr His Gln Asp Phe Gln Leu Ser<br>                     485                       490                       495 | | 1488 |
| gac aag agt gat gtc tat agc ttt gga gtt gtt ctc gta gaa atc atc<br>Asp Lys Ser Asp Val Tyr Ser Phe Gly Val Val Leu Val Glu Ile Ile<br>             500                       505                       510 | | 1536 |
| tca ggc ttt aaa gtc ata gac ttc act cgt ccc tac tct gaa gtg aac<br>Ser Gly Phe Lys Val Ile Asp Phe Thr Arg Pro Tyr Ser Glu Val Asn<br>                  515                       520                       525 | | 1584 |
| cta gcc tct ctt gcc gtc gac agg atc gga aga ggg cgt gtg gta gat<br>Leu Ala Ser Leu Ala Val Asp Arg Ile Gly Arg Gly Arg Val Val Asp<br>530                       535                       540 | | 1632 |
| atc atc gat ccc tgc tta aac aaa gaa atc aat ccg aaa atg ttt gca<br>Ile Ile Asp Pro Cys Leu Asn Lys Glu Ile Asn Pro Lys Met Phe Ala<br>545                       550                       555                       560 | | 1680 |
| tct atc cac aac tta gca gaa ttg gcg ttt cgc tgc tta tcc ttt cac<br>Ser Ile His Asn Leu Ala Glu Leu Ala Phe Arg Cys Leu Ser Phe His<br>                     565                       570                       575 | | 1728 |
| aga aac atg agg cct acg atg gta gaa att acg gaa gat ctc cac cgg<br>Arg Asn Met Arg Pro Thr Met Val Glu Ile Thr Glu Asp Leu His Arg<br>             580                       585                       590 | | 1776 |
| att aag ctt atg cac tat ggt aca gag tca ggt aag ttc aaa aac cga<br>Ile Lys Leu Met His Tyr Gly Thr Glu Ser Gly Lys Phe Lys Asn Arg<br>595                       600                       605 | | 1824 |

```
tcc gaa ata gat atg aag aga caa caa tca ttt ccg aga gaa tga          1869
Ser Glu Ile Asp Met Lys Arg Gln Gln Ser Phe Pro Arg Glu
    610             615                 620
```

<210> SEQ ID NO 18
<211> LENGTH: 622
<212> TYPE: PRT
<213> ORGANISM: Arabidopsis thaliana

<400> SEQUENCE: 18

```
Met Ala Glu Thr Pro Gln Pro Tyr Leu Ile Phe Val Phe Val Phe
1               5                   10                  15

Thr Leu Thr Val Ala Thr Gln Thr Thr Gly Ser Val Lys Cys Lys Thr
                20                  25                  30

Ser Leu Leu Arg Tyr Pro Phe Gly Phe Ser Asp Gly Tyr Pro Ile Arg
            35                  40                  45

Phe Asn Cys Ser Glu Ile Thr Gly Glu Ala Val Ile Gly Glu Phe Ala
50                  55                  60

Val Gln Glu Val Thr Asn Ser Asn Ile Tyr Val Glu Ile Pro Pro Val
65                  70                  75                  80

Cys Lys Arg Asn Ile Arg Lys Ile Glu Gln Leu Phe Arg Glu Asn Leu
                85                  90                  95

Ala Pro Ser Lys Leu Gln Asn Ile Ile Leu Val Gln Gly Cys Lys Lys
            100                 105                 110

Gln Asn Lys Ser Ser Asn Cys Leu Ile Arg Asn Lys Phe Val Glu Asn
        115                 120                 125

Arg Leu Asn Leu Ser Lys Cys Lys Ser Pro Val Ser Cys Leu Asp Gly
    130                 135                 140

Ala Thr Thr Thr Thr Ala Asp Val Met Ser Leu Gly Asp Val Val Asn
145                 150                 155                 160

Gly Ser Gly Cys Lys Tyr Trp Phe Ser Ser Ile Ser Gln Ser Gln Val
                165                 170                 175

Ser Val Asn Leu Gly Arg Leu Lys Leu Asp Trp Trp Leu Lys Gly Ser
            180                 185                 190

Cys Ser Asn Thr Thr Cys Ser Glu Asn Ala Asp Cys Ala Lys Val Lys
        195                 200                 205

Leu Asp Asp Gly Gly Leu Gly His Arg Cys Thr Cys Arg Glu Gly Phe
    210                 215                 220

Ser Gly Lys Ala Phe Thr Val Pro Gly Gly Cys His Arg Leu Val Tyr
225                 230                 235                 240

Lys Arg Lys Gly Leu His Lys Leu Val Val Leu Gly Thr Ala Gly Ile
                245                 250                 255

Leu Val Gly Val Leu Val Ile Val Val Leu Ile Ala Thr Tyr Phe Phe
            260                 265                 270

Arg Asn Lys Gln Ser Ala Ser Ser Glu Arg Ala Ser Ile Ala Asn Arg
        275                 280                 285

Leu Leu Cys Glu Leu Ala Gly Asn Ser Ser Val Pro Phe Tyr Thr Tyr
    290                 295                 300

Lys Glu Ile Glu Lys Ala Thr Asp Ser Phe Ser Asp Lys Asn Met Leu
305                 310                 315                 320

Gly Thr Gly Ala Tyr Gly Thr Val Tyr Ala Gly Glu Phe Pro Asn Ser
                325                 330                 335

Ser Cys Val Ala Ile Lys Arg Leu Lys His Lys Asp Thr Thr Ser Ile
            340                 345                 350

Asp Gln Val Val Asn Glu Ile Lys Leu Leu Ser Ser Val Ser His Pro
```

```
                    355                 360                 365
Asn Leu Val Arg Leu Gly Cys Cys Phe Ala Asp Gly Glu Pro Phe
            370                 375                 380

Leu Val Tyr Glu Phe Met Pro Asn Gly Thr Leu Tyr Gln His Leu Gln
385                 390                 395                 400

His Glu Arg Gly Gln Pro Pro Leu Ser Trp Gln Leu Arg Leu Ala Ile
                405                 410                 415

Ala Cys Gln Thr Ala Asn Ala Ile Ala His Leu His Ser Ser Val Asn
                420                 425                 430

Pro Pro Ile Tyr His Arg Asp Ile Lys Ser Ser Asn Ile Leu Leu Asp
                435                 440                 445

His Glu Phe Asn Ser Lys Ile Ser Asp Phe Gly Leu Ser Arg Leu Gly
                450                 455                 460

Met Ser Thr Asp Phe Glu Ala Ser His Ile Ser Thr Ala Pro Gln Gly
465                 470                 475                 480

Thr Pro Gly Tyr Leu Asp Pro Gln Tyr His Gln Asp Phe Gln Leu Ser
                485                 490                 495

Asp Lys Ser Asp Val Tyr Ser Phe Gly Val Val Leu Val Glu Ile Ile
                500                 505                 510

Ser Gly Phe Lys Val Ile Asp Phe Thr Arg Pro Tyr Ser Glu Val Asn
                515                 520                 525

Leu Ala Ser Leu Ala Val Asp Arg Ile Gly Arg Gly Arg Val Val Asp
                530                 535                 540

Ile Ile Asp Pro Cys Leu Asn Lys Glu Ile Asn Pro Lys Met Phe Ala
545                 550                 555                 560

Ser Ile His Asn Leu Ala Glu Leu Ala Phe Arg Cys Leu Ser Phe His
                565                 570                 575

Arg Asn Met Arg Pro Thr Met Val Glu Ile Thr Glu Asp Leu His Arg
                580                 585                 590

Ile Lys Leu Met His Tyr Gly Thr Glu Ser Gly Lys Phe Lys Asn Arg
                595                 600                 605

Ser Glu Ile Asp Met Lys Arg Gln Gln Ser Phe Pro Arg Glu
610                 615                 620

<210> SEQ ID NO 19
<211> LENGTH: 34
<212> TYPE: DNA
<213> ORGANISM: Artificial Sequence
<220> FEATURE:
<223> OTHER INFORMATION: WAKL14 Primer

<400> SEQUENCE: 19
ggaagtcgac ggaaggtgat gaatgttgag atcg                                34

<210> SEQ ID NO 20
<211> LENGTH: 36
<212> TYPE: DNA
<213> ORGANISM: Artificial Sequence
<220> FEATURE:
<223> OTHER INFORMATION: WAKL14 Primer

<400> SEQUENCE: 20
ggaagtcgac gagacggtct actcctttga gaggtc                              36

<210> SEQ ID NO 21
<211> LENGTH: 36
<212> TYPE: DNA
<213> ORGANISM: Artificial Sequence
<220> FEATURE:
```

<223> OTHER INFORMATION: WAKL14 Primer

<400> SEQUENCE: 21
atatgcggcc gcagacggac aagattcggg tgactc                          36

<210> SEQ ID NO 22
<211> LENGTH: 37
<212> TYPE: DNA
<213> ORGANISM: Artificial Sequence
<220> FEATURE:
<223> OTHER INFORMATION: WAKL14 Primer

<400> SEQUENCE: 22
atatgcggcc gcggaatgtt accgagcaat gtatttg                         37

<210> SEQ ID NO 23
<211> LENGTH: 23
<212> TYPE: DNA
<213> ORGANISM: Artificial Sequence
<220> FEATURE:
<223> OTHER INFORMATION: ACTIN2 Primer

<400> SEQUENCE: 23
gatgggcaag tcatcacgat tgg                                        23

<210> SEQ ID NO 24
<211> LENGTH: 26
<212> TYPE: DNA
<213> ORGANISM: Artificial Sequence
<220> FEATURE:
<223> OTHER INFORMATION: ACTIN2 Primer

<400> SEQUENCE: 24
accaccgatc cagacactgt acttcc                                     26

<210> SEQ ID NO 25
<211> LENGTH: 25
<212> TYPE: DNA
<213> ORGANISM: Artificial Sequence
<220> FEATURE:
<223> OTHER INFORMATION: DIN1/SEN1 Primer

<400> SEQUENCE: 25
ggaaactggt catcggctat ttctc                                      25

<210> SEQ ID NO 26
<211> LENGTH: 27
<212> TYPE: DNA
<213> ORGANISM: Artificial Sequence
<220> FEATURE:
<223> OTHER INFORMATION: DIN1/SEN1 Primer

<400> SEQUENCE: 26
tctgtacatg taaggtacgt tgatggc                                    27

<210> SEQ ID NO 27
<211> LENGTH: 27
<212> TYPE: DNA
<213> ORGANISM: Artificial Sequence
<220> FEATURE:
<223> OTHER INFORMATION: DIN2/SRG2 Primer

<400> SEQUENCE: 27
gctaagggat cgtggttctt cattatc                                    27

<210> SEQ ID NO 28

```
<211> LENGTH: 25
<212> TYPE: DNA
<213> ORGANISM: Artificial Sequence
<220> FEATURE:
<223> OTHER INFORMATION: DIN2/SRG2 Primer

<400> SEQUENCE: 28
agcgtccatg tttagctcct tcatc                                         25

<210> SEQ ID NO 29
<211> LENGTH: 25
<212> TYPE: DNA
<213> ORGANISM: Artificial Sequence
<220> FEATURE:
<223> OTHER INFORMATION: DIN6 Primer

<400> SEQUENCE: 29
gtggaatact tgccgtgtta ggatg                                         25

<210> SEQ ID NO 30
<211> LENGTH: 28
<212> TYPE: DNA
<213> ORGANISM: Artificial Sequence
<220> FEATURE:
<223> OTHER INFORMATION: DIN6 Primer

<400> SEQUENCE: 30
gacttcacaa tcactaccag tacggaac                                      28
```